(12) United States Patent
Alapati et al.

(10) Patent No.: US 9,643,979 B2
(45) Date of Patent: May 9, 2017

(54) INHIBITORS OF DNA GYRASE FOR THE TREATMENT OF BACTERIAL INFECTIONS

(71) Applicant: Vitas Pharma Research Private Limited, Gachibowli, Hyderabad (IN)

(72) Inventors: Chandrasekhar Alapati, Hyderabad (IN); Ankita Banerjee, Sainikpuri (IN); Radha Rangarajan, Machapur (IN); Rajinder Kumar, Cambridge (GB)

(73) Assignee: Vitas Pharma Research Private Limited, Hyderabad (IN)

( * ) Notice: Subject to any disclaimer, the term of this patent is extended or adjusted under 35 U.S.C. 154(b) by 0 days.

(21) Appl. No.: 14/434,870

(22) PCT Filed: Oct. 8, 2013

(86) PCT No.: PCT/IB2013/059192
§ 371 (c)(1),
(2) Date: Apr. 10, 2015

(87) PCT Pub. No.: WO2014/057415
PCT Pub. Date: Apr. 17, 2014

(65) Prior Publication Data
US 2015/0284408 A1 Oct. 8, 2015

(30) Foreign Application Priority Data
Oct. 10, 2012 (IN) .......................... 2795/CHE/2012

(51) Int. Cl.
| | |
|---|---|
| *C07D 497/04* | (2006.01) |
| *C07D 451/02* | (2006.01) |
| *C07D 491/056* | (2006.01) |
| *C07D 401/04* | (2006.01) |
| *C07D 405/14* | (2006.01) |
| *C07D 409/14* | (2006.01) |
| *C07D 413/14* | (2006.01) |
| *C07D 417/14* | (2006.01) |
| *C07D 451/04* | (2006.01) |
| *C07D 471/04* | (2006.01) |
| *C07D 471/08* | (2006.01) |
| *C07D 491/107* | (2006.01) |

(52) U.S. Cl.
CPC ......... *C07D 497/04* (2013.01); *C07D 401/04* (2013.01); *C07D 405/14* (2013.01); *C07D 409/14* (2013.01); *C07D 413/14* (2013.01); *C07D 417/14* (2013.01); *C07D 451/02* (2013.01); *C07D 451/04* (2013.01); *C07D 471/04* (2013.01); *C07D 471/08* (2013.01); *C07D 491/056* (2013.01); *C07D 491/107* (2013.01)

(58) Field of Classification Search
CPC .. C07D 497/04; C07D 471/04; C07D 471/08; C07D 491/107; C07D 491/056; C07D 451/04; C07D 451/02; C07D 417/14; C07D 413/14; C07D 409/14; C07D 405/14; C07D 401/04
See application file for complete search history.

(56) References Cited

U.S. PATENT DOCUMENTS 7,691,850 B2 * 4/2010 Miller ................. C07D 471/04
514/224.2
2010/0256124 A1 10/2010 Davie et al.

OTHER PUBLICATIONS

Sumana, J of Applicable Chemistry, vol. 4(3), 818-827, 2015.*
Miles, Biorg Med Chem Lett, 2011, vol. 21, 7489-7495.*
International Search Report and Written Opinion of the International Searching Authority, for PCT/IB2013/059192, issued Mar. 21, 2014.
Miles et al. 'Novel amino-piperidines as potent antibacterials targeting bacterial type IIA topoisomerases', Bioorg. Med. Chem. Lett., 2011, vol. 21, pp. 7489-7495. p. 7489, col. 1, para 3; pp. 7492-7493, Table 1.

* cited by examiner

*Primary Examiner* — D M Seaman
(74) *Attorney, Agent, or Firm* — Bryan D. Zerhusen; Locke Lord LLP

(57) ABSTRACT

The present invention relates to compounds which specifically inhibit bacterial DNA Gyrase and can be used for the treatment of respiratory tract infections.

8 Claims, 1 Drawing Sheet

INHIBITORS OF DNA GYRASE FOR THE TREATMENT OF BACTERIAL INFECTIONS

CROSS-REFERENCE TO RELATED APPLICATIONS

The present disclosure is entitled to the benefit under 35 U.S.C. §120 and 365(c) of International Patent Application PCT/IB2013/059192, entitled, "Inhibitors of DNA Gyrase for the treatment of bacterial infections", filed, 8 Oct. 2013, which claims priority to Indian patent application 2795/CHE/2012, filed, 10 Oct. 2012, which are incorporated herein by reference in their entirety.

FIELD OF THE INVENTION

This invention is related to compounds which specifically inhibit bacterial DNA Gyrase for the treatment of bacterial infections.

BACKGROUND OF THE INVENTION

Antibacterial drug resistance is a worldwide problem; new mechanisms of resistance emerge periodically and spread rapidly across the globe. The growing rate of antimicrobial resistance in clinical and non clinical settings poses significant threat to human health and animals, not only in India but also globally (Lancet Infectious Diseases, 9, 228-36, 2009). Each mechanism of resistance renders yet another class of antibiotics ineffective, ultimately resulting in fewer and fewer therapeutic options for patients. In fact, WHO now recognizes antimicrobial resistance as one of three greatest threats to human health (Clinical Infectious Diseases 50, 1081-1083, 2010). To address the issue of drug resistance, new chemotypes that target critical pathways in bacteria must be developed. We have identified a novel series of compounds that inhibit DNA Gyrase, a member of the DNA Topoisomerase family, and have broad spectrum antimicrobial activity.

DNA Topoisomerases are involved in the transient breaking and rejoining of DNA during replication, transcription and recombination. They are well conserved across the bacterial species and essential for viability. There are two classes of Topoisomerases, depending on whether they introduce single stranded (type 1) or double stranded breaks (type 2). DNA Gyrase and Topo IV are Type 2 Topoisomerases. Gyrase is responsible for the introduction of negative supercoils into DNA to allow fork progression during replication. It is a heterodimer consisting of two subunits of GyrA and two subunits of GyrB (Reviewed in Infectious Disorders—Drug Targets 7, 3-9, 2007).

Gyrase is a clinically validated target. Inhibitors of this target, the fluoroquinolones have been in use since the 1960s but suffer widespread drug resistance. Despite extensive research, newer generations of fluoroquinolones have not overcome resistance effectively. Recently two non-fluoroquinolone inhibitors of Gyrase have been described. One of them is NXL101 and the other is GSK299423. NXL101 belongs to a novel quinoline class with potent activity against gram-positive bacteria, including methicillin- and fluoroquinolone-resistant strains (Antimicrobial Agents and Chemotherapy, 52, 3339-3349, 2008). GSK299423 shows potent antibacterial activity against MRSA, fluoroquinolone resistant strains of *S. aureus* and Gram negatives such as *E. coli, H. influenzae, M. catarrhalis* and *Klebsiella pneumoniae* (Nature, 466, 935-942, 2010). While the compound potently inhibits DNA Gyrase, it has serious hERG binding liability (BMCL, 21, 7489-7495, 2011). Similarly, NXL-101 causes QT prolongation, which led to its discontinuation from clinical development (North American Journal of Medical Science, 4, 537-47, 2012). Nevertheless, the target continues to be attractive and novel chemotypes directed against the target will have significant clinical benefits, once proven to be efficacious and safe.

DETAILED DESCRIPTION OF THE INVENTION

Figure 1:
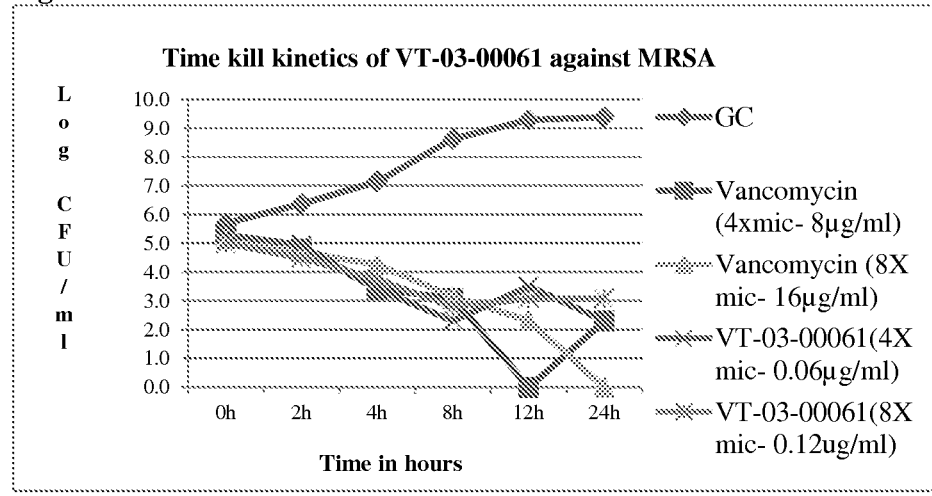
FIG. 1 discloses time kill kinetics of VT-03-00061 against MRSA 33591.

[1] The present invention provides compounds of formula (I) or pharmaceutically acceptable salts thereof:

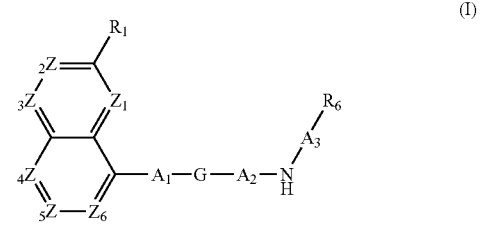

(I)

wherein, $Z_1$, $Z_2$, $Z_3$ are each independently $CR_1$;

$Z_4$, $Z_5$, $Z_6$ are each independently selected from a group consisting of N or $CR_1$;

$Z_2$ and $Z_3$ together form an optionally substituted saturated or unsaturated 5-6 membered cyclic ring which contains minimum one heteroatom at bridging or any other position of the ring;

$Z_5$ and $Z_6$ together form an optionally substituted saturated or unsaturated 5-6 membered cyclic ring which contains minimum one heteroatom at bridging or any other position of the ring;

$Z_4$ and $Z_6$ directly form a bond in absence of $Z_5$ where its substitution together form an optionally substituted saturated or unsaturated 5-6 membered cyclic ring containing at least one heteroatom at bridging or any other position of the ring;

$R_1$ are each independently selected from a group consisting of hydrogen, oxo, cyano, halogen, hydroxyl and $C_{1-6}$ alkyl optionally substituted with one or two $C_{1-6}$ alkoxy.

$A_1$ is selected from a group consisting of —$(CR_2R_3)_m$—$CH_2$—, —$CH_2$—$(CR_2R_3)_m$—, —NH—$(CR_2R_3)_m$—$CH_2$, —$(CR_2R_3)_m$—$CH_2$—O— and

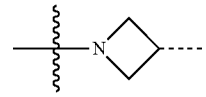

wherein, m is 1 or 2;

- - - - - is connectivity to G;

$R_2$ is selected from a group consisting of hydrogen, halogen, hydroxyl, acyloxy, $C_{1-6}$ alkyl optionally substituted with one or two $C_{1-6}$ alkoxy and $C_{1-6}$ alkoxy optionally substituted with $C_{1-6}$ alkyl
$R_3$ is hydrogen;
G is selected from a group of formulae consisting of G1, G2, G3, G4, G5, G6, G7, G8, G9 and G10 as provided below

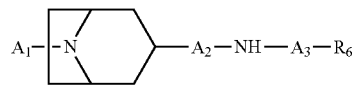
G1

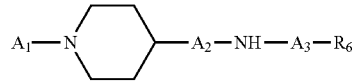
G2

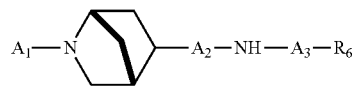
G3

G4

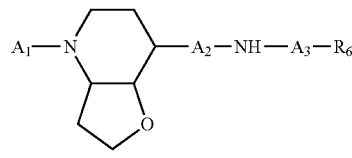
G5

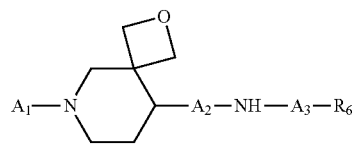
G6

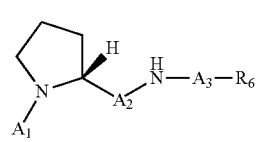
G7

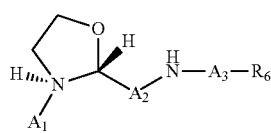
G8

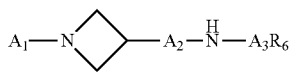
G9

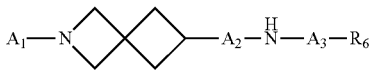
G10

$A_2$ is $CR_4R_5$ or is absent; wherein $R_4$ and $R_5$ are each independently hydrogen or $C_{1-6}$ alkyl; $A_3$ is —$CH_2$—, C(=O) or $SO_2$; wherein, $R_6$ is selected from a group consisting of i) substituted or unsubstituted monocyclic or bicyclic aryl;

ii) substituted or unsubstituted monocyclic or bicyclic heteroaryl;

iii) monocyclic aryl and hetero-aryl can be five or six membered ring bearing one or two hetero atom (N, O, S)

iv) aryl or hetero aryl ring substituted independently with halogen (F, Cl, Br), $NO_2$, CN, OMe, Me, $CF_3$, $OCF_3$, Ethyl, Butyl, isobutyl, small alkyl chain substituted with halogen, amino, $NMe_2$ alkoxy, carbonyl or sulfonyl.

v) the monocyclic or bicyclic aryl or heteroaryl is fused to saturated or unsaturated cyclic ring containing at least one heteroatom selected from the group consisting of oxygen, nitrogen and sulphur which is optionally substituted with halogen, $C_{1-6}$ alkyl, $C_{1-6}$ alkoxy, $C_{1-6}$ alkyl substituted with $C_{1-6}$ alkoxy, $C_{1-6}$ alkoxy optionally substituted with $C_{1-6}$ alkyl, $C_{1-4}$ haloalkoxy, $C_{1-4}$ haloalkyl, $C_{1-4}$ thioalkyl, nitro, cyano, carboxy, $C_{1-4}$ alkylsulfonyl, aminosulfonyl, hydroxyl, amino, aminoalkyl, oxo, hydroxyalkyl, alkynyl, alkylcarbonyl and carbonyl.

In one aspect, VT-03 compounds of the invention show minimal (insignificant) hERG binding activity indicating the advantage of these compounds as against the known compounds in the art (BMCL, 21, 7489-7495, 2011). VT-03 compounds of formula I of the invention are useful in the treatment of patients suffering from infections caused by *Staphylococcus* species, *Enterococcus* species, *Streptococcus* species, *Moraxella* species, *E. coli*, *Klebsiella* species, *Pseudomonas* species and *Acinetobacter* species.

[2] In an embodiment the instant invention provides preferred VT-03 compounds of formula I in Table I

TABLE I

VT-03 Compounds of the Invention

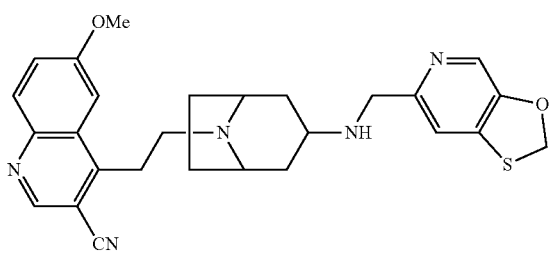 [SMILES: COc1ccc2ncc(C#N)c(CCN3C4CCC3CC(NCc3cc5c(cn3)OCS5)C4)c2c1]

VT-03-00014

TABLE I-continued
VT-03 Compounds of the Invention
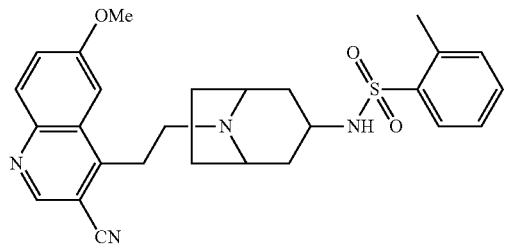 [SMILES: COc1ccc2ncc(C#N)c(CCN3C4CCC3CC(NS(=O)(=O)c3ccccc3C)C4)c2c1]
VT-03-00017
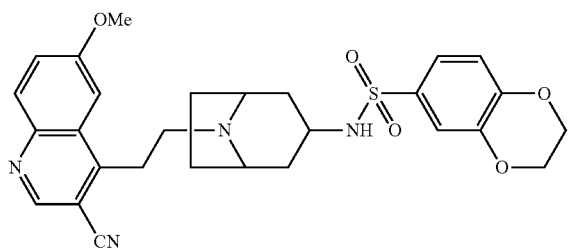 [SMILES: COc1ccc2ncc(C#N)c(CCN3C4CCC3CC(NS(=O)(=O)c3ccc5c(c3)OCCO5)C4)c2c1]
VT-03-00021
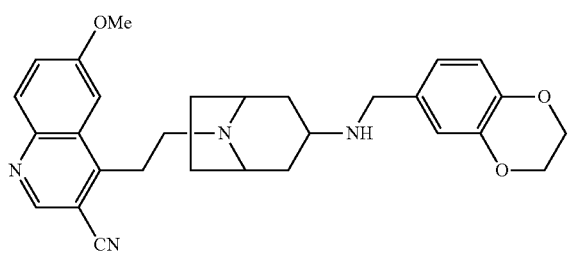 [SMILES: COc1ccc2ncc(C#N)c(CCN3C4CCC3CC(NCc3ccc5c(c3)OCCO5)C4)c2c1]
VT-03-00021a
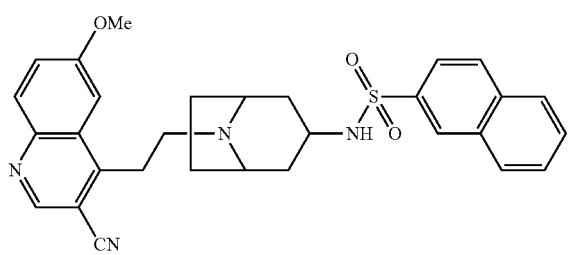 [SMILES: COc1ccc2ncc(C#N)c(CCN3C4CCC3CC(NS(=O)(=O)c3ccc5ccccc5c3)C4)c2c1]
VT-03-00022
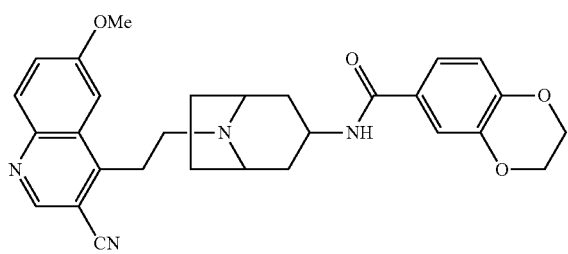 [SMILES: COc1ccc2ncc(C#N)c(CCN3C4CCC3CC(NC(=O)c3ccc5c(c3)OCCO5)C4)c2c1]
VT-03-00024
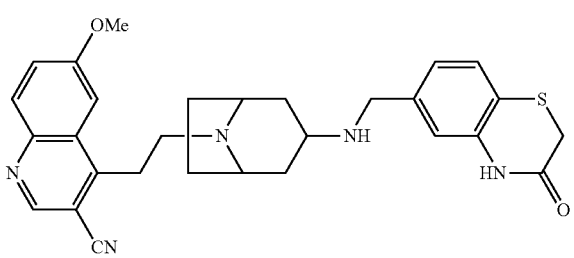 [SMILES: COc1ccc2ncc(C#N)c(CCN3C4CCC3CC(NCc3ccc5c(c3)NC(=O)CS5)C4)c2c1]
VT-03-00026

TABLE I-continued
VT-03 Compounds of the Invention
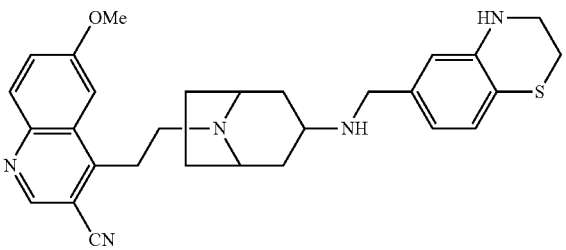 [SMILES: COc1ccc2ncc(C#N)c(CCN3C4CCC3CC(NCc3ccc5c(c3)NCCS5)C4)c2c1]
VT-03-00026a
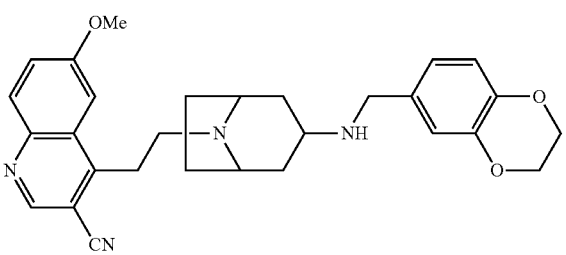 [SMILES: COc1ccc2ncc(C#N)c(CCN3C4CCC3CC(NCc3ccc5c(c3)OCCO5)C4)c2c1]
VT-03-00027
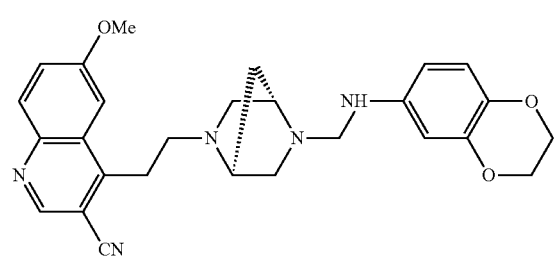 [SMILES: COc1ccc2ncc(C#N)c(CCN3C[C@@H]4C[C@H]3CN4CNc3ccc4c(c3)OCCO4)c2c1]
VT-03-00028
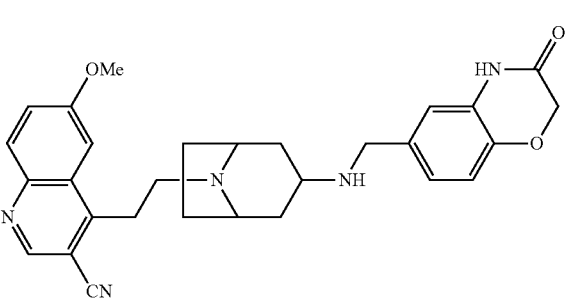 [SMILES: COc1ccc2ncc(C#N)c(CCN3C4CCC3CC(NCc3ccc5c(c3)NC(=O)CO5)C4)c2c1]
VT-03-00030
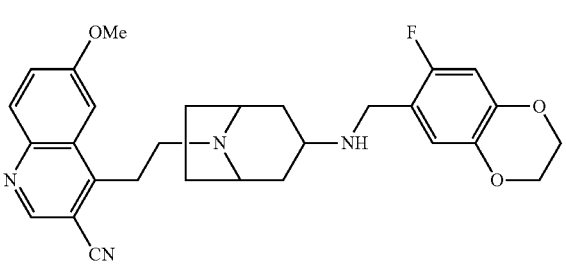 [SMILES: COc1ccc2ncc(C#N)c(CCN3C4CCC3CC(NCc3cc5c(cc3F)OCCO5)C4)c2c1]
VT-03-00031
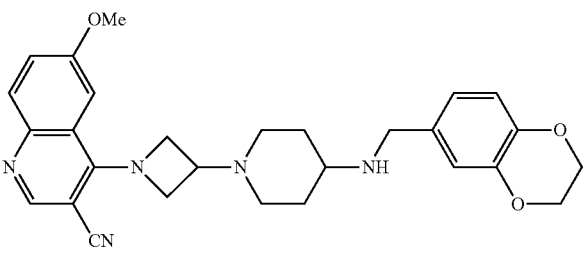 [SMILES: COc1ccc2ncc(C#N)c(N3CC(N4CCC(NCc5ccc6c(c5)OCCO6)CC4)C3)c2c1]
VT-03-00032

TABLE I-continued
VT-03 Compounds of the Invention
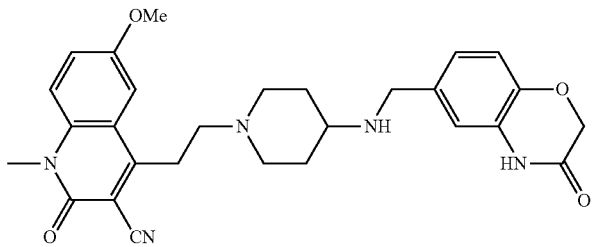 [SMILES: COc1ccc2c(c1)c(CCN1CCC(NCc3ccc4c(c3)NC(=O)CO4)CC1)c(C#N)c(=O)n2C]
VT-03-00042
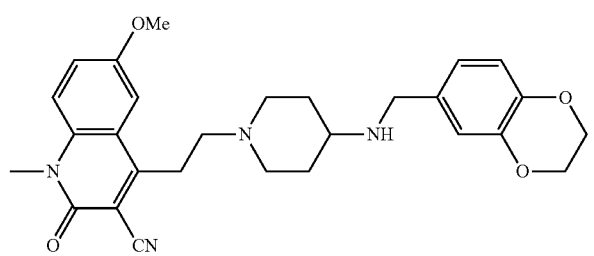 [SMILES: COc1ccc2c(c1)c(CCN1CCC(NCc3ccc4c(c3)OCCO4)CC1)c(C#N)c(=O)n2C]
VT-03-00043
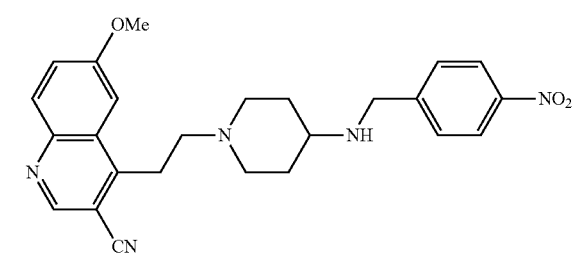 [SMILES: COc1ccc2ncc(C#N)c(CCN3CCC(NCc4ccc([N+](=O)[O-])cc4)CC3)c2c1]
VT-03-00045
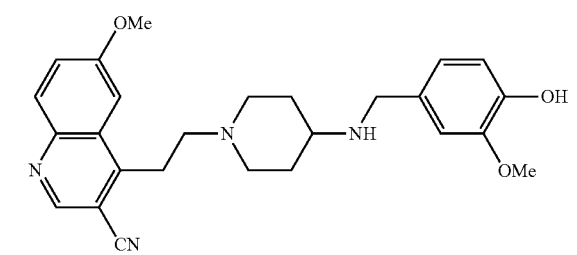 [SMILES: COc1ccc2ncc(C#N)c(CCN3CCC(NCc4ccc(O)c(OC)c4)CC3)c2c1]
VT-03-00046
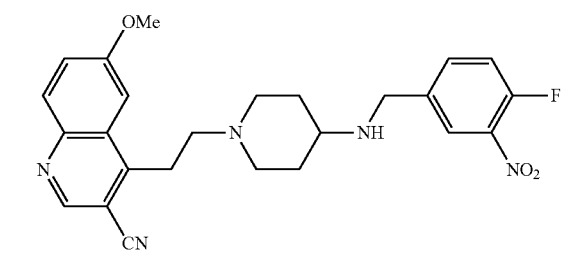 [SMILES: COc1ccc2ncc(C#N)c(CCN3CCC(NCc4ccc(F)c([N+](=O)[O-])c4)CC3)c2c1]
VT-03-00048
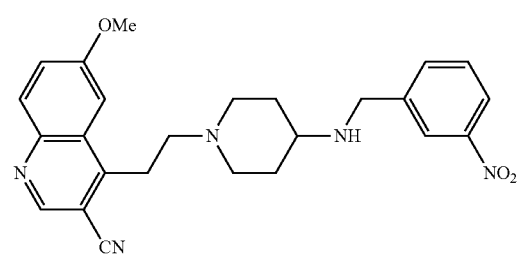 [SMILES: COc1ccc2ncc(C#N)c(CCN3CCC(NCc4cccc([N+](=O)[O-])c4)CC3)c2c1]
VT-03-00049

TABLE I-continued

VT-03 Compounds of the Invention

| Structure | ID |
|---|---|
| (6-methoxy-quinoline-3-CN, 4-ethyl-piperidine-4-NH-CH2-(2-fluoro-5-nitrophenyl)) | VT-03-00050 |
| (6-methoxy-quinoline-3-CN, 4-ethyl-piperidine-4-NH-CH2-(5-nitrofuran-2-yl)) | VT-03-00051 |
| (6-methoxy-quinoline-3-CN, 4-ethyl-piperidine-4-NH-CH2-(5-nitrothiophen-2-yl)) | VT-03-00052 |
| (6-methoxy-quinoline-3-CN, 4-ethyl-piperidine-4-NH-CH2-(5-nitrothiophen-3-yl)) | VT-03-00053 |
| (6-methoxy-quinoline-3-CN, 4-ethyl-piperidine-4-NH-CH2-(3-fluoro-4-nitrophenyl)) | VT-03-00054 |
| (6-methoxy-quinoline-3-CN, 4-ethyl-piperidine-4-NH-C(O)-(3-fluoro-4-nitrophenyl)) | VT-03-00055 |

TABLE I-continued

VT-03 Compounds of the Invention

| Structure | ID |
|---|---|
| (6-methoxyquinoxalin-2(1H)-one with N-ethyl-piperidin-4-yl-NH-CH2-(4-fluoro-3-nitrophenyl)) | VT-03-00056 |
| (6-methoxyquinoxalin-2(1H)-one with N-ethyl-piperidin-4-yl-NH-CH2-(5-nitrothiophen-3-yl)) | VT-03-00057 |
| (6-methoxy-3-cyanoquinolin-4-yl with ethyl-piperidin-4-yl-NH-CH2-(4-chloro-3-nitrophenyl)) | VT-03-00058 |
| (6-methoxy-3-cyanoquinolin-4-yl with ethyl-piperidin-4-yl-NH-CH2-(2-hydroxy-5-nitrophenyl)) | VT-03-00059 |
| (6-methoxy-3-cyanoquinolin-4-yl with ethyl-piperidin-4-yl-NH-CH2-(3-methoxy-4-hydroxy-5-nitrophenyl)) | VT-03-00060 |
| (6-methoxy-3-cyanoquinolin-4-yl with ethyl-piperidin-4-yl-NH-CH2-(4-methyl-3-nitrophenyl)) | VT-03-00061 |

TABLE I-continued
VT-03 Compounds of the Invention
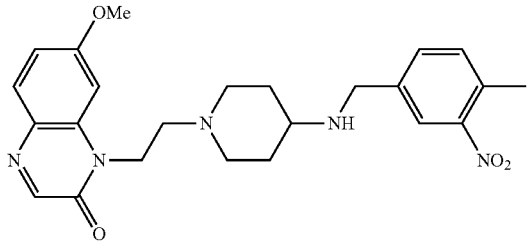 [SMILES: COc1ccc2ncc(=O)n(CCN3CCC(NCc4ccc(C)c([N+](=O)[O-])c4)CC3)c2c1]
VT-03-00062
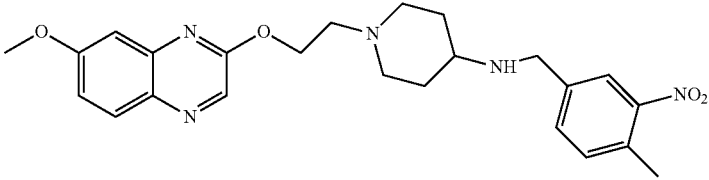 [SMILES: COc1ccc2ncc(OCCN3CCC(NCc4ccc(C)c([N+](=O)[O-])c4)CC3)nc2c1]
VT-03-00062a
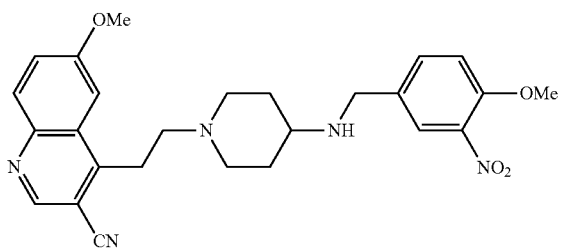 [SMILES: COc1ccc2ncc(C#N)c(CCN3CCC(NCc4ccc(OC)c([N+](=O)[O-])c4)CC3)c2c1]
VT-03-00063
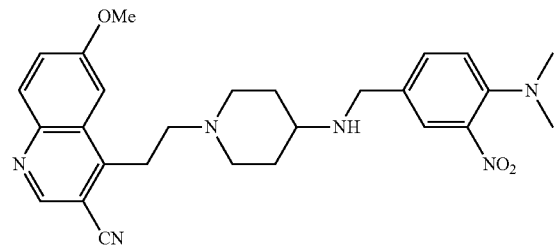 [SMILES: COc1ccc2ncc(C#N)c(CCN3CCC(NCc4ccc(N(C)C)c([N+](=O)[O-])c4)CC3)c2c1]
VT-03-00064
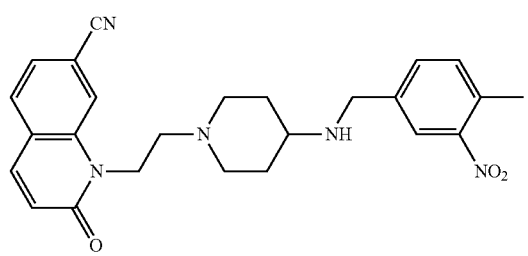 [SMILES: Cc1ccc(CNC2CCN(CCn3c(=O)ccc4ccc(C#N)cc43)CC2)cc1[N+](=O)[O-]]
VT-03-00065
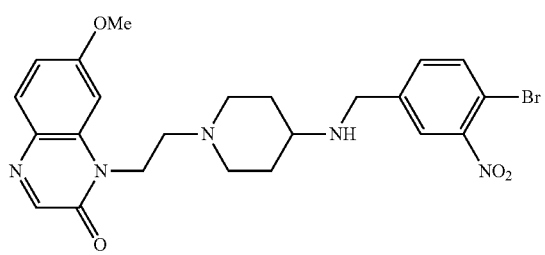 [SMILES: COc1ccc2ncc(=O)n(CCN3CCC(NCc4ccc(Br)c([N+](=O)[O-])c4)CC3)c2c1]
VT-03-00066

TABLE I-continued
VT-03 Compounds of the Invention
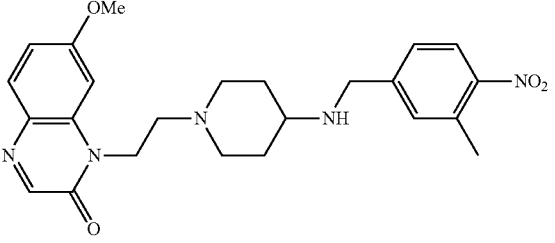 [SMILES: COc1ccc2ncc(=O)n(CCN3CCC(NCc4ccc([N+](=O)[O-])c(C)c4)CC3)c2c1]
VT-03-00067
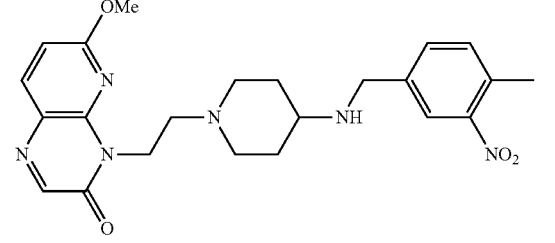 [SMILES: COc1ccc2ncc(=O)n(CCN3CCC(NCc4ccc(C)c([N+](=O)[O-])c4)CC3)c2n1]
VT-03-00068
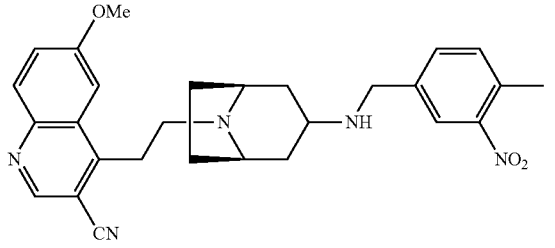 [SMILES: COc1ccc2ncc(C#N)c(CCN3[C@@H]4CC[C@H]3CC(NCc3ccc(C)c([N+](=O)[O-])c3)C4)c2c1]
VT-03-00069
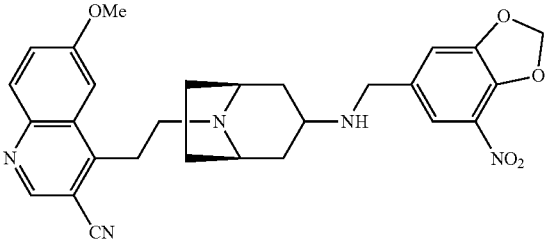 [SMILES: COc1ccc2ncc(C#N)c(CCN3[C@@H]4CC[C@H]3CC(NCc3cc5c(c([N+](=O)[O-])c3)OCO5)C4)c2c1]
VT-03-00070
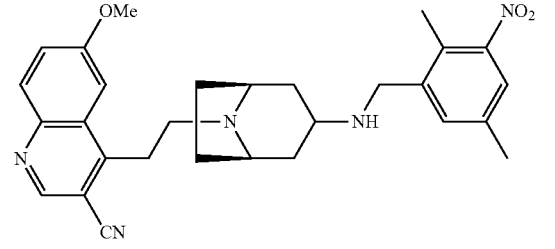 [SMILES: COc1ccc2ncc(C#N)c(CCN3[C@@H]4CC[C@H]3CC(NCc3cc(C)cc([N+](=O)[O-])c3C)C4)c2c1]
VT-03-00071
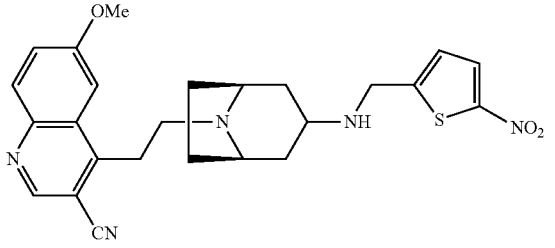 [SMILES: COc1ccc2ncc(C#N)c(CCN3[C@@H]4CC[C@H]3CC(NCc3ccc([N+](=O)[O-])s3)C4)c2c1]
VT-03-00072

TABLE I-continued
VT-03 Compounds of the Invention
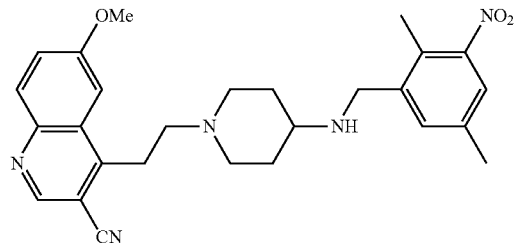 [SMILES: COc1ccc2ncc(C#N)c(CCN3CCC(NCc4cc(C)cc([N+](=O)[O-])c4C)CC3)c2c1]
VT-03-00074
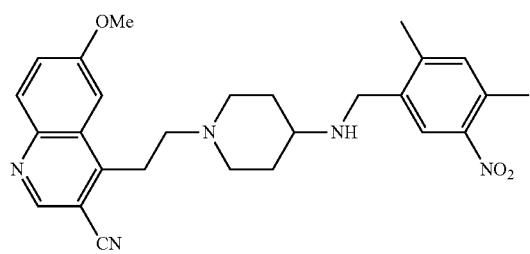 [SMILES: COc1ccc2ncc(C#N)c(CCN3CCC(NCc4cc([N+](=O)[O-])c(C)cc4C)CC3)c2c1]
VT-03-00075
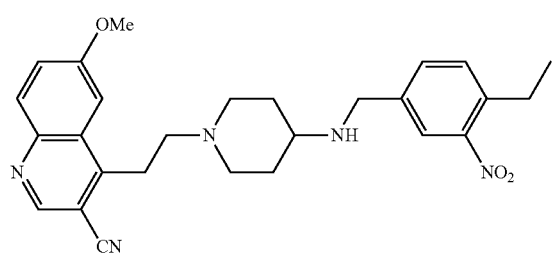 [SMILES: CCc1ccc(CNC2CCN(CCc3c(C#N)cnc4ccc(OC)cc34)CC2)cc1[N+](=O)[O-]]
VT-03-00076
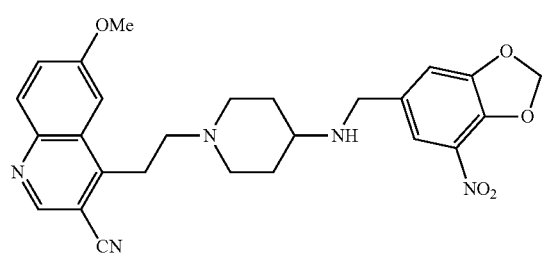 [SMILES: COc1ccc2ncc(C#N)c(CCN3CCC(NCc4cc5c(c([N+](=O)[O-])c4)OCO5)CC3)c2c1]
VT-03-00077
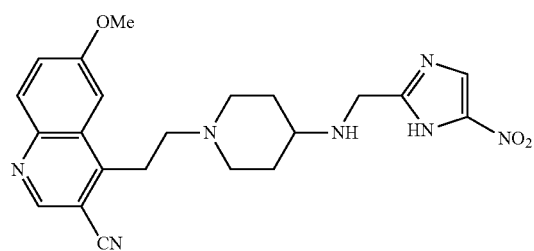 [SMILES: COc1ccc2ncc(C#N)c(CCN3CCC(NCc4ncc([N+](=O)[O-])[nH]4)CC3)c2c1]
VT-03-00078
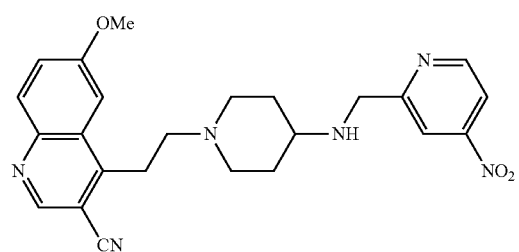 [SMILES: COc1ccc2ncc(C#N)c(CCN3CCC(NCc4cc([N+](=O)[O-])ccn4)CC3)c2c1]
VT-03-00079

TABLE I-continued
VT-03 Compounds of the Invention
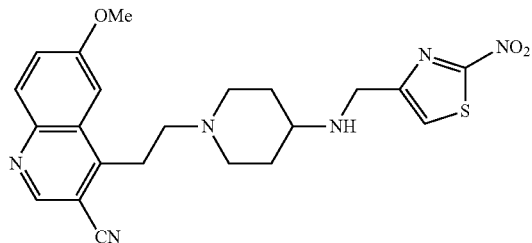 [SMILES: COc1ccc2ncc(C#N)c(CCN3CCC(NCc4csc([N+](=O)[O-])n4)CC3)c2c1]
VT-03-00080
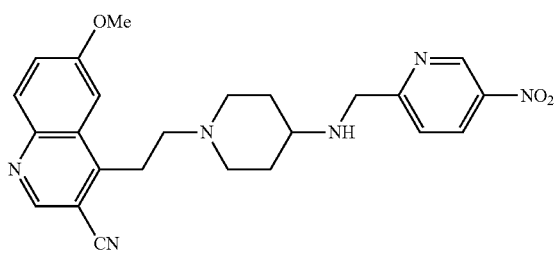 [SMILES: COc1ccc2ncc(C#N)c(CCN3CCC(NCc4ccc([N+](=O)[O-])cn4)CC3)c2c1]
VT-03-00081
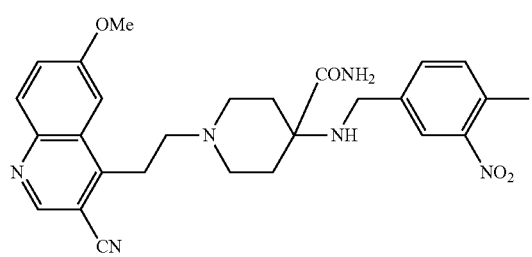 [SMILES: COc1ccc2ncc(C#N)c(CCN3CCC(NCc4ccc(C)c([N+](=O)[O-])c4)(C(N)=O)CC3)c2c1]
VT-03-00083
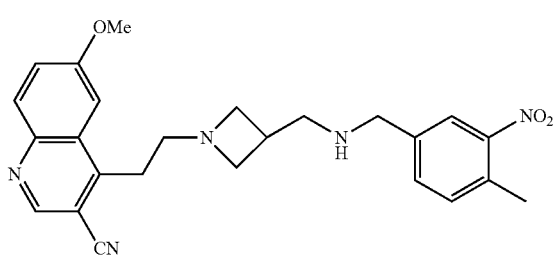 [SMILES: COc1ccc2ncc(C#N)c(CCN3CC(CNCc4ccc(C)c([N+](=O)[O-])c4)C3)c2c1]
VT-03-00084
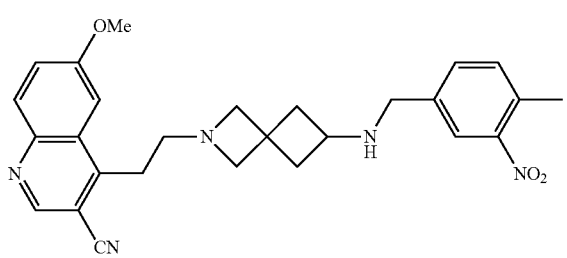 [SMILES: COc1ccc2ncc(C#N)c(CCN3CC4(CC(NCc5ccc(C)c([N+](=O)[O-])c5)C4)C3)c2c1]
VT-03-00085
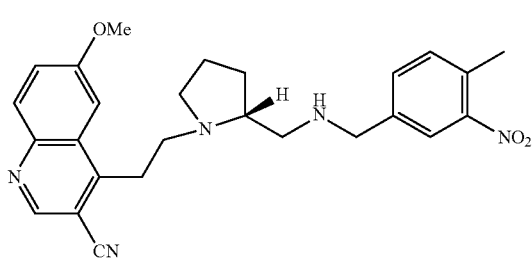 [SMILES: COc1ccc2ncc(C#N)c(CCN3CCC[C@@H]3CNCc3ccc(C)c([N+](=O)[O-])c3)c2c1]
VT-03-00086

TABLE I-continued
VT-03 Compounds of the Invention
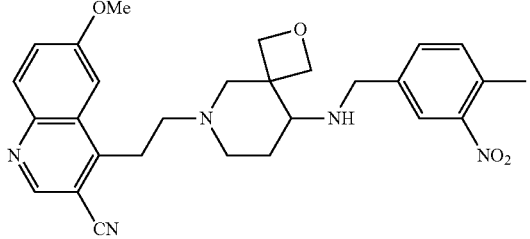 [SMILES: COc1ccc2ncc(C#N)c(CCN3CCC(NCc4ccc(C)c([N+](=O)[O-])c4)C4(COC4)C3)c2c1]
VT-03-00087
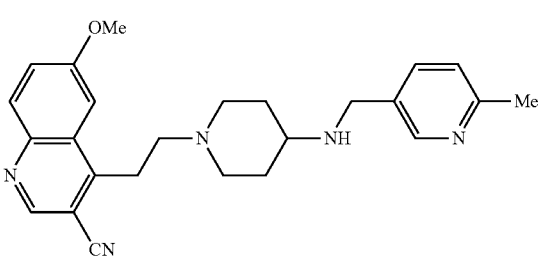 [SMILES: COc1ccc2ncc(C#N)c(CCN3CCC(NCc4ccc(C)nc4)CC3)c2c1]
VT-03-00088
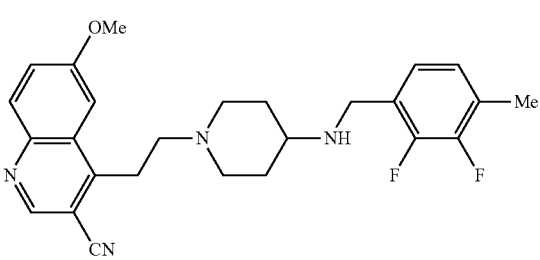
VT-03-00089
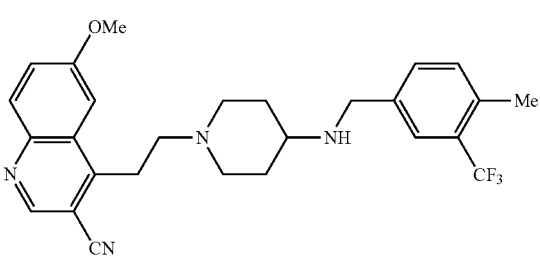 [SMILES: COc1ccc2ncc(C#N)c(CCN3CCC(NCc4ccc(C)c(C(F)(F)F)c4)CC3)c2c1]
VT-03-00090
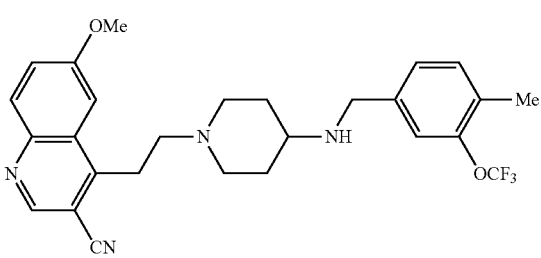 [SMILES: COc1ccc2ncc(C#N)c(CCN3CCC(NCc4ccc(C)c(OC(F)(F)F)c4)CC3)c2c1]
VT-03-00091
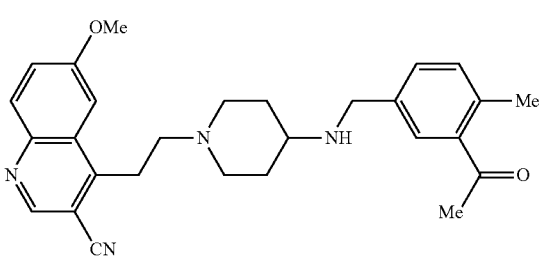 [SMILES: COc1ccc2ncc(C#N)c(CCN3CCC(NCc4ccc(C)c(C(C)=O)c4)CC3)c2c1]
VT-03-00092

TABLE I-continued
VT-03 Compounds of the Invention
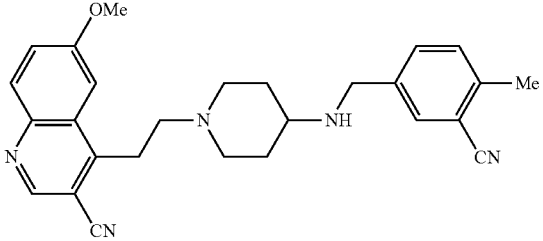 [SMILES: COc1ccc2ncc(C#N)c(CCN3CCC(NCc4ccc(C)c(C#N)c4)CC3)c2c1]
VT-03-00093
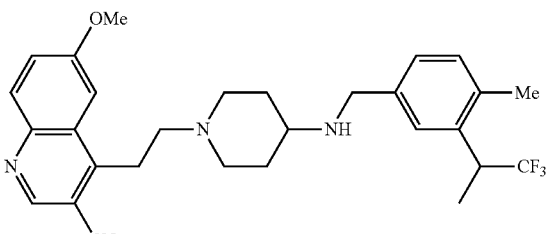
VT-03-00094
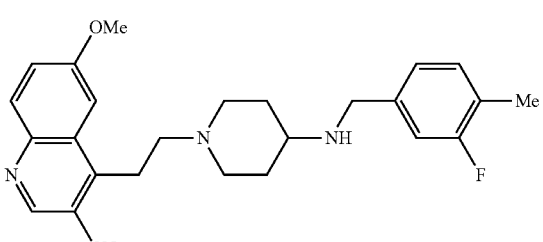
VT-03-00095
[3] GENERAL SYNTHESIS OF VT-03 COMPOUNDS OF THE INVENTION
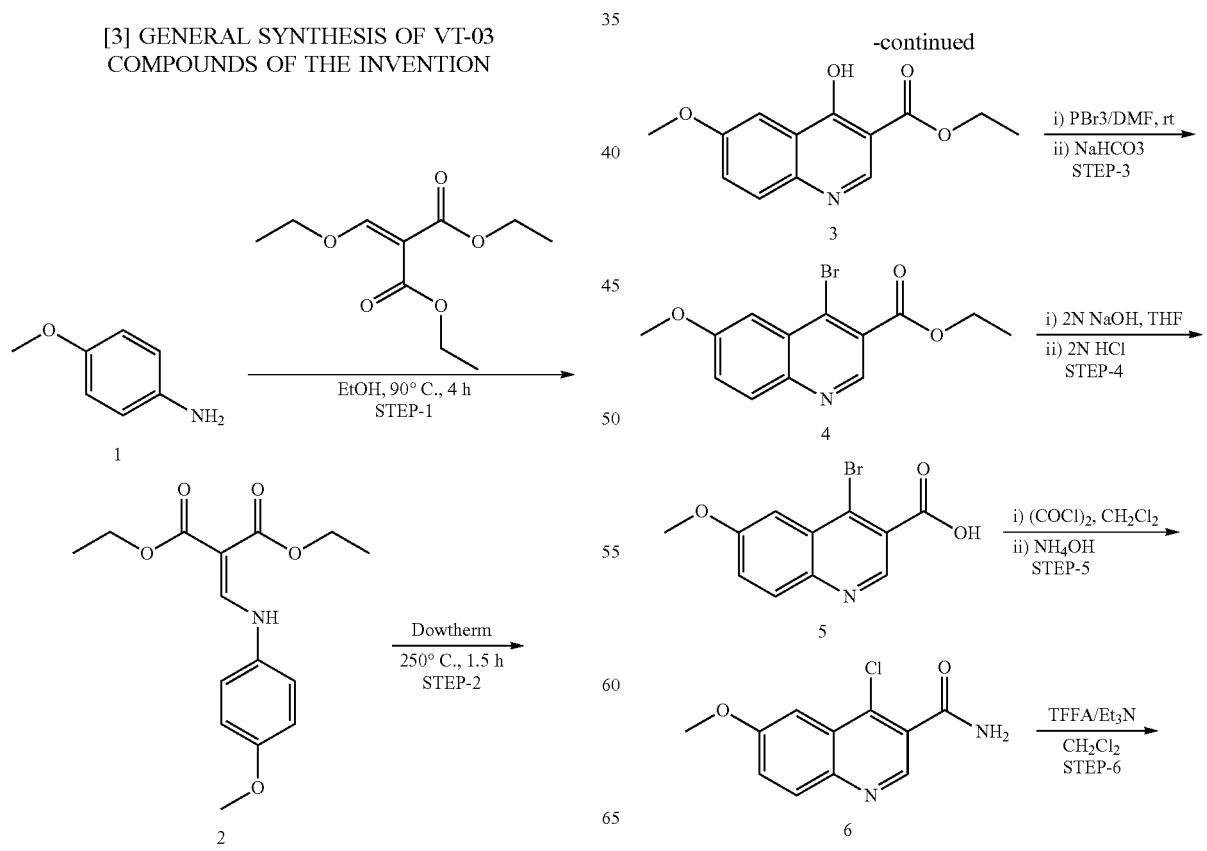

-continued

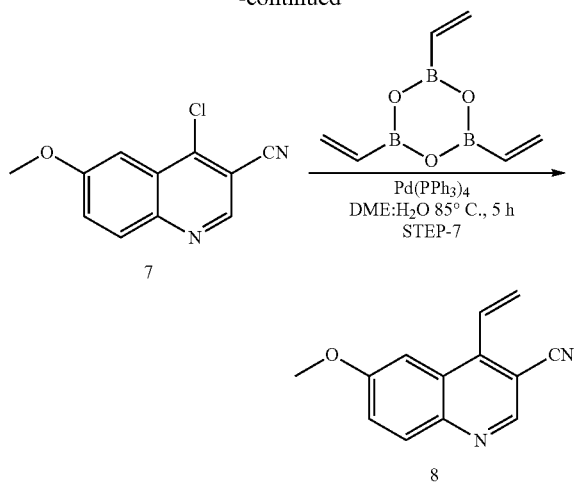

Preparation of
6-Methoxy-4-vinyl-quinoline-3-carbonitrile
(Compound of Step 8)

a) 2-[(4-Methoxy-phenylamino)-methylene]-malonic acid diethyl ester

To a solution of 4-aminoanisole (40 g, 324.8 mmol) in ethanol was added diethyl ethoxymethylenemalonate (70.23 g, 324.8 mmol). The reaction was refluxed at 85° C. for 4 h. The ethanol in the reaction mixture was distilled out under reduced pressure. The residue was chromatographed on silicagel eluting with 5% ethylacetate in hexane to afford the product as oil 2 (61 g).

b) 4-Hydroxy-6-methoxy-quinoline-3-carboxylic acid ethyl ester

Compound 2 (61 g) was taken up in dowtherm (400 ml) and heated at 250° C. for 3 h. The reaction mixture was cooled to (RT) and treated with pentane (300 mL) and filtered under suction. The resulting solids were washed thoroughly with excess of pentane and dried under vacuum to give 3 (23 g).

c) 4-Bromo-6-methoxy-quinoline-3-carboxylic acid ethyl ester

To a stirred solution of compound 3 (23 g, 93 mmol) in DMF (91 mL) was added $PBr_3$ (8.8 mL, 93 mmol) dropwise at RT. The reaction mixture was stirred at ambient temperature for 1 h after which 200 ml ice cold water was added. The reaction was neutralized with aq. $NaHCO_3$ solution. The obtained solids were collected by filtration, washed with water and dried under vacuum to give the required product 4 (32 g).

d) 4-Bromo-6-methoxy-quinoline-3-carboxylic acid

To a stirred solution of compound 4 (20 g) in THF was added 2N NaOH solution (71 mL) dropwise at 0° C. The reaction mixture was brought to RT and stirred for 24 h after which it was concentrated to remove the THF. The aqueous layer was washed with ethyl acetate to remove the insoluble impurities. The resulting aqueous layer was acidified to pH 2. The product was collected by filtration then codistilled with Toluene and dried under vacuum to afford the required compound 5 (15.5 g).

e) 4-Chloro-6-methoxy-quinoline-3-carboxylic acid amide

To a stirred solution of compound 5 (15 g, 53.4 mmol) in anhydrous dichloromethane (200 ml) was added oxalyl chloride (9.2 mL, 106.7 mmol) dropwise at 0° C. followed by the addition of a catalytic amount of dry DMF. The reaction mixture was gradually brought to RT and stirred for 1 h. The $CH_2Cl_2$ and oxalyl chloride in the reaction mass were removed by distillation. The residue obtained was redissolved in $CH_2Cl_2$, and conc.$NH_4OH$ solution (5 ml) was added dropwise very slowly to this solution at 0° C. (highly exothermic). The reaction was stirred for an additional 2 h. The observed solids were isolated via filtration, codistilled with Toluene and dried under vacuum to give the required compound 6 (22 g).

f) 4-Chloro-6-methoxy-quinoline-3-carbonitrile

To a stirred solution of compound 6 (26.5 g, 112.05 mmol) in $CH_2Cl_2$, was added triethylamine (104 ml) at 0° C. followed by dropwise addition of trifluoroacetic anhydride (59.6 mL, 425.9 mmol) at the same temperature. The reaction was stirred at RT for 3 h and quenched by adding water (150 mL). The organic layer was separated, dried over $Na_2SO_4$ and concentrated under reduced pressure. The obtained residue was treated with cold hexanes and filtered under suction to afford the required compound 7 (7.5 g).

g) 6-Methoxy-4-vinyl-quinoline-3-carbonitrile

To a stirred solution of compound 7 (3 g, 13.7 mmol) in 1,2-dimethoxyethane (90 mL) and water (30 mL) was added $K_2CO_3$ (14.9 mmol), $Pd(PPh_3)_4$ (0.274 mmol) and finally 2,4,6-trivinyl cycloborane-pyridine complex (14.9 mmol). The reaction was stirred at 80° C. for 6 h. The reaction mass was diluted with Ethyl acetate and filtered under celite. The filtrate was washed with water, dried over sodium sulfate and concentrated under reduced pressure. The obtained residue was chromatographed on silicagel eluting with 25% ethylacetate in hexanes to afford the product as a solid 8 (2.1 g).

[3] Synthesis of Specific Compounds of the Invention (1) Synthesis of VT-03-00014

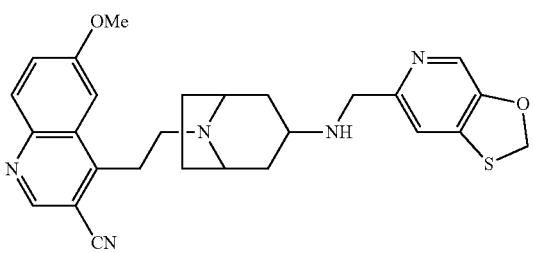 [SMILES: COc1ccc2ncc(C#N)c(CCN3C4CCC3CC(NCc3cc5c(cn3)OCS5)C4)c2c1]

(1a) 6-Methoxy-4-[2-(3-oxo-8-aza-bicyclo[3.2.1]oct-8-yl)-ethyl]-quinoline-3-carbonitrile To a stirred solution of 6-methoxy-4-vinyl-quinoline-3-carbonitrile (0.7 g, 3.32 mmol) in DMF (4 mL) was added nortropinone.hydrochloride (3.5 mmol) followed by dropwise addition of tetramethylguanidine (0.05 mL) at RT. The reaction was stirred at ambient temperature for 3 h.

The residue was concentrated under reduced pressure to remove the DMF and codistilled with toluene. The obtained residue was chromatographed on silica gel eluting with 2% MeOH in CH$_2$Cl$_2$ to afford the product (1 g).

(1b) 4-[2-(3-Amino-8-aza-bicyclo[3.2.1]oct-8-yl)-ethyl]-6-methoxy-quinoline-3-carbonitrile Compound 1 (a) (0.28 g, 0.837 mmol) was dissolved in saturated methanolic ammonia (6 mL) at 0° C. To it was added titanium isopropoxide (0.47 mL, 1.67 mmol) at 0° C. and the reaction mass was gradually brought to RT and stirred for 16 h at ambient temperature. NaBH$_4$ (47 mg, 1.25 mmol) was added portion wise and the reaction mass was stirred at RT for 2 h. The solvent was then completely distilled out under reduced pressure. The crude was acidified with 1N HCl and extracted with ethyl acetate to remove the insoluble impurities. The aqueous layer was then basified with 2N NaOH solution (pH 9) and extracted with 10% MeOH—CH$_2$Cl$_2$ solution and concentrated under reduced pressure to afford the required compound as a mixture (0.25 g). We proceeded with this mixture to the next step.

(1c) VT-03-00014

Compound 1 (b) (0.25 g) and [1,3]oxathiolo[5,4-c]pyridine-6-carbaldehyde (0.112 g) were taken in 1,2-dichloroethane (15 mL). To it was added sodium triacetoxy borohydride (0.188 g, 0.88 mmol) at 0° C., followed by a catalytic amount of acetic acid. The reaction mass was gradually brought to RT and stirred for 3 h. The DCE in the reaction was distilled out and the crude residue partitioned between water and 10% MeOH—CH$_2$Cl$_2$. The organic layer was dried over sodium sulphate and concentrated under reduced pressure. silicagel preparative TLC eluting with 5% MeOH—CH$_2$Cl$_2$ afforded the required compound (45 mg). LC-MS showed 93.3% purity. [M+H]+m/z 448.

(2) Synthesis of VT-03-00017

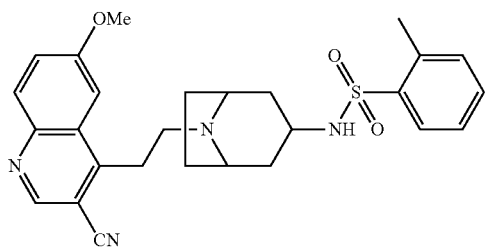 [SMILES: COc1ccc2ncc(C#N)c(CCN3C4CCC3CC(NS(=O)(=O)c3ccccc3C)C4)c2c1]

To a stirred solution of 4-[2-(3-amino-8-aza-bicyclo [3.2.1]oct-8-yl)-ethyl]-6-methoxy-quinoline-3-carbonitrile (0.25 g, 0.742 mmol) in dichloromethane (8 mL) was added triethyl amine (0.1 ml, 0.742 mmol). 2-methylbenzenesulfonyl chloride (0.155 g, 0.817 mmol) was added to the above solution at 0° C. The reaction mass was stirred at RT for 4 h. The solvents in the reaction mass were distilled out. The crude residue was purified by silicagel preparative TLC eluting with 10% MeOH—CH$_2$Cl$_2$ to give the required product (80 mg). $^1$HNMR (400 MHz, CDCl$_3$) δ 8.91 (s, 1H), 8.02 (d, 1H), 7.92 (d, 1H), 7.85 (s, 1H), 7.54 (dd, 2H), 7.38-7.42 (m, 2H), 4.01-4.08 (m, 6H), 3.39-3.42 (m, 1H), 3.18-3.21 (m, 2H), 2.91 (d, 2H), 2.69 (d, 4H), 2.51 (d, 2H), 2.36-2.40 (m, 2H), 2.09 (d, 2H), 2.01 (m, 1H). Mass spectra [M+H]+m/z 491.

(3) Synthesis of VT-03-00021

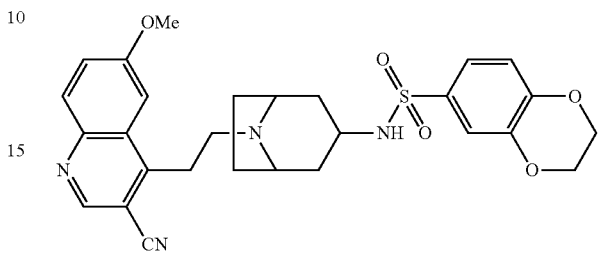

To a stirred solution of 4-[2-(3-amino-8-aza-bicyclo [3.2.1]oct-8-yl)-ethyl]-6-methoxy-quinoline-3-carbonitrile (0.08 g, 0.237 mmol) in dichloromethane (5 mL) was added triethyl amine (0.06 mL, 0.474 mmol). 1,4-benzodioxan-6-sulfonyl chloride (0.061 g, 0.260 mmol) dissolved in CH$_2$Cl$_2$ (2 mL) was added to the above solution at 0° C. The reaction mass was stirred at RT for 4 h. The solvents in the reaction mass were distilled out. The crude residue was purified by silicagel preparative TLC eluting with 10% MeOH—CH$_2$Cl$_2$ to give the required product (20 mg).
$^1$HNMR (400 MHz, CDCl$_3$) δ 8.79 (s, 1H), 8.05 (d, 1H), 7.52 (d, 1H), 7.23-7.46 (m, 3H), 6.92 (d, 1H), 4.46 (m, 1H), 4.31 (s, 4H), 3.98 (s, 3H), 3.45 (q, 3H), 3.25 (s, 2H), 2.95 (dd, 1H), 2.62 (t, 2H), 1.85-2.11 (m, 3H), 1.81 (d, 2H), 1.25 (s, 5H), 0.9 (d, 1H). Mass spectra [M+H]+m/z 535.1

(4) Synthesis of VT-03-00021a

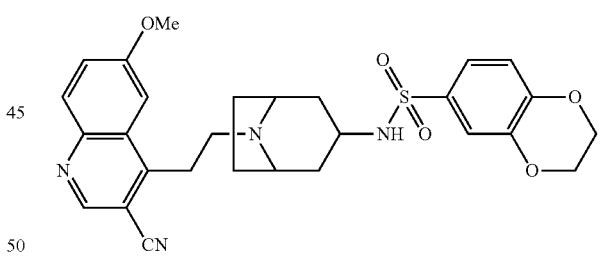

To a stirred solution of 4-[2-(3-amino-8-aza-bicyclo [3.2.1]oct-8-yl)-ethyl]-6-methoxy-quinoline-3-carbonitrile (0.15 g, 0.445 mmol) in 1,2-dichloromethane (8 mL) was added STAB (0.113 g, 0.534 mmol), 1,4-benzodioxan-6-carboxaldehyde (0.073 g, 0.445 mmol) and a catalytic amount of acetic acid. The reaction mass was stirred at RT for 4 h. The solvents in the reaction mass were distilled out. The crude residue was purified by silicagel preparative TLC eluting with 10% MeOH—CH$_2$Cl$_2$ to give the required product (18 mg).
$^1$HNMR (400 MHz, CDCl$_3$) δ 8.45 (s, 1H), 8.02 (d, 1H), 7.52 (d, 1H), 7.26 (s, 1H), 6.82 (d, 2H), 6.75 (d, 1H), 4.25 (s, 1H), 4.02 (s, 2H), 3.95 (s, 3H), 3.62 (s, 2H), 2.92 (t, 2H), 2.62 (t, 2H), 2.56 (d, 2H), 1.45 (s, 1H). Mass spectra [M+H]+m/z 485.

(5) Synthesis of VT-03-00022

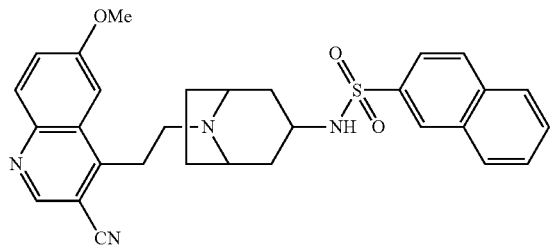 [SMILES: COc1ccc2ncc(C#N)c(CCN3C4CCC3CC(NS(=O)(=O)c3ccc5ccccc5c3)C4)c2c1]

To a stirred solution of 4-[2-(3-amino-8-aza-bicyclo[3.2.1]oct-8-yl)-ethyl]-6-methoxy-quinoline-3-carbonitrile (0.08 g, 0.237 mmol) in dichloromethane (5 mL) was added triethyl amine (0.06 mL, 0.474 mmol). (naphthalene-2-sulfonyl chloride 0.061 g, 0.260 mmol) dissolved in CH$_2$Cl$_2$ (2 mL) was added to the above solution at 0° C. The reaction mass was stirred at RT for 4 h. The solvents in the reaction mass were distilled out. The crude residue was purified by silicagel preparative TLC eluting with 10% MeOH—CH$_2$Cl$_2$ to give the required product (30 mg). Confirmed by mass spectra to be the product. Mass spectra [M+H]+m/z 527.2

(6) Synthesis of VT-03-00024

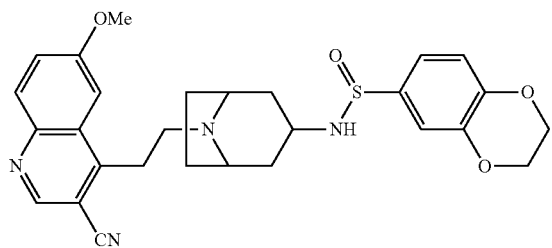 [SMILES: COc1ccc2ncc(C#N)c(CCN3C4CCC3CC(NS(=O)c3ccc5c(c3)OCCO5)C4)c2c1]

To a stirred solution of 4-[2-(3-amino-8-aza-bicyclo[3.2.1]oct-8-yl)-ethyl]-6-methoxy-quinoline-3-carbonitrile (0.17 g, 0.5 mmol) in CH$_2$Cl$_2$ was added triethylamine (0.18 mmol, 1.25 mL) at 0° C. under Nitrogen atmosphere. To it at 0° C. was added a solution of 2,3-dihydro-1,4-benzodioxine-6-carbonyl chloride (0.55 mmol) in CH$_2$Cl$_2$. The reaction mixture was gradually brought to RT and stirred for 2 h. Upon completion of the reaction the solvents were distilled out and the crude residue was partitioned between water and 10% MeOH—CH$_2$Cl$_2$. The organic layers were dried over sodium sulphate and concentrated under reduced pressure. The residue was purified by silicagel preparative TLC eluting with 2% MeOH—CH$_2$Cl$_2$ to afford the required compound (25 mg).

$^1$HNMR (400 MHz, CDCl$_3$) δ 8.85 (s, 1H), 8.02 (d, 1H), 7.52 (d, 1H), 7.46 (s, 1H), 7.25 (s, 1H), 6.92 (d, 1H), 6.35 (s, 1H), 4.35 (s, 5H), 4.09 (s, 3H), 3.52 (s, 2H), 3.24 (t, 2H), 2.75 (t, 2H), 2.25 (d, 2H), 2.12 (d, 2H), 1.74-1.92 (m, 5H), 1.75 (d, 3H), 1.25 (s, 2H). Mass spectra [M+H]+m/z 499.2

(7) Synthesis of VT-03-00026

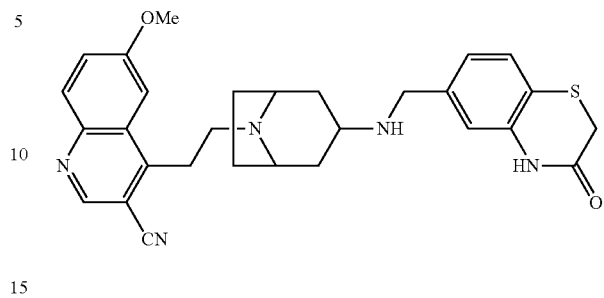

(7a) (4-Acetoxymethyl-2-nitro-phenylsulfanyl)-acetic acid ethyl ester

NaH (60%) was taken in a 100 mL 2-neck RB flask. To it was added ethyl-2-mercaptoacetate (0.7, 5.86 mmol) dissolved in dioxan (15 mL) at 0° C. The reaction mixture solidified and so was brought to RT and stirred for 2 h. Acetic acid 4-fluoro-3-nitro-benzyl ester (1.15 g, 5.33 mmol) dissolved in 1,4-dioxane (10 mL) was then added dropwise and stirred overnight at RT. Upon completion of the reaction water was added to it and extracted with CH$_2$Cl$_2$. The organic layers were dried over sodium sulphate and concentrated under reduced pressure. The obtained residue was chromatographed on silicagel eluting with 32% EtOAc in Hexanes to afford the required compound (0.74 g).

(7b) Acetic acid 3-oxo-3,4-dihydro-2H-benzo[1,4]thiazin-6-ylmethyl ester

To a stirred solution of (4-acetoxymethyl-2-nitro-phenylsulfanyl)-acetic acid ethyl ester (0.75 g, 2.4 mmol) in glacial acetic acid (20 mL) was added Iron powder (1.23 g) and heated at 60° C. for 1 h. Upon completion of the reaction the AcOH in the reaction was distilled out. The crude was partitioned between EtOAC and water. The organic layers were dried over Na$_2$SO$_4$ and concentrated under reduced pressure. The obtained residue was chromatographed on silicagel eluting with 50% EtOAc in hexanes to afford the required compound (0.38 g).

(7c) 6-Hydroxymethyl-4H-benzo[1,4]thiazin-3-one

To a stirred solution of acetic acid 3-oxo-3,4-dihydro-2H-benzo[1,4]thiazin-6-ylmethyl ester (0.38 g, 1.6 mmol) in MeOH (15 mL) was added Lithium hydroxide Monohydrate and stirred for 3 h. Upon completion of the reaction the excess MeOH was distilled out. The crude was acidified with 2N HCl and extracted with EtOAC. The organic layers were dried over Sodium sulfate and concentrated under reduced pressure to afford the product as a pale brown solid (0.28 g).

(7d) 3-Oxo-3,4-dihydro-2H-benzo[1,4]thiazine-6-carbaldehyde

To a stirred solution of dess martin periodinane (0.66 g, 1.6 mmol) in CH$_2$Cl$_2$ (5 mL) was added a solution of 6-hydroxymethyl-4H-benzo[1,4]thiazin-3-one (0.28 g, 1.43 mmol) dropwise at 0° C. The reaction was stirred at RT for 1 h. Upon completion, the reaction was quenched with saturated NaHCO$_3$ solution and extracted with CH$_2$Cl$_2$. The CH$_2$Cl$_2$ layers were dried over sodium sulfate and concentrated under reduced pressure to afford the required product 33 as an off white solid (0.23 g).

(7e) VT-03-00026

To a stirred solution of compound (7d) (0.172 g, 0.891 mmol) in 1,2-dichloroethane (5 mL) was added compound (1b) (0.3 g, 0.89 mmol), sodium triacetoxy borohydride (0.23 g, 1.07 mmol), and catalytic amount of acetic acid. The reaction was stirred for 13 h at RT. The reaction mass was concentrated to remove the solvents. The resulting crude was partitioned between 10% MeOH—CH$_2$Cl$_2$ and water. The organic layer was dried over sodium sulphate and concentrated under reduced pressure. The residue was purified by silicagel preparative TLC eluting with 3% MeOH—CH$_2$Cl$_2$ to afford the required compound VT-03-00026 (15 mg).

$^1$HNMR (400 MHz, CDCl$_3$) δ 8.85 (s, 1H), 8.08 (d, 1H), 7.52 (s, 1H), 7.50 (s, 1H), 7.25 (s, 1H), 6.95 (d, 1H), 6.75-6.85 (m, 1H), 4.02 (s, 3H), 3.70 (s, 2H), 3.51 (s, 2H), 3.47 (s, 2H), 3.39 (d, 1H), 2.85 (m, 1H), 2.75 (t, 2H), 2.12 (t, 2H), 1.45 (s, 2H), 1.25 (s, 2H), 0.9 (d, 1H). Mass spectra [M+H]+m/z 514.3

(8) Synthesis of VT-03-00026a

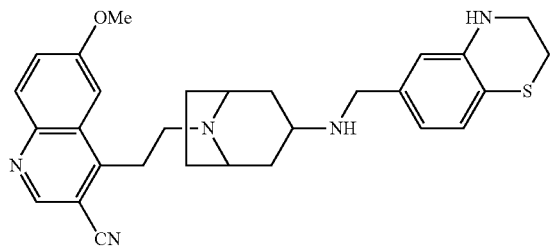 [SMILES: COc1ccc2ncc(C#N)c(CCN3C4CCC3CC(NCc3ccc5c(c3)NCCS5)C4)c2c1]

(8a)
(3,4-Dihydro-2H-benzo[1,4]thiazin-6-yl)-methanol

To a stirred solution lithium aluminium hydride (0.28 g, 7.4 mmol) in THF (8 mL), was added dropwise, a solution of compound 7b (0.7 g, 2.95 mmol) in THF. The reaction was refluxed at 85° C. for 3 h. Upon completion of the reaction, the reaction was quenched with ice cold water, followed by 1.3N NaOH solution (10 mL) and extracted with ethyl acetate. The EtOAc layers were dried over sodium sulfate and concentrated under reduced pressure. The obtained residue was chromatographed on silicagel eluting with 80% EtOAc in hexanes to afford the required compound (0.28 g).

(8b)
(3,4-Dihydro-2H-benzo[1,4]thiazine-6-carbaldehyde

To a stirred solution of dess martin periodinane (0.286 g, 0.67 mmol) in CH$_2$Cl$_2$ (4 ml), was added dropwise, a solution of compound 8a (0.12 g, 0.6 mmol) in CH$_2$Cl$_2$ (4 ml). The reaction was stirred for 1 h at RT. The reaction was quenched with 1.3M NaOH solution (5 ml), then with water and extracted with diethyl ether. The ether layers were dried over sodium sulphate and concentrated under reduced pressure to afford the required compound as a mixture (55 mg). Proceeded to the next step with crude.

(8c) VT-03-00026a

To a stirred solution of compound 8b (53 mg, 0.29 mmol) in 1,2-dichloroethane (5 mL) was added compound 1b (0.1 g, 0.29 mmol), sodium triacetoxy borohydride (73 mg, 0.348 mmol), and catalytic amount of acetic acid. The reaction was stirred for 3 h at RT and then at 60° C. for another 3 h. The reaction mass was concentrated to remove the solvents. The resulting crude was partitioned between 10% MeOH—CH$_2$Cl$_2$ and water. The organic layer was dried over sodium sulphate and concentrated under reduced pressure. The residue was purified by silicagel preparative TLC eluting with 3% MeOH—CH$_2$Cl$_2$ to afford the required compound (10 mg).

Mass spectra [M+H]+m/z 500.3

(9) Synthesis of VT-03-00027

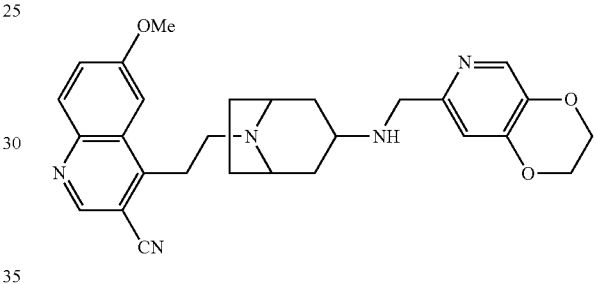

(9a) 5-Benzyloxy-2-hydroxymethyl-pyran-4-one

To a stirred solution of kojic acid (5 g, 35.19 mmol) in methanol (35 mL) was added benzyl bromide (4.7 mL, 38.7 mmol) dropwise at RT. The reaction mass was heated at 100° c. for 5 h. The methanol in the reaction mass was distilled out. The resulting crude solids were treated with a mixture 60 ml water and 6 ml acetone and filtered under suction. The obtained solids were dried under high vacuum at 60° C. for 1 h to afford the required compound (5.5 g).

(9b)
5-Benzyloxy-2-hydroxymethyl-1H-pyridin-4-one

To a stirred solution of compound 9a (5.2 g) in ethanol (15 mL), was added conc NH$_4$OH solution and heated in a sealed tube at 90° c. for 16 h. The obtained solids were filtered under suction and washed with cold hexanes and oven dried under vacuum. 2.7 g of the required compound was obtained.

(9c) 5-Hydroxy-2-hydroxymethyl-1H-pyridin-4-one

To a stirred solution of compound 9b (2.7 g) in NaOH solution (0.567 g in 55 mL of water) was added 10% Pd—C (1.4 g) portion wise under nitrogen atmosphere. The nitrogen was replaced with hydrogen and stirred at RT for 16 h. The reaction mass was filtered under celite and concentrated under reduced pressure to give 2.2 g of the required compound as a mixture.

Proceeded with crude to the next step.

(9d) (2,3-Dihydro-[1.4]dioxino[2,3-c]pyridin-7-yl)-methanol

To a stirred solution of compound 9c (2.2 g) in DMF was added $K_2CO_3$ (4.9 g, 39 mmol) and 1.6 ml (18.7 mmol) of 1,2-dibromoethane at RT. The reaction was heated at 80° C. for 16 h. The DMF in the reaction mass was distilled out. The crude was diluted with water and extracted with 5% $MeOH$—$CH_2Cl_2$ solution. The organic layers were dried over $Na_2SO_4$ and concentrated under reduced pressure to give the required compound as a mixture (0.45 g). Proceeded to the next step without further purification.

(9e) 2,3-Dihydro-[1.4]dioxino[2,3-c]pyridine-7-carbaldehyde

To a stirred solution of dess martin periodinane (1.3 g, 2.96 mmol) in $CH_2Cl_2$ (8 ml), was added dropwise, a solution of compound 9d (0.45 g, 2.7 mmol) in $CH_2Cl_2$ (8 ml). The reaction was stirred for 1 h at RT. The reaction was quenched with 1.3M NaOH solution (5 ml), then with water and extracted with diethyl ether. The ether layers were dried over sodium sulphate and concentrated under reduced pressure to afford the required compound as a mixture (0.4 g). Proceeded to the next step with crude.

(9f) VT-03-00027

To a stirred solution of compound 1b (0.16 g, 0.499 mmol) in 1,2-dichloromethane (8 ml) was added STAB (0.126 g, 0.598 mmol), compound 9e (0.082 g, 0.499 mmol) and a catalytic amount of acetic acid. The reaction mass was stirred at RT for 4 h. The solvents in the reaction mass were distilled out. The crude residue was purified by silicagel preparative TLC eluting with 10% $MeOH$—$CH_2Cl_2$ to give the required product (5 mg).
$^1$HNMR (400 MHz, $CDCl_3$) δ 8.75 (s, 1H), 8.05 (d, 2H), 7.51 (s, 1H), 7.25 (d, 1H), 6.75 (s, 1H), 4.35 (d, 4H), 4.03 (s, 3H), 3.92 (s, 2H), 3.75 (s, 4H), 3.02-3.04 (m, 1H), 2.02-2.36 (m, 4H), 1.25 (t, 3H), 0.75-0.92 (m, 3H). Mass spectra [M+H]+m/z 486.5

(10) Synthesis of VT-03-00028

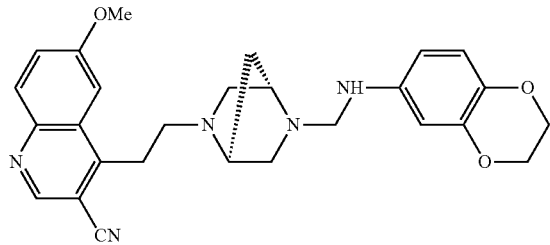 [SMILES: COc1ccc2ncc(C#N)c(CCN3C[C@@H]4C[C@H]3CN4CNc3ccc4c(c3)OCCO4)c2c1]

(10a) 5-[2-(3-Cyano-6-methoxy-quinolin-4-yl)-ethyl]-2,5-diaza-bicyclo[2.2.1]heptane-2-carboxylic acid tert-butyl ester To a stirred solution of 6-methoxy-4-vinyl-quinoline-3-carbonitrile (0.20 g, 1.18 mmol) and (1S,4S)-2-Boc-2,5diazabicyclo[2.2.1]heptane (0.24 g, 1.43 mmol) in DMF (5 ml) was added tetramethyl guanidine (0.06 ml) at RT and stirred for 5 h. Upon completion the DMF in the reaction was distilled out. The residue was chromatographed on silicagel and eluted the required compound with 10% MeOH in $CH_2Cl_2$ as an off-white solid (0.32 g).

(10b) 4-[2-(2,5-Diaza-bicyclo[2.2.1]hept-2-yl)-ethyl]-6-methoxy-quinoline-3-carbonitrile To a stirred solution of compound 10a (0.32 g) in $CH_2Cl_2$ (8 ml) was added 4M HCl in dioxan (3 ml) dropwise at 0° C. The reaction was stirred at RT for 16 h. Upon completion the solvents in the reaction were distilled out. The crude was basified with 2N NaOH solution and extracted with 10% MeOH in $CH_2Cl_2$ to afford the required compound as a greenish viscous material (0.4 g crude).

(10c) VT-03-00028

To a stirred solution of compound 10b (0.4 g, 1.2 mmol) in 1,2-dichloroethane was added 1,4-benzodioxan-6-carboxaldehyde (0.21 g, 1.2 mmol), sodium triacetoxy borohydride (1.4 mmol) and a catalytic amount of AcOH and stirred at RT for 16 h. Upon completion the solvent in the reaction was distilled out. The crude was partitioned between water and 5% $MeOH$—$CH_2Cl_2$. The organic layers were dried over sodium sulphate and concentrated under reduced pressure. The residue was purified by silicagel preparative TLC eluting with 6% $MeOH$—$CH_2Cl_2$ to afford the required compound VT-03-00028 (15 mg).
$^1$HNMR (400 MHz, $CDCl_3$) δ 8.85 (s, 1H), 8.02 (d, 1H), 7.52 (d, 1H), 7.32-7.36 (m, 1H), 6.98 (s, 1H), 6.79 (s, 2H), 4.25 (s, 4H), 3.98 (s, 3H). 3.61 (d, 2H), 3.31-3.47 (m, 4H), 2.62-3.14 (m, 6H), 1.54 (s, 6H), 0.92 (t, 2H). Mass spectra [M+H]+m/z 472.5

(11) Synthesis of VT-03-00030

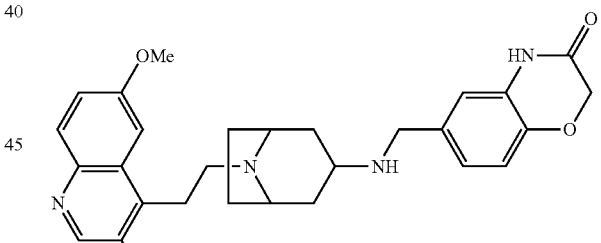

(11a) (4-Formyl-2-nitro-phenoxy)-acetic acid ethyl ester

To a stirred solution of 4-hydroxy-3-nitro-benzaldehyde (5.0 g, 29.9 mmol) in acetonitrile (125 ml) was added ethyl bromoacetate (4.9 ml, 44.9 mmol) and heated at 95° C. for 16 h. Upon completion of the reaction, the acetonitrile in the reaction was distilled out. The crude was partitioned water and $CH_2Cl_2$. The organic layer was dried over sodium sulphate and concentrated under reduced pressure. The obtained residue was purified by column chromatography (60-120 mesh silica-gel) which eluted the required compound with 25% EtOAc-hexanes as an off white solid (2.1 g).

(11b) 3-Oxo-3,4-dihydro-2H-benzo[1,4]oxazine-6-carbaldehyde

To a stirred solution of compound 11a (1.7 g, 6.6 mmol) in acetic acid (50 ml) was added Iron powder (3.7 g, 66 mmol) and heated at 80° C. for 3 h. Upon completion of the reaction, the acetic acid in the reaction was distilled out. The crude was basified to pH~9 in ice cold water and filtered under celite. The filtrate was extracted with EtOAC. The organic layers were dried over sodium sulphate and concentrated under reduced pressure. The obtained residue was purified by column chromatography (60-120 mesh silicagel) which eluted the required compound with 55% EtOAC-hexanes as a white solid (0.7 g).

(11c) VT-03-00030

To a stirred solution of compound 11b (0.15 g, 0.445 mmol) and compound 1b (0.078 g, 0.445 mmol) in 1,2-dichloroethane was added sodium triacetoxyborohydride and stirred at RT for 5 h. Upon completion the dichloroethane in the reaction was distilled out. The crude was partitioned between water and 10% MeOH—CH$_2$Cl$_2$. The organic layers were dried over sodium sulphate and concentrated under reduced pressure. The obtained residue was purified by preparative TLC which eluted the required compound with 7% MeOH in CH$_2$Cl$_2$ as an yellow solid (0.02 g).

$^1$HNMR (400 MHz, CDCl$_3$) δ 8.85 (s, 1H), 8.02 (d, 1H), 7.75-7.85 (m, 1H), 7.52 (d, 1H), 6.82 (d, 2H), 6.72 (s, 1H), 4.53 (s, 2H), 3.98-4.03 (m, 3H), 3.75 (s, 3H), 3.62 (s, 2H), 3.23-3.26 (m, 1H), 2.75 (m, 2H), 2.06 (m, 4H), 1.25 (m, 5H). Mass spectra [M+H]+m/z 499.2

(12) Synthesis of VT-03-00031

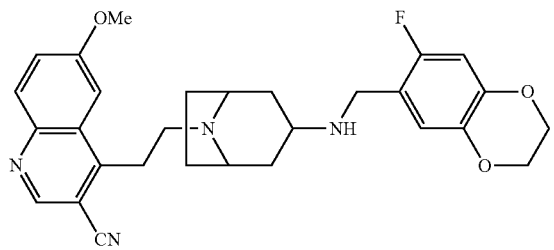 [SMILES: COc1ccc2ncc(C#N)c(CCN3C4CCC3CC(NCc3cc5c(cc3F)OCCO5)C4)c2c1]

(12a) 2-Fluoro-4,5-dihydroxy-benzaldehyde

To a stirred solution of 2-fluoro-4,5-dimethoxy-benzaldehyde (0.177 g, 0.96 mmol) in CH$_2$Cl$_2$ (13 ml) was added boron tribromide (0.96 ml, 9.6 mmol) dropwise at 0° C. The reaction was gradually brought to RT and stirred for 4 h. Upon completion the reaction mixture was poured into ice and extracted with CH$_2$Cl$_2$. The CH$_2$Cl$_2$ layer was dried over Sodium sulfate and concentrated under reduced pressure to afford the required product as a red viscous material (0.25 g crude).

(12b) 7-Fluoro-2,3-dihydro-benzo[1.4]dioxine-6-carbaldehyde

To a stirred solution of compound 12a (0.35 g, 2.24 mmol) in DMF (15 ml) was added 1,2-dibromoethane (0.463 g, 0.21 ml) and potassium carbonate (0.77 g, 5.6 mmol) and heated at 80° C. for 4 h. The reaction mass was quenched with ice cold water and extracted with EtOAC. The EtOAc layers were dried over sodium sulphate and concentrated under reduced pressure. The obtained residue was chromatographed on silicagel eluting with 16% EtOAc in Hexanes to afford the required compound 36 (0.15 g).

(12c) VT-03-00031

To a stirred solution of compound 1b (0.22 g, 0.653 mmol) in 1,2-dichloroethane was added compound 12b (0.118 g, 0.653 mmol), followed by sodium triacetoxy borohydride (0.166 g, 0.783 mmol) and catalytic acetic acid at 0° C. The reaction was brought to RT and stirred for 4 h. Upon completion the solvent in the reaction was distilled out. The crude was partitioned between water and 5% MeOH—CH$_2$Cl$_2$. The organic layers were dried over sodium sulphate and concentrated under reduced pressure. The residue was purified by silicagel preparative TLC eluting with 5% MeOH—CH$_2$Cl$_2$ to afford the required compound VT-03-00031 (18 mg).

$^1$HNMR (400 MHz, CDCl$_3$) δ 8.81 (s, 1H), 8.05 (d, 1H), 7.52 (d, 1H), 7.42 (s, 1H), 6.75 (s, 1H), 6.53 (d, 1H), 4.25 (s, 4H), 3.96 (s, 3H), 3.61 (s, 2H), 3.46 (t, 2H), 3.39 (t, 1H), 2.95 (s, 1H), 2.75 (t, 2H), 2.05-2.10 (m, 5H), 1.24 (s, 6H), 0.92 (s, 1H). Mass spectra [M+H]+m/z 503.3

(13) Synthesis of VT-03-00032

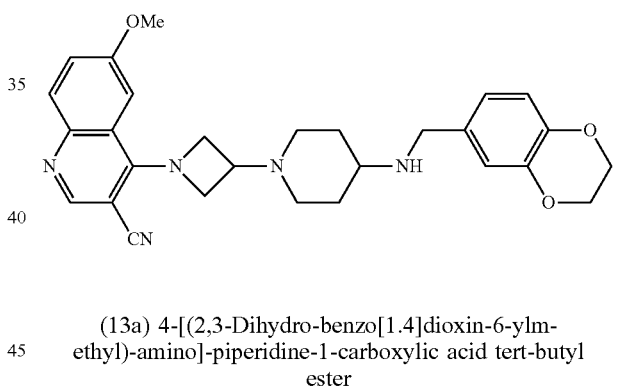

(13a) 4-[(2,3-Dihydro-benzo[1.4]dioxin-6-ylm-ethyl)-amino]-piperidine-1-carboxylic acid tert-butyl ester To a stirred solution of 4-amino-piperidine-1-carboxylic acid tert-butyl ester (1 g, 5 mmol) and 2,3-dihydro-benzo[1,4]dioxine-6-carbaldehyde (0.82 g, 5 mmol) in 1,2-dichloroethane (10 ml) was added sodium triacetoxy borohydride (1.59 g, 7.5 mmol) and a catalytic amount of AcOH. The reaction was stirred at RT for 8 h. Upon completion, the solvent in the reaction was removed and the crude partitioned between water and 5% MeOH in CH$_2$Cl$_2$. The organic layers were dried over Sodium sulfate and concentrated under reduced pressure to afford the product 40 as an yellow solid (1 g).

(13b) (2,3-Dihydro-benzo[1.4]dioxin-6-ylmethyl)-piperidin-4-yl-amine

To a stirred solution of compound 13a in CH$_2$Cl$_2$ was added a solution of 4M HCl in dioxan at 0° C. The reaction was stirred at RT for 4 h. The solvent in the reaction was distilled out to afford the required compound 41 as an hydrochloric salt (0.75 g).

(13c) 3-{4-[(2,3-Dihydro-benzo[1.4]dioxin-6-ylmethyl)-amino]-piperidin-1-yl}-azetidine-1-carboxylic acid tert-butyl ester To a stirred solution of compound 13b (1 g, 4 mmol) in ethanol (10 ml) was added triethyl amine (2 ml) and stirred for 10 min at RT. Then 1-N-Boc-3-Azetidinone (0.827 g, 4.83 mmol) was added followed by titanium isopropoxide (2.29 g, 8 mmol) at 0° C. The reaction was stirred at RT for 16 h. Then sodium borohydride (0.29 g, 8 mmol) was added and stirred at RT for 8 h. Upon completion, the reaction was quenched with ice and extracted with EtOAc. The organic layers were dried over Sodium sulfate and concentrated under reduced pressure. The residue was chromatographed on silica gel to elute the required compound with 6% MeOH in CHCl$_3$ as an yellow solid (0.75 g).

(13d) (1-Azetidin-3-yl-piperidin-4-yl)-(2,3-dihydro-benzo[1.4]dioxin-6-ylmethyl)-amine To a stirred solution of compound 13c (0.75 g) in CH$_2$Cl$_2$ (5 ml) was added 4M HCl in dioxan (7.5 ml) at 0° C. The reaction was stirred at RT for 4 h. Upon completion, the solvents in the reaction were distilled out to afford the required product, as a yellow crude hydrochloric salt (0.5 g).

(13e) VT-03-00032

To a stirred solution of compound 13d (0.2 g, 0.66 mmol) in DMF (2 ml) was added K$_2$CO$_3$ (0.182 g, 1.32 mmol) and 4-Chloro-6-methoxy-quinoline-3-carbonitrile (0.173 g, 0.66 mmol) and heated at 80° C. for 3 h. Upon completion, the DMF in the reaction was distilled out. The crude was partitioned between water and EtOAC. The EtOAc layers were dried over sodium sulphate and concentrated under reduced pressure. The crude residue was chromatographed on silica gel and eluted the required compound with 5% MeOH in CH$_2$Cl$_2$ as a off white solid (20 mg).
$^1$HNMR (400 MHz, CDCl$_3$) δ 8.46 (s, 1H), 7.91 (d, 1H), 7.21-7.41 (m, 3H), 6.92 (s, 1H), 6.90 (d, 1H), 4.82 (t, 2H), 4.62 (t, 2H), 4.20 (s, 4H), 3.83 (s, 3H), 3.67 (s, 2H), 3.30-3.32 (m, 1H), 2.80 (d, 2H), 2.60- 2.61 (m, 1H), 1.52 (d, 2H). Mass spectra [M+H]+m/z 486.4

(14) Synthesis of VT-03-00042

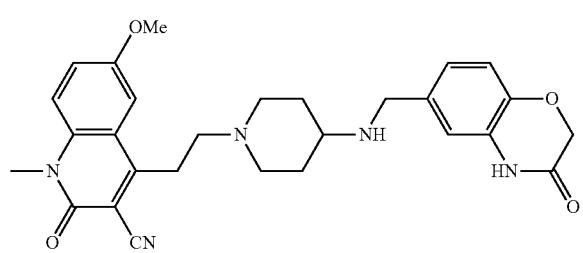 [SMILES: COc1ccc2c(c1)c(CCN1CCC(NCc3ccc4c(c3)NC(=O)CO4)CC1)c(C#N)c(=O)n2C]

(14a)
6-Hydroxy-1H-benzo[d][1,3]oxazine-2,4-dione

To a stirred solution of 5-hydroxy anthranilic acid (5 g, 29.94 mmol) in 1,4-dioxane (50 ml) was added triphosgene (6.2 g, 20.96 mmol) and heated to reflux for 4 h. Upon completion 20 ml of water was added to the reaction and the obtained solids were filtered. These solids were then washed with diethyl ether and dried under vacuum to afford the required product as a pale brown solid (10 g).

(14b) 6-Methoxy-1-methyl-1H-benzo[d][1,3]oxazine-2,4-dione

To a stirred solution of compound 14a (5.1 g, 25.9 mmol) in DMF (45 ml) was added potassium carbonate (5.4 g, 38.9 mmol). To this solution was added at 0° C., methyl Iodide (2.5 ml, 38.9 mmol) and stirred at RT for 18 h. Upon completion, the reaction was quenched with ice and the solids thus obtained were filtered under suction. These solids were codistilled with toluene (100 ml) to remove any traces of water, to afford the required compound as a white solid (4.2 g).

(14c) 4-Hydroxy-6-methoxy-1-methyl-2-oxo-1,2-dihydro-quinoline-3-carbonitrile To a stirred solution of Compound 14b (1.0 g, 4.83 mmol) in DMF (10 ml) was added 60% sodiumhydride (0.173 g, 7.3 mmol) followed by ethylcyanoacetate (0.66 g, 5.8 mmol) at RT. The reaction was heated at 150° C. with stirring for 24 h. Upon completion, the reaction was quenched with ice and stirred at RT for 1 h. The obtained solids were filtered under suction. These solids were further washed with diethyl ether and then dried under vacuum to afford the required compound as a black solid (0.8 g).

(14d) 4-Chloro-6-methoxy-1-methyl-2-oxo-1,2-dihydro-quinoline-3-carbonitrile A stirred solution of compound 14c (1 g, 4.34 mmol) in POCl$_3$ (10 ml) was heated at 100° C. and stirred for 6 h. Upon completion, the reaction mass was poured into ice (100 ml). This aqueous layer was extracted with ethyl acetate (100 ml) and the organic later was dried over sodium sulphate and concentrated under reduced pressure. Column chromatography eluted the required compound with 20% ethyl acetate-CH$_2$Cl$_2$ as a yellow solid (0.1 g).

(14e) 6-Methoxy-1-methyl-2-oxo-4-vinyl-1,2-dihydro-quinoline-3-carbonitrile

To a stirred solution of compound 14d (0.1 g, 13.7 mmol) in 1,2-dimethoxyethane (1 ml) and water (0.3 ml) was added K$_2$CO$_3$ (0.11 g, 0.8 mmol), Pd(PPh$_3$)$_4$ (0.05 mol %) and finally 2,4,6-trivinyl cycloborane-pyridine complex (0.116 g, 0.48 mmol). The reaction was stirred at 80° C. for 6 h. The reaction mass was diluted with Ethyl acetate and filtered under celite. The filterate was washed with water, dried over Sodium sulfate and concentrated under reduced pressure. The obtained residue was chromatographed on silicagel eluting with 25% ethylacetate in hexanes to afford the product as a solid (0.02 g).

(14f) 4-[(3-Oxo-3,4-dihydro-2H-benzo[1.4]oxazin-6-ylmethyl)-amino]-piperidine-1-carboxylic acid tert-butyl ester To a stirred solution of 4-Amino-piperidine-1-carboxylic acid tert-butyl ester (1 g, 5 mmol) and 3-Oxo-3,4-dihydro-2H-benzo[1,4]oxazine-6-carbaldehyde (0.82 g, 5 mmol) in 1,2-DCE (10 ml) was added sodium triacetoxy borohydride (1.59 g, 7.5 mmol) and a catalytic amount of AcOH. The reaction was stirred at RT for 8 h. Upon completion, the solvent in the reaction was removed and the crude partitioned between water and 5% MeOH in CH$_2$Cl$_2$. The organic layers were dried over sodium sulfate and concentrated under reduced pressure to afford the product 40 as an pale yellow solid (1 g).

(14 g) 6-(Piperidin-4-ylaminomethyl)-4H-benzo[1, 4]oxazin-3-one

To a stirred solution of compound 14f (1 g) in CH$_2$Cl$_2$ was added a solution of 4M HCl in dioxane (2 ml) at 0° C. The reaction was stirred at RT for 4 h. The solvent in the reaction was distilled out to afford the required compound as an hydrochloric salt (0.75 g).

(14 h) VT-03-00042

To a stirred solution of Compound 14e (0.04 g, 0.166 mmol) and Compound 14 g (0.0479 g, 0.183 mmol) in DMF (2 ml) was added tetramethyl guanidine (0.009 ml). The reaction was stirred at RT for 3 h. Upon completion, the DMF in the reaction mass was distilled out. The crude was diluted with 10% MeOH—CH$_2$Cl$_2$ and washed with water and concentrated under reduced pressure. The obtained crude was purified by preparative TLC to afford the required compound as an off-white solid (0.010 g).

$^1$HNMR (400 MHz, DMSO-d6) δ 10.6 (s, 1H), 7.89 (d, 1H), 7.58 (d, 1H) 7.46 (dd, 1H), 6.83 (d, 3H), 4.52 (s, 2H), 3.82 (s, 6H), 3.65 (s, 2H), 3.15 (t, 2H), 2.87 (s, 2H), 2.67 (d, 2H), 2.08 (t, 2H), 1.85 (d, 2H), 1.26 (s, 2H), 1.22 (s, 2H). Mass spectra [M+H]+m/z 502.4

(15) Synthesis of VT-03-00043

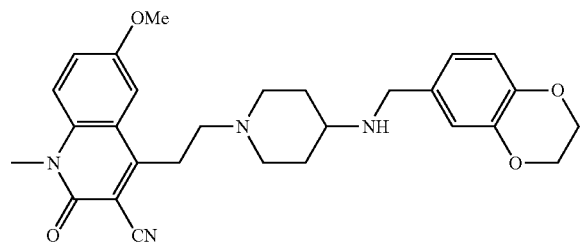 [SMILES: COc1ccc2c(c1)c(CCN1CCC(NCc3ccc4c(c3)OCCO4)CC1)c(C#N)c(=O)n2C]

(15a) {1-[2-(3-Cyano-6-methoxy-1-methyl-2-oxo-1, 2-dihydro-quinolin-4-yl)-ethyl]-piperidin-4-yl}-carbamic acid tert-butyl ester To a stirred solution of compound 13e (0.07 g, 0.291 mmol) and N-Boc piperidine (0.066 g, 0.345 mmol) in DMF (2 ml) was added tetramethyl guanidine (0.009 ml). The reaction was stirred at room temperature for 3 h. Upon completion, the DMF in the reaction mass was distilled out. The crude was diluted with 10% MeOH—CH$_2$Cl$_2$ and washed with water and concentrated under reduced pressure. The obtained crude was purified by preparative TLC to afford the required compound as an off-white solid (0.07 g).

(15b) 4-[2-(4-Amino-piperidin-1-yl)-ethyl]-6-methoxy-1-methyl-2-oxo-1,2-dihydro-quinoline-3-carbonitrile To a stirred solution of compound 15a (0.07 g) in CH$_2$Cl$_2$ was added a solution of 4M HCl in dioxane (2 ml) at 0° C. The reaction was stirred at room temperature for 4 h. The solvent in the reaction was distilled out to afford the required compound as an hydrochloric salt (0.04 g).

(15c) VT-03-00043

To a stirred solution of 15b (0.04 g, 0.11 mmol) and 2,3-Dihydro-benzo[1,4]dioxine-6-carbaldehyde (0.019 g, 0.11 mmol) in 1,2-DCE (2 ml) was added sodium triacetoxy borohydride (0.029 g, 0.141 mmol) and a catalytic amount of AcOH. The reaction was stirred at RT for 8 h. Upon completion, the solvent in the reaction was removed and the crude partitioned between water and 5% MeOH in CH$_2$Cl$_2$. The organic layers were dried over sodium sulfate and concentrated under reduced pressure to afford the product as an off white solid (0.005 g).

$^1$HNMR (400 MHz, DMSO-d6) δ 7.90 (d, 1H), 7.58 (d, 1H), 7.45 (dd, 1H), 6.92 (s, 1H), 6.81 (s, 2H), 4.23 (s, 4H), 3.82 (s, 6H), 3.65 (s, 2H), 3.22 (t, 4H), 2.99 (s, 1H), 2.72 (d, 1H), 2.66-2.68 (m, 2H), 2.12 (t, 2H), 1.82 (s, 2H), 1.28 (s, 2H). Mass spectra [M+H]+m/z 489.6

(16) Synthesis of VT-03-00045

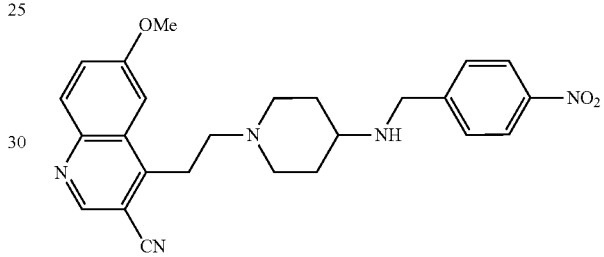

(16a) 4-(4-Nitro-benzylamino)-piperidine-1-carboxylic acid tert-butyl ester

To a stirred solution of 4-amino-piperidine-1-carboxylic acid tert-butyl ester (0.25 g, 1.25 mmol) and 4-nitrobenzaldehyde (0.211 g, 1.25 mmol) in ethanol (6 ml) was added titanium isopropoxide (0.25 ml) at 0° C. and stirred. The reaction was gradually brought to RT and stirred for 16 h. Then sodium borohydride (0.047 g, 1.25 mmol) was added followed by catalytic amount of Acetic acid and stirred for 3 h at ambient temperature. Upon completion, the solvents in the reaction were distilled out. The crude was diluted with 5% MeOH—CH$_2$Cl$_2$ solution and washed with water. The organic layer was then dried over Sodium sulfate and concentrated under reduced pressure. The obtained crude (0.35 g) was confirmed to be the product by Mass spectrometry and was taken forward to the next step.

(16b) (4-Nitro-benzyl)-piperidin-4-yl-amine

To a stirred solution of compound 16a (0.28 g) in CH$_2$Cl$_2$ (3 ml) was added a solution of 4M HCl in dioxan (3 ml) at 0° C. The reaction was stirred at RT for 4 h. The solvent in the reaction was distilled out to afford the required compound as an hydrochloric salt (0.21 g).

(16c) VT-03-00045

To a stirred solution of Compound 6-Methoxy-4-vinyl-quinoline-3-carbonitrile (0.1 g, 0.476 mmol) and Compound 16b (0.147 g, 0.571 mmol) in DMF (4 ml) was added tetramethyl guanidine (0.03 ml). The reaction was stirred at RT for 3 h. Upon completion, the DMF in the reaction mass was distilled out. The crude was diluted with 10% MeOH—CH$_2$Cl$_2$ and washed with water and concentrated under reduced pressure. The obtained crude was purified by preparative TLC to afford the required compound as a yellow solid (0.03 g)

$^1$HNMR (400 MHz, CDCl$_3$) δ 8.81 (s, 1H), 8.22 (d, 2H), 8.15 (d, 1H), 7.55-7.59 (m, 3H), 7.32 (s, 1H), 4.08 (d, 6H), 3.45 (d, 3H), 3.01 (m, 2H), 2.75 (t, 2H), 2.45-2.48 (m, 1H), 2.23 (t, 2H), 1.98 (d, 2H).

Mass spectra [M+H]+m/z 446.2

(17) Synthesis of VT-03-00046

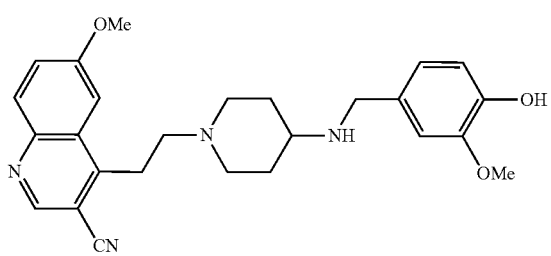 [SMILES: COc1ccc2ncc(C#N)c(CCN3CCC(NCc4ccc(O)c(OC)c4)CC3)c2c1]

(17a) 4-(4-Hydroxy-3-methoxy-benzylamino)-piperidine-1-carboxylic acid tert-butyl ester To a stirred solution of 4-amino-piperidine-1-carboxylic acid tert-butyl ester (0.2 g, 1.0 mmol) and 4-Hydroxy-3-methoxy-benzaldehyde (0.152 g, 1.0 mmol) in ethanol (4 ml) was added titanium isopropoxide (0.25 ml) at 0° C. and stirred. The reaction was gradually brought to RT and stirred for 16 h. Then sodiumborohydride (0.038 g, 1.20 mmol) was added followed by catalytic amount of acetic acid and stirred for 3 h at ambient temperature. Upon completion, the solvents in the reaction were distilled out. The crude was diluted with 5% MeOH—CH$_2$Cl$_2$ solution and washed with water. The organic layer was then dried over Sodium sulfate and concentrated under reduced pressure. The obtained crude was purified by 100-200 mesh-silicagel column chromatography, eluting the required compound with 5% MeOH—CH$_2$Cl$_2$. The obtained compound (0.1 g) was confirmed to be the product by Mass spectra.

(17b) 2-Methoxy-4-(piperidin-4-ylaminomethyl)-phenol

To a stirred solution of compound 17a (0.25 g) in CH$_2$Cl$_2$ (3 mL) was added a solution of 4M HCl in dioxan (2 ml) at 0° C. The reaction was stirred at RT for 4 h. The solvent in the reaction was distilled out to afford the required compound as an hydrochloric salt (0.23 g).

(17c) VT-03-00046

To a stirred solution of compound 6-methoxy-4-vinyl-quinoline-3-carbonitrile (0.07 g, 0.33 mmol) and compound 17b (0.093 g, 0.39 mmol) in DMF (4 mL) was added tetramethyl guanidine (0.1 mL). The reaction was stirred at RT for 3 h. Upon completion, the DMF in the reaction mass was distilled out. The crude was diluted with 10% MeOH—CH$_2$Cl$_2$ and washed with water and concentrated under reduced pressure. The obtained crude was purified by preparative TLC to afford the required compound as an off white solid (0.05 g).

$^1$HNMR (400 MHz, CDCl$_3$) δ 8.76 (s, 1H), 8.15 (d, 1H), 8.13 (d, 1H), 8.05 (d, 1H), 7.06 (d, 1H), 6.93 (s, 1H), 6.89 (d, 1H), 5.20 (s, 1H), 4.02 (s, 3H), 3.85 (s, 3H), 3.72 (s, 2H), 3.32 (t, 2H), 5.20 (s, 1H), 3.01 (d, 2H), 2.85 (t, 2H), 2.61-2.63 (m, 1H), 2.35 (t, 2H), 2.05 (d, 2H), 1.72 (d, 2H).

Mass spectra [M+H]+m/z 447.3

(18) Synthesis of VT-03-00048

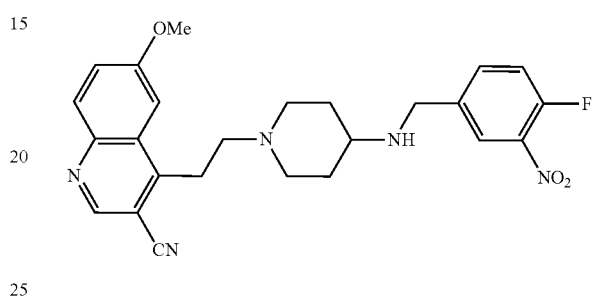

(18a) 4-(4-Fluoro-3-nitro-benzylamino)-piperidine-1-carboxylic acid tert-butyl ester To a stirred solution of 4-amino-piperidine-1-carboxylic acid tert-butyl ester (0.25 g, 1.25 mmol) and 4-fluoro-3-nitrobenzaldehyde (0.211 g, 1.25 mmol) in ethanol (4 ml) was added titanium isopropoxide (0.25 mL) at 0° C. and stirred. The reaction was gradually brought to RT and stirred for 16 h. Then sodiumborohydride (0.047 g, 1.25 mmol) was added followed by catalytic amount of acetic acid and stirred for 3 h at ambient temperature. Upon completion, the solvents in the reaction were distilled out. The crude was diluted with 5% MeOH—CH$_2$Cl$_2$ solution and washed with water. The organic layer was then dried over sodium sulfate and concentrated under reduced pressure. The obtained crude was purified by 100-200 mesh-silicagel column chromatography, eluting the required compound with 80% EtOAc-hexanes. The obtained compound (0.28 g) was confirmed to be the product by mass spectra.

(18b) (4-Fluoro-3-nitro-benzyl)-piperidin-4-yl-amine

To a stirred solution of compound 18a (0.28 g) in CH$_2$Cl$_2$ (3 ml) was added a solution of 4M HCl in dioxan (2 ml) at 0° C. The reaction was stirred at RT for 4 h. The solvent in the reaction was distilled out to afford the required compound as an hydrochloric salt (0.21 g).

(18c) VT-03-00048

To a stirred solution of Compound 6-methoxy-4-vinyl-quinoline-3-carbonitrile (0.1 g, 0.476 mmol) and Compound 18b (0.145 g, 0.571 mmol) in DMF (4 ml) was added tetramethyl guanidine (0.05 ml). The reaction was stirred at RT for 3 h. Upon completion, the DMF in the reaction mass was distilled out. The crude was diluted with 10% MeOH—CH$_2$Cl$_2$ and washed with water and concentrated under reduced pressure. The obtained crude was purified by preparative TLC to afford the required compound as an off-white solid (0.03 g).

¹HNMR (400 MHz, CDCl₃) δ 8.91 (s, 1H), 8.03 (d, 2H), 7.61 (q, 1H), 7.45 (d, 1H), 7.36 (s, 1H), 7.22 (d, 1H), 3.98 (s, 3H), 2.89 (s, 2H), 3.48 (t, 2H), 3.09 (d, 2H), 2.78 (t, 2H), 2.55-2.58 (m, 1H), 2.23 (t, 2H), 1.92 (d, 2H), 1.56 (d, 2H). Mass spectra [M+H]+m/z 464.7

(19) Synthesis of VT-03-00049

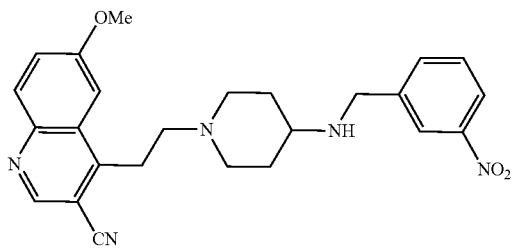 [SMILES: COc1ccc2ncc(C#N)c(CCN3CCC(NCc4cccc([N+](=O)[O-])c4)CC3)c2c1]

(19a) 4-(3-Nitro-benzylamino)-piperidine-1-carboxylic acid tert-butyl ester

To a stirred solution of 4-amino-piperidine-1-carboxylic acid tert-butyl ester (0.25 g, 1.25 mmol) and 3-nitro-benzaldehyde (0.211 g, 1.25 mmol) in ethanol (6 ml) was added titanium isopropoxide (0.25 ml) at 0° C. and stirred. The reaction was gradually brought to RT and stirred for 16 h. Then sodium borohydride (0.047 g, 1.25 mmol) was added followed by catalytic amount of acetic acid and stirred for 3 h at ambient temperature. Upon completion, the solvents in the reaction were distilled out. The crude was diluted with 5% MeOH—CH₂Cl₂ solution and washed with water. The organic layer was then dried over sodium sulfate and concentrated under reduced pressure. The obtained crude (0.35 g) was confirmed to be the product by mass spectrometry and was taken forward to the next step.

(19b) (3-Nitro-benzyl)-piperidin-4-yl-amine

To a stirred solution of compound 19a (0.28 g) in CH₂Cl₂ (3 ml) was added a solution of 4M HCl in dioxan (3 ml) at 0° C. The reaction was stirred at RT for 4 h. The solvent in the reaction was distilled out to afford the required compound as an hydrochloric salt (0.21 g).

(19c) VT-03-00049

To a stirred solution of compound 6-methoxy-4-vinyl-quinoline-3-carbonitrile (0.1 g, 0.476 mmol) and Compound 19b (0.147 g, 0.571 mmol) in DMF (4 ml) was added tetramethyl guanidine (0.03 ml). The reaction was stirred at RT for 3 h. Upon completion, the DMF in the reaction mass was distilled out. The crude was diluted with 10% MeOH—CH₂Cl₂ and washed with water and concentrated under reduced pressure. The obtained crude was purified by preparative TLC to afford the required compound as a yellow solid (0.03 g).

¹HNMR (400 MHz, CDCl₃) δ 8.78 (s, 1H), 8.18 (s, 1H), 8.03 (dd, 2H), 7.63 (d, 1H), 7.43 (d, 2H), 7.23 (s, 1H), 3.75 (s, 3H), 3.63 (s, 2H), 3.40-3.42 (m, 2H), 2.96-2.99 (m, 2H), 2.73-2.76 (m, 2H), 2.49-2.53 (m, 1H), 2.17-2.21 (m, 2H), 1.89 (d, 2H), 1.45 (d, 2H). Mass spectra [M+H]+m/z 446.5

(20) Synthesis of VT-03-00050

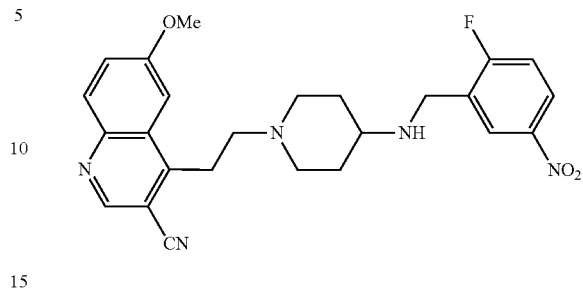

(20a) 4-(2-Fluoro-5-nitro-benzylamino)-piperidine-1-carboxylic acid tert-butyl ester To a stirred solution of 4-Amino-piperidine-1-carboxylic acid tert-butyl ester (0.25 g, 1.25 mmol) and 2-fluoro-5-nitrobenzaldehyde (0.211 g, 1.25 mmol) in ethanol (4 ml) was added titanium isopropoxide (0.25 ml) at 0° C. and stirred. The reaction was gradually brought to RT and stirred for 16 h. Then sodium borohydride (0.047 g, 1.25 mmol) was added followed by catalytic amount of acetic acid and stirred for 3 h at ambient temperature. Upon completion, the solvents in the reaction were distilled out. The crude was diluted with 5% MeOH—CH₂Cl₂ solution and washed with water. The organic layer was then dried over sodium sulfate and concentrated under reduced pressure. The obtained crude was purified by 100-200 mesh-silicagel column chromatography, eluting the required compound with 80% EtOAc-hexanes. The obtained compound (0.25 g) was confirmed to be the product by Mass spectra.

(20b) (2-Fluoro-5-nitro-benzyl)-piperidin-4-yl-amine

To a stirred solution of compound 20a (0.28 g) in CH₂Cl₂ (3 ml) was added a solution of 4M HCl in dioxan (2 ml) at 0° C. The reaction was stirred at RT for 4 h. The solvent in the reaction was distilled out to afford the required compound as an hydrochloric salt (0.22 g).

(20c) VT-03-00050

To a stirred solution of Compound 6-methoxy-4-vinyl-quinoline-3-carbonitrile (0.1 g, 0.476 mmol) and Compound 20b (0.145 g, 0.571 mmol) in DMF (4 ml) was added tetramethyl guanidine (0.05 ml). The reaction was stirred at RT for 3 h. Upon completion, the DMF in the reaction mass was distilled out. The crude was diluted with 10% MeOH—CH₂Cl₂ and washed with water and concentrated under reduced pressure. The obtained crude was purified by preparative TLC to afford the required compound as an off-white solid (0.02 g).

¹HNMR (400 MHz, CDCl₃) δ 8.87 (s, 1H), 8.40 (d, 1H), 8.15 (d, 1H), 8.05 (d, 1H), 7.50 (d, 1H), 7.35 (s, 1H), 7.20 (s, 1H), 3.98 (s, 3H), 3.86 (s, 2H), 3.49 (t, 2H), 3.01 (d, 2H), 2.75 (t, 2H), 2.54-2.56 (m, 1H), 2.25 (t, 2H), 1.96 (d, 2H), 1.56 (d, 2H). Mass spectra [M+H]+m/z 464.2

(20) Synthesis of VT-03-00051

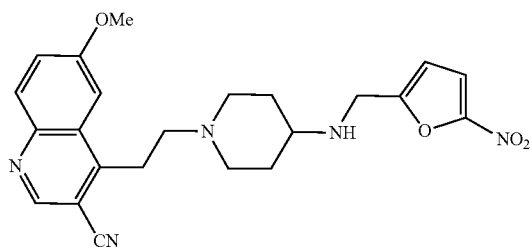 [SMILES: COc1ccc2ncc(C#N)c(CCN3CCC(NCc4ccc([N+](=O)[O-])o4)CC3)c2c1]

(21a) 4-[(5-Nitro-furan-2-ylmethyl)-amino]-piperidine-1-carboxylic acid tert-butyl ester To a stirred solution of 4-Amino-piperidine-1-carboxylic acid tert-butyl ester (0.25 g, 1.25 mmol) and 5-nitro-furan-2-carbaldehyde (0.176 g, 1.25 mmol) in ethanol (4 ml) was added titanium isopropoxide (0.25 ml) at 0° C. and stirred. The reaction was gradually brought to RT and stirred for 16 h. Then sodium borohydride (0.047 g, 1.25 mmol) was added followed by catalytic amount of acetic acid and stirred for 3 h at ambient temperature. Upon completion, the solvents in the reaction were distilled out. The crude was diluted with 5% MeOH—$CH_2Cl_2$ solution and washed with water. The organic layer was then dried over sodium sulfate and concentrated under reduced pressure. The obtained crude was purified by 100-200 mesh-silicagel Column chromatography, eluting the required compound with 75% EtOAc-hexanes. The obtained compound (0.35 g) was confirmed to be the product by Mass spectra.

(21b) (5-Nitro-furan-2-ylmethyl)-piperidin-4-yl-amine

To a stirred solution of compound 21a (0.28 g) in $CH_2Cl_2$ (3 ml) was added a solution of 4M HCl in dioxan (2 ml) at 0° C. The reaction was stirred at RT for 4 h. The solvent in the reaction was distilled out to afford the required compound as an hydrochloric salt (0.35 g).

(21c) VT-03-00051

To a stirred solution of Compound 6-methoxy-4-vinyl-quinoline-3-carbonitrile (0.07 g, 0.33 mmol) and Compound 21b (0.09 g, 0.33 mmol) in DMF (4 ml) was added tetramethyl guanidine (0.05 ml). The reaction was stirred at RT for 3 h. Upon completion, the DMF in the reaction mass was distilled out. The crude was diluted with 10% MeOH—$CH_2Cl_2$ and washed with water and concentrated under reduced pressure. The obtained crude was purified by preparative TLC to afford the required compound as an off-white solid (0.015 g).

$^1$HNMR (400 MHz, $CDCl_3$) δ 8.79 (s, 1H), 7.98 (d, 1H), 7.45 (d, 1H), 7.29 (s, 1H), 7.09 (dd, 1H), 6.39 (dd, 1H), 3.98 (s, 3H), 3.82 (s, 2H), 3.41 (t, 2H), 2.98 (t, 2H), 2.66-2.69 (m, 2H), 2.49-2.52 (m, 1H), 2.07-2.09 (m, 2H), 1.85-1.89 (m, 2H), 1.45-1.49 (m, 2H). Mass spectra [M+H]+m/z 436.2

(22) Synthesis of VT-03-00052

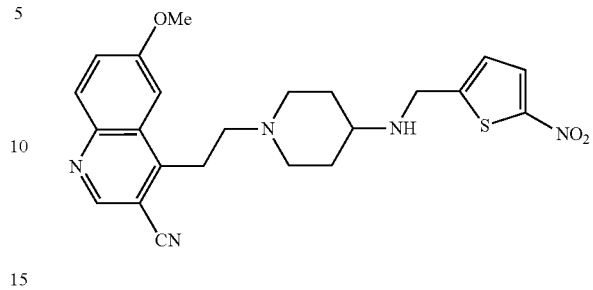

(22a) 4-[(5-Nitro-thiophen-2-ylmethyl)-amino]-piperidine-1-carboxylic acid tert-butyl ester To a stirred solution of 4-Amino-piperidine-1-carboxylic acid tert-butyl ester (0.25 g, 1.25 mmol) and 5-nitro-thiophene-2-carbaldehyde (0.196 g, 1.25 mmol) in ethanol (4 ml) was added titanium isopropoxide (0.25 ml) at 0° C. and stirred. The reaction was gradually brought to RT and stirred for 16 h. Then sodiumborohydride (0.047 g, 1.25 mmol) was added followed by catalytic amount of acetic acid and stirred for 3 h at ambient temperature. Upon completion, the solvents in the reaction were distilled out. The crude was diluted with 5% MeOH—$CH_2Cl_2$ solution and washed with water. The organic layer was then dried over sodium sulfate and concentrated under reduced pressure. The obtained crude was purified by 100-200 mesh-silicagel column chromatography, eluting the required compound with 75% EtOAc-Hexanes. The obtained compound (0.32 g) was confirmed to be the product by mass spectra.

(22b) (5-Nitro-thiophen-2-ylmethyl)-piperidin-4-yl-amine

To a stirred solution of compound 22a (0.25 g) in $CH_2Cl_2$ (3 ml) was added a solution of 4M HCl in dioxan (2.5 ml) at 0° C. The reaction was stirred at RT for 4 h. The solvent in the reaction was distilled out to afford the required compound as an hydrochloric salt (0.32 g).

(22c) VT-03-00052

To a stirred solution of Compound 6-Methoxy-4-vinyl-quinoline-3-carbonitrile (0.07 g, 0.33 mmol) and Compound 22b (0.081 g, 0.33 mmol) in DMF (4 ml) was added Tetramethyl Guanidine (0.05 ml). The reaction was stirred at RT for 3 h. Upon completion, the DMF in the reaction mass was distilled out. The crude was diluted with 10% MeOH—$CH_2Cl_2$ and washed with water and concentrated under reduced pressure. The obtained crude was purified by preparative TLC to afford the required compound as an off-white solid (0.013 g).

$^1$HNMR (400 MHz, $CDCl_3$) δ 9.32 (s, 1H), 8.61 (d, 1H), 8.32 (s, 1H), 8.01 (d, 1H), 7.82 (s, 1H), 7.36 (s, 1H), 4.36 (s, 2H), 4.25 (s, 3H), 3.72 (t, 2H), 3.25 (d, 2H), 2.91 (t, 2H), 2.75-2.77 (m, 1H), 2.40 (t, 2H), 2.19-2.23 (m, 1H), 2.18 (d, 2H), 1.53-1.57 (m, 3H). Mass spectra [M+H]+m/z 452.3

(23) Synthesis of VT-03-00053

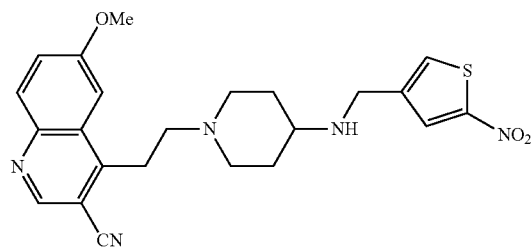 [SMILES: COc1ccc2ncc(C#N)c(CCN3CCC(NCc4csc([N+](=O)[O-])c4)CC3)c2c1]

(23a) 4-[(5-Nitro-thiophen-3-ylmethyl)-amino]-piperidine-1-carboxylic acid tert-butyl ester To a stirred solution of 4-Amino-piperidine-1-carboxylic acid tert-butyl ester (0.15 g, 0.75 mmol) and 5-nitro-thiophene-3-carbaldehyde (0.12 g, 0.75 mmol) in ethanol (4 ml) was added titanium isopropoxide (0.15 ml) at 0° C. and stirred. The reaction was gradually brought to RT and stirred for 16 h. Then sodium boro hydride (0.028 g, 0.75 mmol) was added followed by catalytic amount of acetic acid and stirred for 3 h at ambient temperature. Upon completion, the solvents in the reaction were distilled out. The crude was diluted with 5% MeOH—$CH_2Cl_2$ solution and washed with water. The organic layer was then dried over sodium sulfate and concentrated under reduced pressure. The obtained crude was purified by 100-200 mesh-silicagel column chromatography, eluting the required compound with 85% EtOAc-hexanes. The obtained compound (0.25 g) was confirmed to be the product by mass spectra.

(22b) (5-Nitro-thiophen-3-ylmethyl)-piperidin-4-yl-amine

To a stirred solution of compound 23a (0.25 g) in $CH_2Cl_2$ (3 ml) was added a solution of 4M HCl in dioxan (2.5 ml) at 0° C. The reaction was stirred at RT for 4 h. The solvent in the reaction was distilled out to afford the required compound as an hydrochloric salt (0.31 g).

(23c) VT-03-00053

To a stirred solution of Compound 6-methoxy-4-vinyl-quinoline-3-carbonitrile (0.07 g, 0.33 mmol) and Compound 23b (0.081 g, 0.33 mmol) in DMF (4 ml) was added tetramethyl guanidine (0.05 ml). The reaction was stirred at RT for 3 h. Upon completion, the DMF in the reaction mass was distilled out. The crude was diluted with 10% MeOH—$CH_2Cl_2$ and washed with water and concentrated under reduced pressure. The obtained crude was purified by preparative TLC to afford the required compound as an off-white solid (0.02 g).

$^1$HNMR (400 MHz, $CDCl_3$) δ 8.85 (s, 1H), 8.19 (d, 1H), 7.92 (s, 1H), 7.57 (d, 1H), 7.02 (s, 1H), 7.38 (s, 1H), 3.98 (s, 3H), 3.81 (s, 2H), 3.46 (t, 2H), 3.08 (d, 2H), 2.78 (t, 2H), 2.56-2.59 (m, 1H), 2.28 (t, 2H), 2.09 (s, 5H), 1.98 (d, 2H). Mass spectra [M+H]+m/z 452.8

(24) Synthesis of VT-03-00054

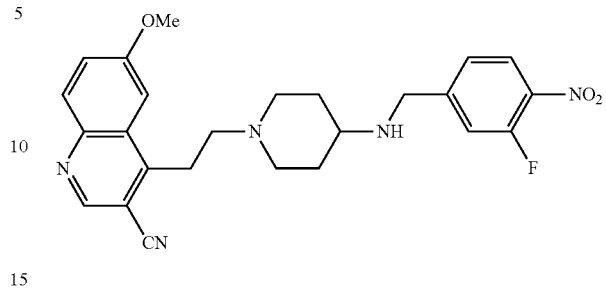

(24a) 4-(3-Fluoro-4-nitro-benzylamino)-piperidine-1-carboxylic acid tert-butyl ester To a stirred solution of 4-Amino-piperidine-1-carboxylic acid tert-butyl ester (0.2 g, 1.0 mmol) and 3-fluoro-4-nitrobenzaldehyde (1.0 mmol) in ethanol (4 ml) was added titanium isopropoxide (0.15 ml) at 0° C. and stirred. The reaction was gradually brought to RT and stirred for 16 h. Then sodium borohydride (0.038 g, 1.0 mmol) was added followed by catalytic amount of acetic acid and stirred for 3 h at ambient temperature. Upon completion, the solvents in the reaction were distilled out. The crude was diluted with 5% MeOH—$CH_2Cl_2$ solution and washed with water. The organic layer was then dried over sodium sulfate and concentrated under reduced pressure. The obtained crude was purified by 100-200 mesh-silicagel column chromatography, eluting the required compound with 10% MeOH—$CH_2Cl_2$. The obtained compound (0.18 g) was confirmed to be the product by mass spectra.

(24b) (3-Fluoro-4-nitro-benzyl)-piperidin-4-yl-amine

To a stirred solution of compound 24a (0.18 g) in $CH_2Cl_2$ (3 ml) was added a solution of 4M HCl in dioxan (3 ml) at 0° C. The reaction was stirred at RT for 4 h. The solvent in the reaction was distilled out to afford the required compound as an hydrochloric salt (0.2 g).

(24c) VT-03-00054

To a stirred solution of Compound 6-methoxy-4-vinyl-quinoline-3-carbonitrile (0.08 g, 0.38 mmol) and Compound 24b (0.1 g, 0.42 mmol) in DMF (4 ml) was added tetramethyl guanidine (0.05 ml). The reaction was stirred at RT for 3 h. Upon completion, the DMF in the reaction mass was distilled out. The crude was diluted with 5% MeOH—$CH_2Cl_2$ and washed with water and concentrated under reduced pressure. The obtained crude was purified by preparative TLC to afford the required compound as an off-white solid (0.02 g).

$^1$HNMR (400 MHz, $CDCl_3$) δ 8.81 (s, 1H), 8.09 (t, 2H), 7.59 (d, 1H), 7.38 (d, 2H), 7.25 (s, 1H), 3.98 (s, 3H), 3.91 (s, 2H), 3.41-3.45 (m, 2H), 3.06-3.09 (m, 2H), 2.77-3.01 (m, 2H), 2.91-2.93 (m, 1H), 2.20-2.23 (m, 2H), 1.96-1.99 (m, 2H), 1.44-1.47 (m, 2H). Mass spectra [M+H]+m/z 464.1

(25) Synthesis of VT-03-00055

(26) Synthesis of VT-03-00056

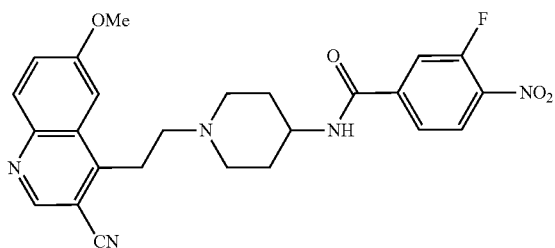 [SMILES: COc1ccc2ncc(C#N)c(CCN3CCC(NC(=O)c4ccc([N+](=O)[O-])c(F)c4)CC3)c2c1]

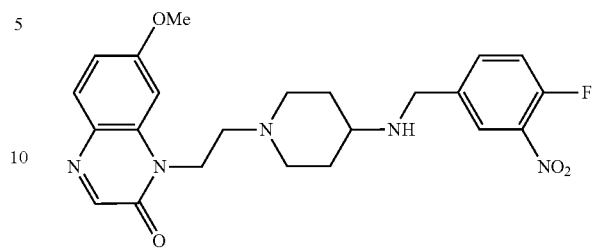

(25a) 4-(3-Fluoro-4-nitro-benzoylamino)-piperidine-1-carboxylic acid tert-butyl ester To a stirred solution of 4-Amino-piperidine-1-carboxylic acid tert-butyl ester (0.2 g, 1.0 mmol) in $CH_2Cl_2$ (5 ml) was added $Et_3N$ (0.15 ml, 2.0 mmol) at 0° C. To it was added 3-fluoro-4-nitro-benzoyl chloride (1.0 mmol) dropwise and stirred. The reaction was gradually brought to RT and stirred for 4 h. Upon completion, the solvents in the reaction were distilled out. The crude was diluted with 5% MeOH—$CH_2Cl_2$ solution and washed with water. The organic layer was then dried over sodium sulfate and concentrated under reduced pressure. The obtained crude was purified by 100-200 mesh-silicagel column chromatography, eluting the required compound with 5% MeOH—$CH_2Cl_2$. The obtained compound (0.19 g) was confirmed to be the product by mass spectra.

(25b) 3-Fluoro-4-nitro-N-piperidin-4-yl-benzamide

To a stirred solution of compound 25a (0.18 g) in $CH_2Cl_2$ (3 ml) was added a solution of 4M HCl in dioxan (3 ml) at 0° C. The reaction was stirred at RT for 4 h. The solvent in the reaction was distilled out to afford the required compound as an hydrochloric salt (0.2 g).

(25c) VT-03-00055

To a stirred solution of Compound 6-methoxy-4-vinyl-quinoline-3-carbonitrile (0.07 g, 0.38 mmol) and Compound 25b (0.1 g, 0.42 mmol) in DMF (4 ml) was added tetramethyl guanidine (0.05 ml). The reaction was stirred at RT for 3 h. Upon completion, the DMF in the reaction mass was distilled out. The crude was diluted with 5% MeOH—$CH_2Cl_2$ and washed with water and concentrated under reduced pressure. The obtained crude was purified by preparative TLC to afford the required compound as an off-white solid (0.02 g).

$^1$HNMR (400 MHz, $CDCl_3$) δ 8.89 (s, 1H), 8.02-8.09 (m, 2H), 7.72 (d, 1H), 7.65 (d, 1H), 7.56 (d, 1H), 7.32 (s, 1H), 6.01-6.03 (m, 1H), 4.08 (m, 1H), 3.98 (s, 3H), 3.42 (t, 2H), 3.02 (d, 2H), 2.80 (t, 2H), 2.39 (t, 2H), 2.12 (d, 2H), 1.75 (d, 2H). Mass spectra [M+H]+m/z 478.5

(26a) (4-Methoxy-2-nitro-phenylamino)-acetic acid ethyl ester

To a stirred solution of 4-methoxy-3-nitroaniline (10 g, 59.6 mmol) in ethylbromoacetate (11.85 g, 71.42 mmol) was added potassium carbonate (16.42 g, 119.04 mmol) and heated at 150° C. for 4 h. Upon completion, the reaction was diluted with $CH_2Cl_2$, basified with saturated $NaHCO_3$ solution and extracted with $CH_2Cl_2$. The combined organic layers were dried over $Na_2SO_4$ and concentrated under reduced pressure. The obtained crude was purified using 100-200 mesh column chromatography, eluting the required compound (5 g) as a red color solid.

(26b) 7-Methoxy-3,4-dihydro-1H-quinoxalin-2-one

To a stirred solution of Compound 26a (2.4 g, 9.44 mmol) in AcOH (25 ml) was added Iron powder (5 g, 94.4 mmol) ar RT and heated at 90° C. for 4 h. Upon completion, the solvent was evaporated and the obtained crude was basified with saturated NaHCO3 solution, extracted with EtOAc. The organic layers were dried over Sodium sulphate and concentrated under reduced pressure. The obtained crude was washed with diethyl ether and dried to afford the required compound (0.8 g) as an off-white solid.

(26c) 7-Methoxy-1H-quinoxalin-2-one

To a stirred solution of Compound 26b (3 g, 16.85 mmol) in 8% NaOH solution (39.6 ml) was added 30% $H_2O_2$ solution (35.1 ml) at RT. The reaction was heated at 80° C. for 4 h after which was added AcOH (4.5 ml) dropwise at RT. Upon completion, the filtered solids were given water and diethyl ether washings to afford the required compound (2 g) as an off-white solid.

(26d) [1-(2-Hydroxy-ethyl)-piperidin-4-yl]-carbamic acid tert-butyl ester

To a stirred solution of piperidin-4-yl-carbamic acid tert-butyl ester (4.0 g, 20.10 mmol) in acetonitrile (20 ml) was added triethylamine (4.34 g, 40.2 mmol) and bromoethanol (2.76 g, 22.11 mmol) at RT and heated at 80° C. for 18 h in a sealed tube. Upon completion, the ethanol in the reaction was distilled out and redissolved in ethyl acetate. This solution was washed with water and brine and then dried over $Na_2SO_4$ and concentrated under reduced pressure. The obtained crude was purified by (100-200) mesh silicagel column chromatography eluting the required compound with 10% MeOH—$CH_2Cl_2$ as an off-white solid (1.7 g).

(26e) Methanesulfonic acid 2-(4-tert-butoxycarbo-nylamino-piperidin-1-yl)-ethyl ester To a stirred solution of compound 26d (1.1 g, 9.05 mmol) in CH$_2$Cl$_2$ (12 ml) was added triethylamine (1.95 g, 18.106 mmol) followed by dropwise addition of mesylchloride (1.145 g, 9,958 mmol) at 0° C. The reaction was gradually brought to RT and stirred for 1 h. Upon completion, the reaction was diluted with CH$_2$Cl$_2$, basified with potassium phosphate buffer (pH=7) and extracted. The organic layer was washed with water, then with brine solution, dried over sodium sulphate and concentrated under reduced pressure. The obtained crude material (1.7 g) was taken to the next step without any further purification.

(26f) {1-[2-(7-Methoxy-2-oxo-2H-quinoxalin-1-yl)-ethyl]-piperidin-4-yl}-carbamic acid tert-butyl ester To a stirred solution of Compound 26c (0.2 g, 1.13 mmol) in DMF (2 ml) at 0° C. was added NaH (0.054 g, 2.3 mmol). The reaction was slowly brought to ambient temperature and stirred for 1 h. Then Compound 26e (0.5 g, 1.36 mmol) in DMF (2 ml) was added at RT and stirred for 16 h. Upon completion, the reaction was quenched with chilled water and extracted into ethylacetate. The combined layers were dried over Na$_2$SO$_4$ and concentrated under reduced pressure. The obtained crude was purified by (100-200 mesh) silicagel column chromatography eluting the required compound with 5% MeOH—CH$_2$Cl$_2$ as red colored viscous material (0.05 g).

(26 g) 1-[2-(4-Amino-piperidin-1-yl)-ethyl]-7-methoxy-1H-quinoxalin-2-one

To a stirred solution of compound 26f (0.3 g) in CH$_2$Cl$_2$ (3 ml) was added a solution of 4M HCl in dioxan (3 ml) at 0° C. The reaction was stirred at RT for 4 h. The solvent in the reaction was distilled out to afford the required compound as an hydrochloric salt (0.2 g).

(26 h) VT-03-00056

To a stirred solution of Compound 26 g (0.1 g, 0.33 mmol) and 4-fluoro-3-nitro-benzaldehyde (0.067 g, 0.39 mmol) in ethanol (3 ml) was added titanium isopropoxide (0.1 ml) at 0° C. and stirred. The reaction was gradually brought to RT and stirred for 16 h. Then sodium borohydride (0.024 g, 0.66 mmol) was added followed by catalytic amount of acetic acid and stirred for 3 h at ambient temperature. Upon completion, the solvents in the reaction were distilled out. The crude was diluted with 5% MeOH—CH$_2$Cl$_2$ solution and washed with water. The organic layer was then dried over sodium sulfate and concentrated under reduced pressure. The obtained crude was purified by 100-200 mesh-silicagel column chromatography, eluting the required compound with 10% MeOH—CH$_2$Cl$_2$. The obtained compound (0.01 g) was confirmed to be the product by mass spectra and 1H-NMR.

$^1$HNMR (400 MHz, CDCl$_3$) δ 8.16 (s, 1H), 8.05 (d, 1H), 7.77 (d, 1H), 7.61 (d, 1H), 7.26 (s, 1H), 7.23 (d, 1H), 6.93 (d, 1H), 6.91 (d, 1H), 4.36 (t, 3H), 3.91 (s, 3H), 3.82 (s, 2H), 3.01 (d, 2H), 2.74 (t, 2H), 2.51 (s, 1H), 2.20 (t, 2H), 1.98 (d, 2H), 1.43-1.46 (m, 2H). Mass spectra [M+H]+m/z 456.3

(27) Synthesis of VT-03-00057

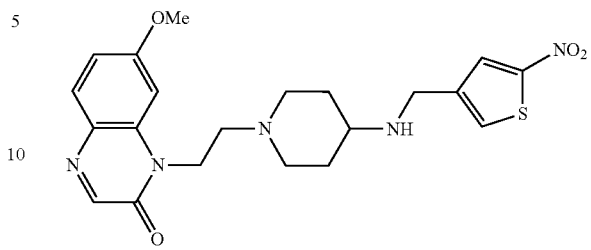

To a stirred solution of Compound 26 g (0.9 g, 0.29 mmol) and 5-nitro-thiophene-3-carbaldehyde (0.046 g, 0.3 mmol) in ethanol (4 ml) was added titanium isopropoxide (0.1 ml) at 0° C. and stirred. The reaction was gradually brought to RT and stirred for 16 h. Then sodium borohydride (0.011 g, 0.66 mmol) was added followed by catalytic amount of acetic acid and stirred for 3 h at ambient temperature. Upon completion, the solvents in the reaction were distilled out. The crude was diluted with 5% MeOH—CH$_2$Cl$_2$ solution and washed with water. The organic layer was then dried over sodium sulfate and concentrated under reduced pressure. The obtained crude was purified by 100-200 mesh-silicagel column chromatography, eluting the required compound with 10% MeOH—CH$_2$Cl$_2$. The obtained compound (0.016 g) was confirmed to be the product by mass spectra and 1H-NMR.

$^1$HNMR (400 MHz, CDCl$_3$) δ 8.19 (s, 1H), 7.92 (s, 1H), 7.80 (d, 1H), 7.41 (s, 1H), 6.92 (d, 1H), 6.85 (s, 1H), 4.38 (t, 2H), 3.98 (s, 3H), 3.81 (s, 2H), 3.09 (d, 2H), 2.72 (t, 2H), 2.56-2.58 (m, 1H), 2.21-2.24 (m, 2H), 1.92 (d, 2H), 1.49 (d, 2H). Mass spectra [M+H]+m/z 443.3

(28) Synthesis of VT-03-00058

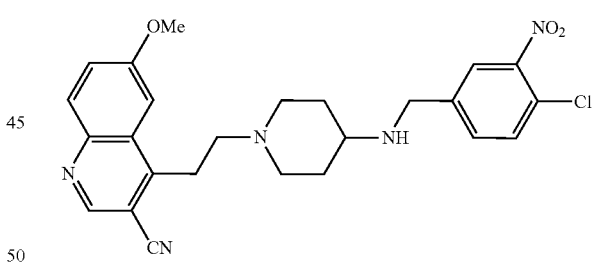

(28a) 4-(4-Chloro-3-nitro-benzylamino)-piperidine-1-carboxylic acid tert-butyl ester To a stirred solution of 4-amino-piperidine-1-carboxylic acid tert-butyl ester (0.2 g, 1.0 mmol) and 4-chloro-3-nitro-benzaldehyde (0.186 g, 1.0 mmol) in ethanol (4 ml) was added titanium isopropoxide (0.2 ml) at 0° C. and stirred. The reaction was gradually brought to RT and stirred for 16 h. Then sodium borohydride (0.038 g, 1.0 mmol) was added followed by catalytic amount of acetic acid and stirred for 3 h at ambient temperature. Upon completion, the solvents in the reaction were distilled out. The crude was diluted with 5% MeOH—CH$_2$Cl$_2$ solution and washed with water. The organic layer was then dried over sodium sulfate and concentrated under reduced pressure. The obtained crude was purified by 100-200 mesh-silicagel column chromatography, eluting the required compound with 70% EtOAc-Hexanes. The obtained compound (0.24 g) was confirmed to be the product by mass spectra.

(28b) (4-Chloro-3-nitro-benzyl)-piperidin-4-yl-amine

To a stirred solution of compound 28a (0.24 g) in $CH_2Cl_2$ (3 ml) was added a solution of 4M HCl in dioxan (3 ml) at 0° C. The reaction was stirred at RT for 4 h. The solvent in the reaction was distilled out to afford the required compound as an hydrochloric salt (0.28 g).

(28c) VT-03-00058

To a stirred solution of Compound 6-methoxy-4-vinyl-quinoline-3-carbonitrile (0.1 g, 0.47 mmol) and Compound 28b (0.153 g, 0.57 mmol) in DMF (4 ml) was added tetramethyl guanidine (0.05 ml). The reaction was stirred at RT for 3 h. Upon completion, the DMF in the reaction mass was distilled out. The crude was diluted with 5% MeOH—$CH_2Cl_2$ and washed with water and concentrated under reduced pressure. The obtained crude was purified by preparative TLC to afford the required compound as a pale yellow solid (0.015 g).
$^1$HNMR (400 MHz, $CDCl_3$) δ 8.82 (s, 1H), 8.15 (dd, 1H), 7.9 (d, 1H), 7.52-7.55 (m, 3H), 7.37 (s, 1H), 3.98 (s, 3H), 3.89 (s, 2H), 3.45 (t, 2H), 3.02 (d, 2H), 2.73 (t, 2H), 2.50-2.52 (m, 1H), 2.24 (t, 2H), 1.95 (d, 2H), 1.49 (q, 2H). Mass spectra [M+H]+m/z 480.6

(29) Synthesis of VT-03-00059

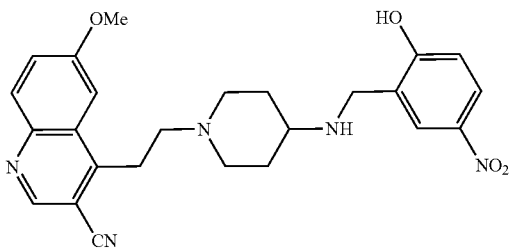 [SMILES: COc1ccc2ncc(C#N)c(CCN3CCC(NCc4cc([N+](=O)[O-])ccc4O)CC3)c2c1]

(29a) 4-(2-Hydroxy-5-nitro-benzylamino)-piperidine-1-carboxylic acid tert-butyl ester To a stirred solution of 4-amino-piperidine-1-carboxylic acid tert-butyl ester (0.2 g, 1.0 mmol) and 2-hydroxy-5-nitro-benzaldehyde (0.186 g, 1.0 mmol) in ethanol (4 ml) was added titanium isopropoxide (0.2 ml) at 0° C. and stirred. The reaction was gradually brought to RT and stirred for 16 h. Then sodium borohydride (0.038 g, 1.0 mmol) was added followed by catalytic amount of acetic acid and stirred for 3 h at ambient temperature. Upon completion, the solvents in the reaction were distilled out. The crude was diluted with 5% MeOH—$CH_2Cl_2$ solution and washed with water. The organic layer was then dried over sodium sulfate and concentrated under reduced pressure. The obtained crude was purified by 100-200 mesh-silicagel column chromatography, eluting the required compound with 3% MeOH—$CH_2Cl_2$. The obtained compound (0.25 g) was confirmed to be the product by mass spectra.

(29b) 4-Nitro-2-(piperidin-4-ylaminomethyl)-phenol

To a stirred solution of compound 29a (0.25 g) in $CH_2Cl_2$ (3 ml) was added a solution of 4M HCl in dioxan (3 ml) at 0° C. The reaction was stirred at RT for 4 h. The solvent in the reaction was distilled out to afford the required compound as an hydrochloric salt (0.29 g).

(29c) VT-03-00059

To a stirred solution of Compound 6-methoxy-4-vinyl-quinoline-3-carbonitrile (0.1 g, 0.47 mmol) and Compound 29b (0.17 g, 0.57 mmol) in DMF (4 ml) was added tetramethyl guanidine (0.05 ml). The reaction was stirred at RT for 3 h. Upon completion, the DMF in the reaction mass was distilled out. The crude was diluted with 5% MeOH—$CH_2Cl_2$ and washed with water and concentrated under reduced pressure. The obtained crude was purified by preparative TLC to afford the required compound as an pale brown solid (0.015 g).
$^1$HNMR (400 MHz, $CDCl_3$) δ 8.81 (s, 1H), 8.01-8.05 (m, 2H), 7.91 (d, 1H), 7.51-7.54 (m, 1H), 7.26 (d, 1H), 6.83 (d, 1H), 4.13 (s, 2H), 3.96 (s, 3H), 3.41-3.44 (m, 2H), 3.02 (d, 2H), 2.74-2.77 (m, 2H), 2.51-2.54 (m, 2H), 2.20-2.25 (m, 2H), 2.01-2.04 (m, 2H), 1.44-1.46 (m, 2H). Mass spectra [M+H]+m/z 462.3

(30) Synthesis of VT-03-00060

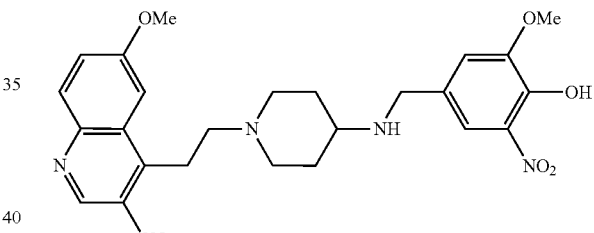

(30a) 4-(4-Hydroxy-3-methoxy-5-nitro-benzylamino)-piperidine-1-carboxylic acid tert-butyl ester To a stirred solution of 4-amino-piperidine-1-carboxylic acid tert-butyl ester (0.15 g, 0.75 mmol) and 4-hydroxy-3-methoxy-5-nitro-benzaldehyde (0.14 g, 0.75 mmol) in ethanol (4 ml) was added titanium isopropoxide (0.15 ml) at 0° C. and stirred. The reaction was gradually brought to RT and stirred for 16 h. Then sodiumborohydride (0.028 g, 0.75 mmol) was added followed by catalytic amount of acetic acid and stirred for 3 h at ambient temperature. Upon completion, the solvents in the reaction were distilled out. The crude was diluted with 5% MeOH—$CH_2Cl_2$ solution and washed with water. The organic layer was then dried over Sodium sulfate and concentrated under reduced pressure. The obtained crude was taken to the next step without further purification. The obtained crude (0.14 g) was confirmed to contain the product by Mass spectra.

(30b) 2-Methoxy-6-nitro-4-(piperidin-4-ylaminomethyl)-phenol

To a stirred solution of compound 30a (0.14 g) in $CH_2Cl_2$ (3 ml) was added a solution of 4M HCl in dioxan (2 ml) at 0° C. The reaction was stirred at RT for 4 h. The solvent in the reaction was distilled out to afford the required compound as an hydrochloric salt (0.15 g).

(30c) VT-03-00060

To a stirred solution of Compound 6-methoxy-4-vinyl-quinoline-3-carbonitrile (0.07 g, 0.33 mmol) and Compound 30b (0.112 g, 0.39 mmol) in DMF (4 ml) was added tetramethyl guanidine (0.05 ml). The reaction was stirred at RT for 3 h. Upon completion, the DMF in the reaction mass was distilled out. The crude was diluted with 5% MeOH—CH$_2$Cl$_2$ and washed with water and concentrated under reduced pressure. The obtained crude was purified by preparative TLC to afford the required compound as a pale brown solid (0.006 g). The compound was confirmed by mass spectra in the negative mode. Mass spectra [M−H]+ at m/z 490.4

(31) Synthesis of VT-03-00061

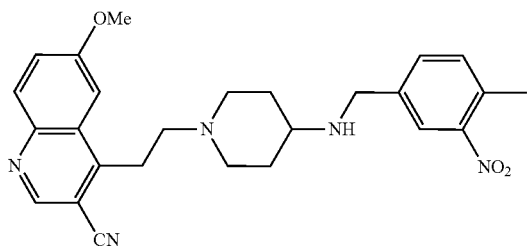 [SMILES: COc1ccc2ncc(C#N)c(CCN3CCC(NCc4ccc(C)c([N+](=O)[O-])c4)CC3)c2c1]

(31a) 4-(4-Methyl-3-nitro-benzylamino)-piperidine-1-carboxylic acid tert-butyl ester To a stirred solution of 4-amino-piperidine-1-carboxylic acid tert-butyl ester (0.3 g, 1.8 mmol) and 4-methyl-3-nitro-benzaldehyde (0.363 g, 1.8 mmol) in ethanol (6 ml) was added titanium isopropoxide (0.3 ml) at 0° C. and stirred. The reaction was gradually brought to RT and stirred for 16 h. Then sodium borohydride (0.068 g, 1.8 mmol) was added followed by catalytic amount of acetic acid and stirred for 3 h at ambient temperature. Upon completion, the solvents in the reaction were distilled out. The crude was diluted with 10% MeOH—CH$_2$Cl$_2$ solution and washed with water. The organic layer was then dried over sodium sulfate and concentrated under reduced pressure. The obtained crude was taken was purified by (100-200 mesh) silicagel column chromatography eluting the required compound with 80% EtOAc-Petether as a off-white solid (0.370 g).

(31b) (4-Methyl-3-nitro-benzyl)-piperidin-4-yl-amine

To a stirred solution of compound 31a (0.37 g) in CH$_2$Cl$_2$ (2 ml) was added a solution of 4M HCl in dioxan (1.5 ml) at 0° C. The reaction was stirred at RT for 4 h. The solvent in the reaction was distilled out to afford the required compound as an hydrochloric salt (0.4 g).

(31c) VT-03-00061

To a stirred solution of Compound 6-methoxy-4-vinyl-quinoline-3-carbonitrile (0.3 g, 1.42 mmol) and Compound 31b (0.48 g, 1.71 mmol) in DMF (5 ml) was added tetramethyl guanidine (0.05 ml). The reaction was stirred at RT for 3 h. Upon completion, the DMF in the reaction mass was distilled out. The crude was diluted with 5% MeOH—CH$_2$Cl$_2$ and washed with water and concentrated under reduced pressure. The obtained crude was purified by preparative TLC to afford the required compound as an off-white solid (0.056 g).

$^1$HNMR (400 MHz, CDCl$_3$) δ 8.81 (s, 1H), 8.08 (d, 1H), 7.96 (s, 1H), 7.45 (t, 2H), 7.31 (d, 2H), 4.01 (s, 3H), 3.92 (s, 2H), 3.51 (s, 2H), 3.02 (d, 2H), 2.78 (t, 2H), 2.60 (s, 3H), 2.52-2.56 (m, 1H), 2.25 (t, 2H), 1.95 (d, 2H), 1.54 (d, 2H). Mass spectra [M+H]+m/z 460.3

(32) Synthesis of VT-03-00062

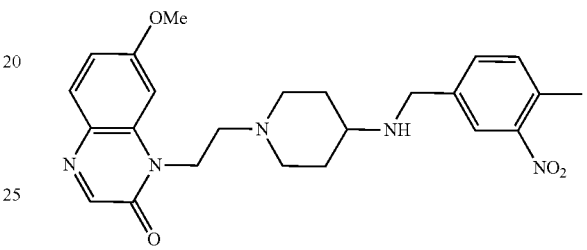

To a stirred solution of compound 26 g (0.2 g, 0.66 mmol) and 4-methyl-3-nitro-benzaldehyde (0.131 g, 0.794 mmol) in ethanol (4 ml) was added titanium isopropoxide (0.2 ml) at 0° C. and stirred. The reaction was gradually brought to RT and stirred for 16 h. Then sodiumborohydride (0.049 g, 1.34 mmol) was added followed by catalytic amount of acetic acid and stirred for 3 h at ambient temperature. Upon completion, the solvents in the reaction were distilled out. The crude was diluted with 5% MeOH—CH$_2$Cl$_2$ solution and washed with water. The organic layer was then dried over sodium sulfate and concentrated under reduced pressure. The obtained crude was purified by 100-200 mesh-silicagel column chromatography, eluting the required compound with 10% MeOH—CH$_2$Cl$_2$. The obtained compound (0.01 g) was confirmed to be the product by mass spectra and 1H-NMR.

$^1$HNMR (400 MHz, CDCl$_3$) δ 8.25 (s, 1H), 7.91 (s, 1H), 7.81 (d, 11H), 7.50 (d, 1H), 7.29 (d, 1H), 6.93 (d, 2 h), 4.36-4.39 (m, 3H), 4.18 (d, 2H), 3.97 (s, 3H), 3.85 (s, 2H), 3.74-3.77 (m, 3H), 3.01-3.04 (m, 2H), 2.73-2.78 (m, 2H), 2.60 (s, 3H), 2.30-2.35 (m, 3H), 1.85-1.89 (m, 3H). Mass spectra [M+H]+m/z 452.3

(33) Synthesis of VT-03-00062A

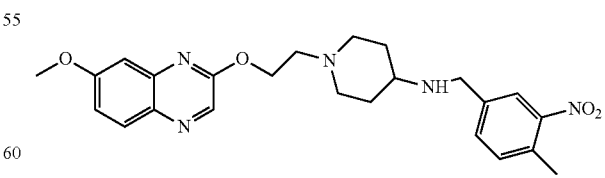

To a stirred solution of compound 26 g (0.2 g, 0.66 mmol) and 4-methyl-3-nitro-benzaldehyde (0.131 g, 0.794 mmol) in ethanol (4 ml) was added titanium isopropoxide (0.2 ml) at 0° C. and stirred. The reaction was gradually brought to RT and stirred for 16 h. Then sodiumborohydride (0.049 g, 1.34 mmol) was added followed by catalytic amount of acetic acid and stirred for 3 h at ambient temperature. Upon completion, the solvents in the reaction were distilled out. The crude was diluted with 5% MeOH—CH₂Cl₂ solution and washed with water. The organic layer was then dried over sodium sulfate and concentrated under reduced pressure. The obtained crude was purified by 100-200 mesh-silicagel column chromatography, eluting the required compound with 10% MeOH—CH₂Cl₂. The obtained compound (0.006 g) was confirmed to be the product by mass spectra and 1H-NMR.

¹HNMR (400 MHz, CDCl₃) δ 8.32 (s, 1H), 7.9 (s, 1H), 7.86 (d, 1H), 7.47 (d, 1H), 7.26-7.29 (m, 1H), 7.14-7.19 (m, 2H), 4.6 (t, 2H), 3.9 (s, 3H), 3.8 (s, 2H), 3.0 (d, 2H), 2.8 (s, 2H), 2.57 (s, 3H), 2.50-2.51 (m, 1H), 2.1 (s, 3H), 1.8-1.9 (m, 2H), 1.4-1.45 (m, 2H). Mass spectra [M+H]+m/z 452.3

(34) Synthesis of VT-03-00063

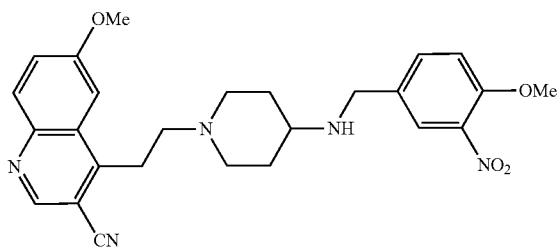 [SMILES: COc1ccc2ncc(C#N)c(CCN3CCC(NCc4ccc(OC)c([N+](=O)[O-])c4)CC3)c2c1]

(34a) 4-(4-Methoxy-3-nitro-benzylamino)-piperidine-1-carboxylic acid tert-butyl ester To a stirred solution of 4-amino-piperidine-1-carboxylic acid tert-butyl ester (0.3 g, 1.5 mmol) and 4-methoxy-3-nitro-benzaldehyde (0.27 g, 1.5 mmol) in ethanol (6 ml) was added titanium isopropoxide (0.3 ml) at 0° C. and stirred. The reaction was gradually brought to RT and stirred for 16 h. Then sodiumborohydride (0.057 g, 1.5 mmol) was added followed by catalytic amount of acetic acid and stirred for 3 h at ambient temperature. Upon completion, the solvents in the reaction were distilled out. The crude was diluted with 10% MeOH—CH₂Cl₂ solution and washed with water. The organic layer was then dried over sodium sulfate and concentrated under reduced pressure. The obtained crude was taken was purified by (100-200 mesh) silicagel column chromatography eluting the required compound with 70% EtOAc-petether as an yellow solid (0.43 g).

(34b) (4-Methoxy-3-nitro-benzyl)-piperidin-4-yl-amine

To a stirred solution of compound 34a (0.43 g) in CH₂Cl₂ (2 ml) was added a solution of 4M HCl in dioxan (4 ml) at 0° C. The reaction was stirred at RT for 4 h. The solvent in the reaction was distilled out to afford the required compound as an hydrochloric salt (0.4 g).

(34c) VT-03-00063

To a stirred solution of compound 6-methoxy-4-vinyl-quinoline-3-carbonitrile (0.09 g, 0.427 mmol) and Compound 34b (0.144 g, 0.51 mmol) in DMF (3 ml) was added tetramethyl guanidine (0.05 ml). The reaction was stirred at RT for 3 h. Upon completion, the DMF in the reaction mass was distilled out. The crude was diluted with 5% MeOH—CH₂Cl₂ and washed with water and concentrated under reduced pressure. The obtained crude was purified by preparative TLC to afford the required compound as an off-white solid (0.012 g).

¹HNMR (400 MHz, CDCl₃) δ 8.83 (s, 1H), 8.05 (d, 1H), 7.85 (s, 1H), 7.59 (t, 2H), 7.35 (s, 1H), 7.05 (d, 1H), 3.98 (s, 3H), 3.96 (s, 3H), 3.81 (s, 2H), 3.54 (t, 2H), 3.06 (d, 2H), 3.75 (d, 2H), 2.53-2.57 (m, 1H), 2.25 (t, 2H), 1.98 (d, 2H), 1.53 (d, 2 h). Mass spectra [M+H]+m/z 476.6

(35) Synthesis of VT-03-00064

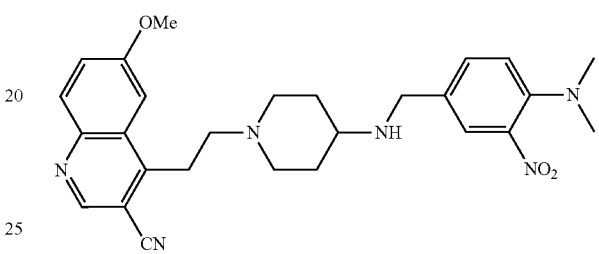

(35a) 4-(4-Dimethylamino-3-nitro-benzylamino)-piperidine-1-carboxylic acid tert-butyl ester To a stirred solution of 4-amino-piperidine-1-carboxylic acid tert-butyl ester (0.3 g, 1.5 mmol) and 4-Dimethyl-amino-3-nitro-benzaldehyde (0.29 g, 1.5 mmol) in ethanol (6 ml) was added Titanium isopropoxide (0.3 ml) at 0° C. and stirred. The reaction was gradually brought to RT and stirred for 16 h. Then sodium borohydride (0.057 g, 1.5 mmol) was added followed by catalytic amount of acetic acid and stirred for 3 h at ambient temperature. Upon completion, the solvents in the reaction were distilled out. The crude was diluted with 10% MeOH—CH₂Cl₂ solution and washed with water. The organic layer was then dried over sodium sulfate and concentrated under reduced pressure. The obtained crude was taken was purified by (100-200 mesh) silicagel column chromatography eluting the required compound with 90% EtOAc-Petether as an yellow solid (0.45 g).

(35b) (4-Dimethylamino-3-nitro-benzyl)-piperidin-4-yl-amine

To a stirred solution of compound 35a (0.45 g) in CH₂Cl₂ (2 ml) was added a solution of 4M HCl in Dioxan (5 ml) at 0° C. The reaction was stirred at RT for 4 h. The solvent in the reaction was distilled out to afford the required compound as an hydrochloric salt (0.35 g).

(35c) VT-03-00064

To a stirred solution of Compound 6-Methoxy-4-vinyl-quinoline-3-carbonitrile (0.09 g, 0.427 mmol) and Compound 35b (0.144 g, 0.51 mmol) in DMF (3 ml) was added Tetramethyl Guanidine (0.05 ml). The reaction was stirred at RT for 3 h. Upon completion, the DMF in the reaction mass was distilled out. The crude was diluted with 5% MeOH—CH₂Cl₂ and washed with water and concentrated under reduced pressure. The obtained crude was purified by preparative TLC to afford the required compound as an off-white solid (0.025 g).

¹HNMR (400 MHz, CDCl₃) δ 8.82 (s, 1H), 8.02 (d, 1H), 7.75 (s, 1H), 7.45 (d, 1H), 7.40 (d, 1H), 7.35 (s, 1H), 7.01 (d, 1H), 4.01 (s, 3H), 3.76 (s, 2H), 3.56 (s, 2H), 3.01 (d, 2H), 2.90 (s, 6H), 2.75 (t, 2 h), 2.54-2.57 (m, 1H), 2.22-2.25 (m, 2H), 1.98 (d, 2H), 1.53 (d, 2H). Mass spectra [M+H]+m/z 489.5

(36) Synthesis of VT-03-00065

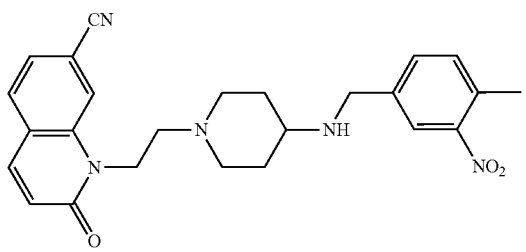 [SMILES: Cc1ccc(CNC2CCN(CCn3c(=O)ccc4ccc(C#N)cc43)CC2)cc1[N+](=O)[O-]]

(36a) 4-Methyl-3-nitro-benzonitrile

To a stirred solution of 4-methylbenzonitrile (10 g, 85.47 mmol) in conc. H₂SO₄ was added fuming nitric acid (6.3 g, 102.5 mmol) at 0° C. The reaction was gradually brought to RT and stirred for 1 h. Upon completion, the reaction was quenched with ice and the obtained solids were filtered. These solids were washed with diethyl ether and dried under vacuum to afford the required compound (8 g) as an off-white solid.

(36b) 3-(4-Cyano-2-nitro-phenyl)-2-oxo-propionic acid ethyl ester

To a stirred solution of compound 36a (20 g, 246.9 mmol) in ethanol (100 ml) was added a solution of sodium ethoxide (24.6 g, 370 mmol) at RT. The reaction was then stirred at RT for 16 h. Upon completion, water was added to the reaction followed by dropwise addition of conc HCl, which resulted in the precipitation of yellow solids. These solids were filtered and washed with diethyl ether to afford the required compound (15 g).

(36c) 3-Hydroxy-2-oxo-1,2,3,4-tetrahydro-quinoline-7-carbonitrile

To a stirred solution of compound 36b (15 g, 57.3 mmol) in ACN (150 ml) was added sodium borohydride (0.6 g, 17.7 mmol) at RT and stirred for 1 h. Then AcOH (8.5 ml) and Fe powder (30 g) were added. The reaction was heated at 70° C. for 1 h. Upon completion, the obtained solids were filtered and washed with water, then with ethanol and dried under vacuum to afford the required compound (10 g) as a red solid.

(36d) 2-Oxo-1,2-dihydro-quinoline-7-carbonitrile

To a stirred solution of compound 36c (0.8 g, 4.3 mmol) in CAN was added DBU (0.971 g, 6.4 mmol) and heated at 75° C. for 3 h. The reaction was cooled to RT and the precipitate was collected by filtration. This precipitate was washed with water, then methanol and dried under vacuum to afford the required compound as a brown solid (0.3 g).

(36e) {1-[2-(7-Methoxy-2-oxo-2H-quinolin-1-yl)-ethyl]-piperidin-4-yl}-carbamic acid tert-butyl ester To a stirred solution of Compound 36d (1 g, 5.7 mmol) in DMF (10 ml) was added 60% NaH at 0° C. and stirred for 1 h. The Compound 25e (1.83 g, 5.7 mmol) in DMF (10 ml) was added dropwise. The reaction was stirred at RT for 16 h. Upon completion, the DMF was distilled out, chilled water was added and extracted with EtOAC. The EtOAC layers were dried over Na₂SO₄ and concentrated under reduced pressure. The obtained crude was purified by (100-200 mesh) silica gel column chromatography eluting the required compound with 3% MeOH—CH₂Cl₂ as a red color semisolid (0.6 g).

(36f) 1-[2-(4-Amino-piperidin-1-yl)-ethyl]-7-methoxy-1H-quinolin-2-one

To a stirred solution of compound 36e (0.6 g) in CH₂Cl₂ (2 ml) was added a solution of 4M HCl in dioxan (5 ml) at 0° C. The reaction was stirred at RT for 4 h. The solvent in the reaction was distilled out to afford the required compound as an hydrochloric salt (0.65 g).

(36 g) VT-03-00065

To a stirred solution of compound 36f (0.2 g, 0.66 mmol) and 4-methyl-3-nitro-benzaldehyde (0.131 g, 0.794 mmol) in ethanol (4 ml) was added titanium isopropoxide (0.2 ml) at 0° C. and stirred. The reaction was gradually brought to RT and stirred for 16 h. Then sodium borohydride (0.049 g, 1.34 mmol) was added followed by catalytic amount of acetic acid and stirred for 3 h at ambient temperature. Upon completion, the solvents in the reaction were distilled out. The crude was diluted with 5% MeOH—CH₂Cl₂ solution and washed with water. The organic layer was then dried over sodium sulfate and concentrated under reduced pressure. The obtained crude was purified by 100-200 mesh-silicagel column chromatography, eluting the required compound with 10% MeOH—CH₂Cl₂. The obtained compound (0.009 g) was confirmed to be the product by mass spectra and 1H-NMR.

¹HNMR (400 MHz, CDCl₃) δ 7.95 (s, 1H), 8.81 (s, 1H), 7.69 (d, 2H), 7.25 (d, 1H), 7.68 (d, 2H), 4.39-4.44 (m, 2H), 3.91 (s, 2H), 3.52 (s, 2H), 3.01 (d, 2H), 2.61 (d, 2H), 2.59 (s, 3H), 2.22-2.25 (m, 2H), 1.96-1.99 (m, 2H), 1.54-1.57 (m, 2H). Mass spectra [M+H]+m/z 446.6

(37) Synthesis of VT-03-00066

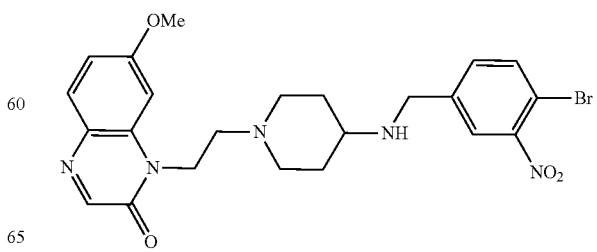

To a stirred solution of compound 26 g (0.2 g, 0.66 mmol) and 4-bromo-3-nitro-benzaldehyde (0.131 g, 0.77 mmol) in ethanol (4 ml) was added titanium isopropoxide (0.2 ml) at 0° C. and stirred. The reaction was gradually brought to RT and stirred for 16 h. Then sodium borohydride (0.049 g, 1.34 mmol) was added followed by catalytic amount of acetic acid and stirred for 3 h at ambient temperature. Upon completion, the solvents in the reaction were distilled out. The crude was diluted with 5% MeOH—CH$_2$Cl$_2$ solution and washed with water. The organic layer was then dried over sodium sulfate and concentrated under reduced pressure. The obtained crude was purified by 100-200 mesh-silicagel column chromatography, eluting the required compound with 7% MeOH—CH$_2$Cl$_2$. The obtained compound (0.023 g) was confirmed to be the product by mass spectra and $^1$H-NMR.

$^1$HNMR (400 MHz, CDCl$_3$) δ 8.35 (s, 1H), 7.86 (d, 2H), 7.65 (d, 1H), 7.42 (d, 1H), 7.20 (d, 1H), 7.18 (s, 1H), 5.75 (d, 2H), 5.26 (d, 1H), 3.90 (s, 3H), 3.86 (s, 2H), 3.50-3.54 (m, 2H), 3.01 (d, 2H), 2.75 (t, 2H), 2.56-2.59 (m, 1H), 1.56 (d, 2H). Mass spectra [M+H]+m/z 517.4

(38) Synthesis of VT-03-00067

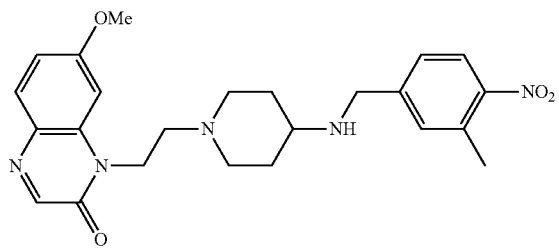

To a stirred solution of compound 26 g (0.2 g, 0.66 mmol) and 3-methyl-4-nitro-benzaldehyde (0.131 g, 0.794 mmol) in ethanol (4 ml) was added titanium isopropoxide (0.2 ml) at 0° C. and stirred. The reaction was gradually brought to RT and stirred for 16 h. Then sodiumborohydride (0.049 g, 1.34 mmol) was added followed by catalytic amount of acetic acid and stirred for 3 h at ambient temperature. Upon completion, the solvents in the reaction were distilled out. The crude was diluted with 5% MeOH—CH$_2$Cl$_2$ solution and washed with water. The organic layer was then dried over sodium sulfate and concentrated under reduced pressure. The obtained crude was purified by 100-200 mesh-silicagel column chromatography, eluting the required compound with 7% MeOH—CH$_2$Cl$_2$. The obtained compound (0.025 g) was confirmed to be the product by mass spectra and $^1$H-NMR.

$^1$HNMR (400 MHz, CDCl$_3$) δ 8.19 (s, 1H), 7.94 (d, 1H), 7.78 (d, 2H), 7.34 (s, 1H), 7.19 (s, 1H), 6.95 (d, 1H), 4.03 (s, 3H), 3.85 (s, 1H), 3.65 (s, 2H), 3.23 (t, 2H), 3.46 (t, 2H), 2.95 (s, 3H), 2.60 (d, 2H), 2.73-2.77 (m, 2H), 1.42 (t, 4H). Mass spectra [M+H]+m/z 452.3

(39) Synthesis of VT-03-00068

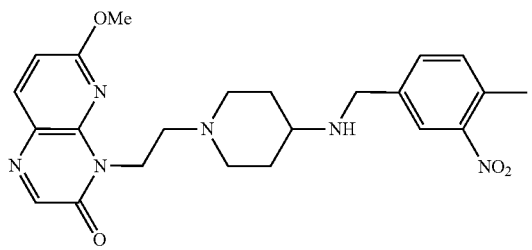 [SMILES: COc1ccc2ncc(=O)n(CCN3CCC(NCc4ccc(C)c([N+](=O)[O-])c4)CC3)c2n1]

(39a) 2,6-Dichloro-3-nitro-pyridine

To a stirred solution of 2,6-dichloropyridine 25 g (171.1 mmol) in conc.H$_2$SO$_4$ was added conc HNO$_3$ at −15° C. dropwise. The reaction was then heated at 150° C. for 4 h. Upon completion, the reaction was cooled to RT and poured into ice water. The obtained solids were filtered and dried under vacuum to afford the required compound as an off-white solid (28 g).

(39b) 6-Chloro-3-nitro-pyridin-2-ylamine

To a stirred solution of Compound 39a (50 g, 261.78 mmol) was added 38% ammonia solution (150 ml) and heated at 50° C. for 5 h. Upon completion, the obtained solids were filtered and given diethylether washings to afford the required compound as a yellow solid (30 g).

(39c) 6-Methoxy-3-nitro-pyridin-2-ylamine

To a stirred solution of Compound 39b (15 g, 86.70 mmol) in MeOH (35 ml) was added NaOMe (7.2 g, 133.92 mmol) at −15° C. and stirred for 16 h at RT. The reaction was quenched with ice and the obtained solids were filtered and dried to afford the required compound (9 g).

(39d) 6-Methoxy-pyridine-2,3-diamine

To a stirred solution of Compound 39c in Conc HCl was added SnCl$_2$ at RT and stirred for 5 h at 50° C. The solvent was evaporated and the solids were filtered. The aqueous layer was basified with dilute NH$_4$OH solution and the obtained solids were filtered to afford the required compound as a black colored solid (4 g).

(39e) 6-Methoxy-4H-pyrido[2,3-b]pyrazin-3-one

To a stirred solution of Compound 39d (4 g, 28.77 mmol) in MeOH (40 ml) was added ethyl glyoxalate (4.4 g, 43.2 mmol) at RT. Upon completion, the reaction was filtered to remove the solids. The filterate was evaporated and the solids thus obtained were washed with diethylether and pentane to afford the required compound (0.3 g) as a yellow solid.

(39f) {1-[2-(6-Methoxy-3-oxo-3H-pyrido[2,3-b]pyrazin-4-yl)-ethyl]-piperidin-4-yl}-carbamic acid tert-butyl ester To a stirred solution of Compound 39e (0.1 g, 0.56 mmol) in DMF (5 ml) was added 60% NaH at 0° C. and stirred for 1 h. The Compound 25e (0.22 g, 0.67 mmol) in DMF (5 ml)

was added dropwise. The reaction was stirred at RT for 16 h. Upon completion, the DMF was distilled out, chilled water was added and extracted with EtOAC. The EtOAC layers were dried over Na$_2$SO$_4$ and concentrated under reduced pressure. The obtained crude was purified by (100-200 mesh) silica gel column chromatography eluting the required compound with 7% MeOH—CH$_2$Cl$_2$ as a red color solid (0.05 g).

(39 g) 4-[2-(4-Amino-piperidin-1-yl)-ethyl]-6-methoxy-4H-pyrido[2,3-b]pyrazin-3-one To a stirred solution of compound 39f (0.05 g) in CH$_2$Cl$_2$ (0.5 ml) was added a solution of 4M HCl in dioxan (1 ml) at 0° C. The reaction was stirred at RT for 4 h. The solvent in the reaction was distilled out to afford the required compound as an hydrochloric salt (0.06 g).

(39 h) VT-03-00068

To a stirred solution of Compound 39 g (0.05 g, 0.13 mmol) and 4-methyl-3-nitro-benzaldehyde (0.024 g, 0.15 mmol) in ethanol (4 ml) was added titanium isopropoxide (0.05 ml) at 0° C. and stirred. The reaction was gradually brought to RT and stirred for 16 h. Then sodiumborohydride (0.009 g, 0.25 mmol) was added followed by catalytic amount of Acetic acid and stirred for 3 h at ambient temperature. Upon completion, the solvents in the reaction were distilled out. The crude was diluted with 5% MeOH—CH$_2$Cl$_2$ solution and washed with water. The organic layer was then dried over sodium sulfate and concentrated under reduced pressure. The obtained crude was purified by 100-200 mesh-silicagel column chromatography, eluting the required compound with 10% MeOH—CH$_2$Cl$_2$. The obtained compound (0.007 g) was confirmed to be the product by Mass spectra. Mass spectra [M+H]+m/z 453.3

(40) Synthesis of VT-03-00069

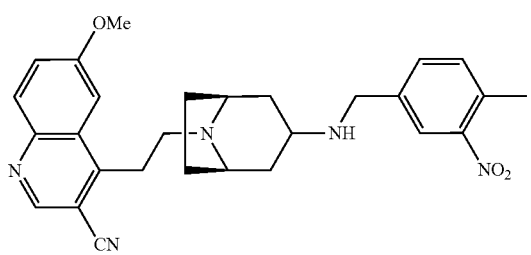 [SMILES: COc1ccc2ncc(C#N)c(CCN3[C@@H]4CC[C@H]3CC(NCc3ccc(C)c([N+](=O)[O-])c3)C4)c2c1]

To a stirred solution of compound 1b (0.25 g, 0.854 mmol) in 1,2-Dichloroethane was added 3-methyl-4-nitrobenzaldehyde (0.118 g, 0.653 mmol), followed by sodium triacetoxy borohydride (0.166 g, 0.783 mmol) and catalytic acetic acid at 0° C. The reaction was brought to RT and stirred for 4 h. Upon completion the solvent in the reaction was distilled out. The crude was partitioned between water and 5% MeOH—CH$_2$Cl$_2$. The organic layers were dried over sodium sulphate and concentrated under reduced pressure. The residue was purified by silicagel preparative TLC eluting with 5% MeOH—CH$_2$Cl$_2$ to afford the required compound VT-03-00069 (12 mg).

$^1$HNMR (400 MHz, CDCl$_3$) δ 8.91 (s, 1H), 8.25 (s, 1H), 8.18 (s, 1H), 8.06 (d, 1H), 7.91 (dd, 1H), 7.42 (dd, 2H), 4.02 (s, 3H), 3.62 (m, 1H), 3.49-3.51 (m, 4H), 3.36 (s, 2H), 2.79 (t, 2H), 2.60 (s, 3H), 2.21-2.24 (m, 4H), 2.01-2.03 (m, 2H), 1.56 (d, 2H). Mass spectra [M+H]+m/z 486.7

(41) Synthesis of VT-03-00070

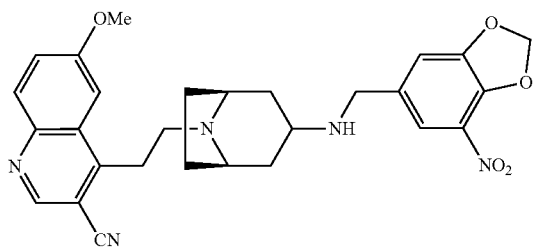 [SMILES: COc1ccc2ncc(C#N)c(CCN3[C@@H]4CC[C@H]3CC(NCc3cc5c(c([N+](=O)[O-])c3)OCO5)C4)c2c1]

(41a) 6-Nitro-benzo[1,3]dioxole-5-carbaldehyde

An ice cold nitration mixture prepared by slow addition of fuming HNO$_3$ (0.7 ml) into an ice cold solution of conc H$_2$SO$_4$ (0.086 mL) was slowly added to an ice cold solution of piperonal (0.2 g, 1.3 mmol) at 0° C. and stirred for 20 minutes. Upon completion, the reaction was quenched with ice and extracted with EtOAc. The organic layers were dried over Na$_2$SO$_4$ and concentrated under reduced pressure. Purification of the crude by (100-200 mesh) silica gel column chromatography eluted the required compound as a red color solid (0.13 g).

(41b) VT-03-00070

To a stirred solution of compound 1b (0.25 g, 0.854 mmol) in 1,2-dichloroethane was added Compound 41a (0.118 g, 0.653 mmol), followed by sodium triacetoxy borohydride (0.166 g, 0.783 mmol) and catalytic acetic acid at 0° C. The reaction was brought to RT and stirred for 4 h. Upon completion the solvent in the reaction was distilled out. The crude was partitioned between water and 5% MeOH—CH$_2$Cl$_2$. The organic layers were dried over sodium sulphate and concentrated under reduced pressure. The residue was purified by silicagel preparative TLC eluting with 5% MeOH—CH$_2$Cl$_2$ to afford the required compound VT-03-00070 (8 mg).

$^1$HNMR (400 MHz, CDCl$_3$) δ 8.85 (s, 1H), 8.09 (d, 1H), 7.53 (d, 2H), 7.48 (s, 1H), 6.25 (s, 1H), 6.18 (s, 2H), 4.09 (s, 3H), 4.11 (s, 2H), 2.88-2.91 (m, 3H), 2.23 (d, 2H), 2.05 (d, 3H), 1.42 (m, 3H), 1.36 (m, 4H). Mass spectra [M+H]+m/z 516.8

(42) Synthesis of VT-03-00071

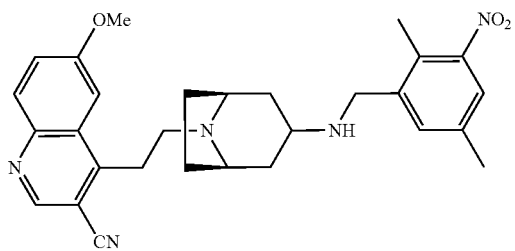 [SMILES: COc1ccc2ncc(C#N)c(CCN3[C@@H]4CC[C@H]3CC(NCc3cc(C)cc([N+](=O)[O-])c3C)C4)c2c1]

(42a) 2,5-Dimethyl-3-nitro-benzoic acid methyl ester

An ice cold nitration mixture prepared by slow addition of fuming $HNO_3$ (45.5 mL) into an ice cold solution of conc $H_2SO_4$ (5.6 mL) was slowly added to an ice cold solution of 2,5-dimethyl-benzoic acid methyl ester (14.0 g, 85.3 mmol) at 0° C. and stirred for 20 minutes. Upon completion, the reaction was quenched with ice and extracted with EtOAc. The organic layers were dried over $Na_2SO_4$ and concentrated under reduced pressure. Purification of the crude by (100-200 mesh) silicagel column chromatography eluted the required compound as a yellow color liquid (22 g).

(42b) 2,5-Dimethyl-3-nitro-benzaldehyde

To a stirred solution of compound 52a (0.2 g, 0.95 mmol) in dry THF (5 mL) was added DIBAL-H (1.0M in toluene, 1.04 mL) at −78° C. and stirred for 1 h. Upon completion, the reaction was quenched with excess MeOH and a saturated solution of potassium sodium tartrate was added to the reaction. The aqueous layer was extracted with EtOAC. These organic layers were dried over $Na_2SO_4$ and concentrated under reduced pressure. Purification of the crude by (100-200 mesh) silica gel column chromatography eluted the required compound with 40% EtOAc-petether to afford the required compound as an off white solid (0.05 g).

(42c) VT-03-00071

To a stirred solution of compound 1b (0.12 g, 0.356 mmol) in 1,2-dichloroethane was added Compound 50b (0.06 g, 0.356 mmol), followed by sodium triacetoxy borohydride (0.09 g, 0.43 mmol) and catalytic acetic acid at 0° C. The reaction was brought to RT and stirred for 4 h. Upon completion the solvent in the reaction was distilled out. The crude was partitioned between water and 5% MeOH—$CH_2Cl_2$. The organic layers were dried over sodium sulphate and concentrated under reduced pressure. The residue was purified by silicagel preparative TLC eluting with 5% MeOH—$CH_2Cl_2$ to afford the required compound VT-03-00071 (10 mg). Mass spectra [M+H]+m/z 500.5

(43) Synthesis of VT-03-00072

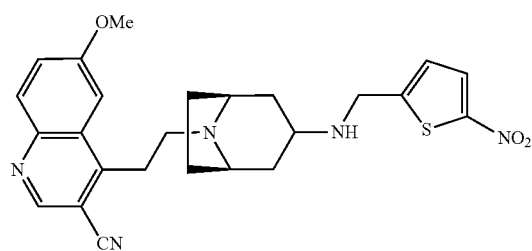 [SMILES: COc1ccc2ncc(C#N)c(CCN3[C@@H]4CC[C@H]3CC(NCc3ccc([N+](=O)[O-])s3)C4)c2c1]

To a stirred solution of compound 1b (0.25 g, 0.854 mmol) in 1,2-dichloroethane was added 5-nitro-thiophene-2-carbaldehyde (0.134 g, 0.854 mmol), followed by sodium triacetoxy borohydride (0.098 g, 1.02 mmol) and catalytic acetic acid at 0° C. The reaction was brought to RT and stirred for 4 h. Upon completion the solvent in the reaction was distilled out. The crude was partitioned between water and 5% MeOH—$CH_2Cl_2$. The organic layers were dried over sodium sulphate and concentrated under reduced pressure. The residue was purified by silicagel preparative TLC eluting with 5% MeOH—$CH_2Cl_2$ to afford the required compound VT-03-00072 (16 mg).

$^1$HNMR (400 MHz, $CDCl_3$) δ 8.91 (s, 1H), 8.41 (s, 1H), 8.10 (s, 1H), 8.02 (d, 1H), 7.61 (d, 1H), 7.56 (s, 1H), 7.49 (s, 1H), 4.02 (s, 3H), 3.56 (s, 1H), 3.45 (t, 2H), 3.21 (s, 2H), 2.75 (t, 2H), 2.15 (d, 2H), 1.95 (t, 2H), 1.90 (t, 2H), 1.45 (d, 2H). Mass spectra [M+H]+m/z 478.6

(44) Synthesis of VT-03-00074

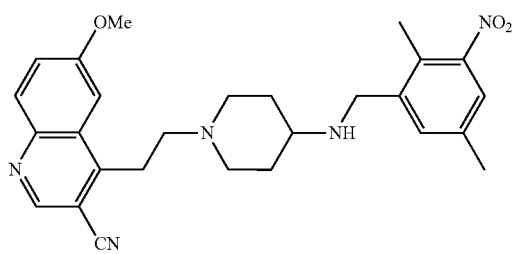 [SMILES: COc1ccc2ncc(C#N)c(CCN3CCC(NCc4cc(C)cc([N+](=O)[O-])c4C)CC3)c2c1]

(44a) 4-(2,5-Dimethyl-3-nitro-benzylamino)-piperidine-1-carboxylic acid tert-butyl ester To a stirred solution of 4-amino-piperidine-1-carboxylic acid tert-butyl ester (0.15 g, 0.75 mmol) and 2,5-dimethyl-3-nitro-benzaldehyde (0.135 g, 0.75 mmol) in ethanol (6 ml) was added titanium isopropoxide (0.15 ml) at 0° C. and stirred. The reaction was gradually brought to RT and stirred for 16 h. Then sodiumborohydride (0.028 g, 0.75 mmol) was added followed by catalytic amount of acetic acid and stirred for 3 h at ambient temperature. Upon completion, the solvents in the reaction were distilled out. The crude was diluted with 10% MeOH—$CH_2Cl_2$ solution and washed with water. The organic layer was then dried over sodium sulfate and concentrated under reduced pressure. The obtained crude was taken was purified by (100-200 mesh) silicagel column chromatography eluting the required compound with 70% EtOAc-hexane as a yellow solid (0.25 g).

(44b) (2,5-Dimethyl-3-nitro-benzyl)-piperidin-4-yl-amine

To a stirred solution of compound 54a (0.25 g) in $CH_2Cl_2$ (2 ml) was added a solution of 4M HCl in dioxan (2.5 ml) at 0° C. The reaction was stirred at RT for 4 h. The solvent in the reaction was distilled out to afford the required compound as an hydrochloric salt (0.31 g).

(44c) VT-03-00074

To a stirred solution of compound 6-methoxy-4-vinyl-quinoline-3-carbonitrile (0.2 g, 0.95 mmol) and Compound 44b (0.31 g, 1.14 mmol) in DMF (10 ml) was added tetramethyl guanidine (0.1 ml). The reaction was stirred at RT for 3 h. Upon completion, the DMF in the reaction mass was distilled out. The crude was diluted with 5% MeOH—$CH_2Cl_2$ and washed with water and concentrated under reduced pressure. The obtained crude was purified by preparative TLC to afford the required compound as an off-white solid (0.03 g).

$^1$HNMR (400 MHz, $CDCl_3$) δ 8.81 (s, 1H), 8.06 (d, 1H), 7.51 (d, 2H), 7.38 (d, 2H), 3.98 (s, 3H), 3.80 (s, 2H), 3.5 (s,

6H), 3.09 (d, 2H), 2.76-2.80 (m, 2H), 2.58-2.62 (m, 2H), 2.4 (s, 3H), 2.32 (s, 3H), 2.22-2.25 (m, 2H), 1.92 (d, 2H). Mass spectra [M+H]+ at m/z 474.3

(45) Synthesis of VT-03-00075

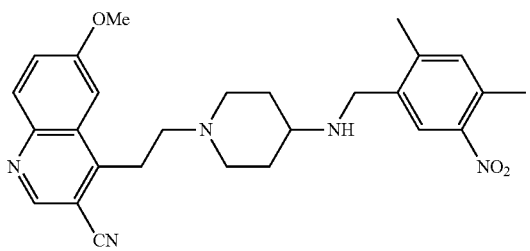

(45a) 4-(2,4-Dimethyl-5-nitro-benzylamino)-piperidine-1-carboxylic acid tert-butyl ester To a stirred solution of 4-amino-piperidine-1-carboxylic acid tert-butyl ester (0.225 g, 1.125 mmol) and (2,4-Dimethyl-5-nitro-benzyl)-piperidin-4-yl-amine (0.203 g, 1.125 mmol) in ethanol (6 ml) was added titanium isopropoxide (0.22 ml) at 0° C. and stirred. The reaction was gradually brought to RT and stirred for 16 h. Then sodium borohydride (0.043 g, 1.125 mmol) was added followed by catalytic amount of acetic acid and stirred for 3 h at ambient temperature. Upon completion, the solvents in the reaction were distilled out. The crude was diluted with 10% MeOH—CH$_2$Cl$_2$ solution and washed with water. The organic layer was then dried over sodium sulfate and concentrated under reduced pressure. The obtained crude was taken was purified by (100-200 mesh) silicagel column chromatography eluting the required compound with 70% EtOAc-petether as a yellow solid (0.3 g).

(45b) (2,4-Dimethyl-5-nitro-benzyl)-piperidin-4-yl-amine

To a stirred solution of compound 45a (0.03 g) in CH$_2$Cl$_2$ (3 ml) was added a solution of 4M HCl in dioxan (2.5 ml) at 0° C. The reaction was stirred at RT for 4 h. The solvent in the reaction was distilled out to afford the required compound as an hydrochloric salt (0.38 g).

(45c) VT-03-00075

To a stirred solution of Compound 6-methoxy-4-vinyl-quinoline-3-carbonitrile (0.25 g, 1.19 mmol) and Compound 45b (0.23 g, 1.42 mmol) in DMF (3 ml) was added tetramethyl guanidine (0.1 ml). The reaction was stirred at RT for 3 h. Upon completion, the DMF in the reaction mass was distilled out. The crude was diluted with 5% MeOH—CH$_2$Cl$_2$ and washed with water and concentrated under reduced pressure. The obtained crude was purified by preparative TLC to afford the required compound as an pale green solid (0.110 g).

$^1$HNMR (400 MHz, CDCl$_3$) δ 8.81 (s, 1H), 8.09 (d, 1H), 8.02 (s, 1H), 7.56 (d, 1H), 7.35 (s, 1H), 7.17 (s, 1H), 3.96 (s, 3H), 3.75 (s, 2H), 3.50-3.53 (m, 2H), 3.01 (d, 2H), 2.75 (t, 2H), 2.57-2.60 (m, 1H), 2.56 (s, 3H), 2.39 (s, 2H), 2.30-2.32 (m, 3H), 1.95 (d, 2H), 1.56 (d, 2H). Mass spectra [M+H]+ m/z 474.2

(46) Synthesis of VT-03-00076

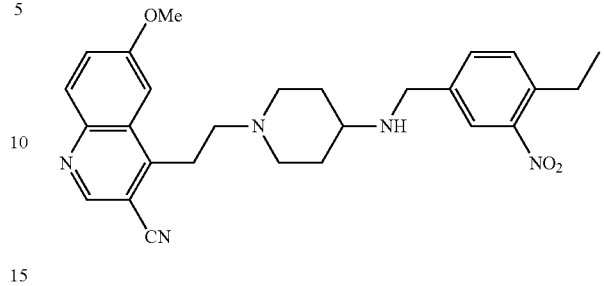

(46a) 4-(4-Ethyl-3-nitro-benzylamino)-piperidine-1-carboxylic acid tert-butyl ester To a stirred solution of 4-amino-piperidine-1-carboxylic acid tert-butyl ester (0.25 g, 1.25 mmol) and 4-ethyl-3-nitro-benzaldehyde (0.225 g, 1.25 mmol) in ethanol (6 ml) was added titanium isopropoxide (0.25 ml) at 0° C. and stirred. The reaction was gradually brought to RT and stirred for 16 h. Then sodium borohydride (0.047 g, 1.25 mmol) was added followed by catalytic amount of acetic acid and stirred for 3 h at ambient temperature. Upon completion, the solvents in the reaction were distilled out. The crude was diluted with 10% MeOH—CH$_2$Cl$_2$ solution and washed with water. The organic layer was then dried over sodium sulfate and concentrated under reduced pressure. The obtained crude was taken was purified by (100-200 mesh) silicagel column chromatography eluting the required compound with 70% EtOAc-petether as an yellow solid (0.26 g).

(46b) (4-Ethyl-3-nitro-benzyl)-piperidin-4-yl-amine

To a stirred solution of compound 46a (0.25 g) in CH$_2$Cl$_2$ (3 ml) was added a solution of 4M HCl in dioxan (2.5 ml) at 0° C. The reaction was stirred at RT for 4 h. The solvent in the reaction was distilled out to afford the required compound as an hydrochloric salt (0.22 g).

(46c) VT-03-00076

To a stirred solution of Compound 6-methoxy-4-vinyl-quinoline-3-carbonitrile (0.24 g, 1.19 mmol) and Compound 46b (0.23 g, 1.42 mmol) in DMF (3 ml) was added tetramethyl guanidine (0.1 ml). The reaction was stirred at RT for 3 h. Upon completion, the DMF in the reaction mass was distilled out. The crude was diluted with 5% MeOH—CH$_2$Cl$_2$ and washed with water and concentrated under reduced pressure. The obtained crude was purified by preparative TLC to afford the required compound as an pale green solid (0.025 g).

$^1$HNMR (400 MHz, CDCl$_3$) δ 8.86 (s, 1H), 8.12 (d, 1H), 7.91 (s, 1H), 7.56 (d, 2H), 7.32 (d, 2H), 4.01 (s, 3H), 3.89 (s, 2H), 3.51 (t, 2H), 3.09 (d, 2H), 2.91 (q, 2H), 2.75 (t, 2H), 2.54-2.58 (m, 1H), 2.24 (t, 2H), 1.92 (d, 2H), 1.53 (q, 2H), 1.31 (t, 3H). Mass spectra [M+H]+ m/z 499.2

(47) Synthesis of VT-03-00077

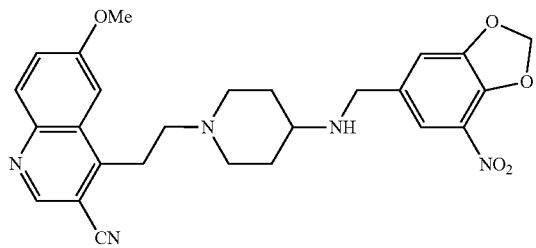 [SMILES: COc1ccc2ncc(C#N)c(CCN3CCC(NCc4cc5c(c([N+](=O)[O-])c4)OCO5)CC3)c2c1]

(47a) 4-[(8-Nitro-2,3-dihydro-benzo[1.4]dioxin-6-ylmethyl)-amino]-piperidine-1-carboxylic acid tert-butyl ester To a stirred solution of 4-amino-piperidine-1-carboxylic acid tert-butyl ester (0.2 g, 1.0 mmol) and 8-nitro-2,3-dihydro-benzo[1,4]dioxine-6-carbaldehyde (0.2 g, 1.0 mmol) in ethanol (6 ml) was added titanium isopropoxide (0.2 ml) at 0° C. and stirred. The reaction was gradually brought to RT and stirred for 16 h. Then sodium borohydride (0.034 g, 1.25 mmol) was added followed by catalytic amount of Acetic acid and stirred for 3 h at ambient temperature. Upon completion, the solvents in the reaction were distilled out. The crude was diluted with 10% MeOH—$CH_2Cl_2$ solution and washed with water. The organic layer was then dried over sodium sulfate and concentrated under reduced pressure. The obtained crude was taken was purified by (100-200 mesh) silicagel column chromatography eluting the required compound with 70% EtOAc-hexane as an yellow solid (0.1 g).

(47b) (8-Nitro-2,3-dihydro-benzo[1,4]dioxin-6-ylmethyl)-piperidin-4-yl-amine To a stirred solution of compound 47a (0.1 g) in $CH_2Cl_2$ (1 ml) was added a solution of 4M HCl in dioxan (1 ml) at 0° C. The reaction was stirred at RT for 3 h. The solvent in the reaction was distilled out to afford the required compound as an hydrochloric salt (0.1 g).

(47c) VT-03-00077

To a stirred solution of Compound 6-methoxy-4-vinyl-quinoline-3-carbonitrile (0.06 g, 1.19 mmol) and Compound 47b (0.099 g, 1.42 mmol) in DMF (3 ml) was added tetramethyl guanidine (0.1 ml). The reaction was stirred at RT for 3 h. Upon completion, the DMF in the reaction mass was distilled out. The crude was diluted with 5% MeOH—$CH_2Cl_2$ and washed with water and concentrated under reduced pressure. The obtained crude was purified by preparative TLC to afford the required compound as an pale green solid (0.01 g).

$^1$HNMR (400 MHz, $CDCl_3$) δ 8.86 (s, 1H), 8.02 (d, 1H), 7.82 (s, 1H), 7.46 (d, 1H), 7.21 (s, 1H), 7.02 (s, 1H), 6.12 (s, 2H), 4.03 (s, 3H), 3.96 (s, 2H), 2.95 (t, 2H), 2.86 (t, 2H), 2.54 (m, 1H), 2.42 (t, 2H), 2.40 (t, 2H), 2.40 (t, 2H), 1.62 (t, 2H), 1.54 (t, 2H). Mass spectra [M+H]+m/z 490.2

(48) Synthesis of VT-03-00078

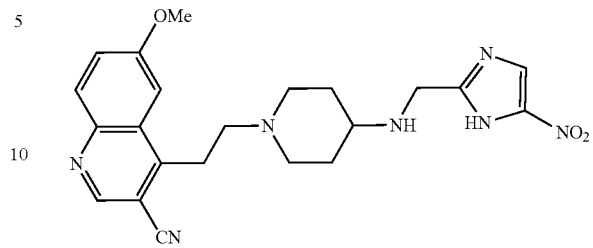

(48a) 4-[(5-Nitro-1H-imidazol-2-ylmethyl)-amino]-piperidine-1-carboxylic acid tert-butyl ester To a stirred solution of 4-amino-piperidine-1-carboxylic acid tert-butyl ester (0.2 g, 1.0 mmol) and 5-Nitro-1H-imidazole-2-carbaldehyde (0.2 g, 1.0 mmol) in ethanol (6 ml) was added titanium isopropoxide (0.2 ml) at 0° C. and stirred. The reaction was gradually brought to RT and stirred for 16 h. Then sodiumborohydride (0.034 g, 1.25 mmol) was added followed by catalytic amount of acetic acid and stirred for 3 h at ambient temperature. Upon completion, the solvents in the reaction were distilled out. The crude was diluted with 10% MeOH—$CH_2Cl_2$ solution and washed with water. The organic layer was then dried over sodium sulfate and concentrated under reduced pressure. The obtained crude was taken was purified by (100-200 mesh) silicagel column chromatography eluting the required compound with 90% EtOAc-petether as an yellow solid (0.23 g).

(48b) (5-Nitro-1H-imidazol-2-ylmethyl)-piperidin-4-yl-amine

To a stirred solution of compound 48a (0.1 g) in $CH_2Cl_2$ (1 ml) was added a solution of 4M HCl in dioxan (1 ml) at 0° C. The reaction was stirred at RT for 3 h. The solvent in the reaction was distilled out to afford the required compound as an hydrochloric salt (0.2 g).

(48c) VT-03-00078

To a stirred solution of Compound 6-methoxy-4-vinyl-quinoline-3-carbonitrile (0.06 g, 1.19 mmol) and Compound 48b (0.099 g, 1.42 mmol) in DMF (3 ml) was added tetramethyl guanidine (0.1 ml). The reaction was stirred at RT for 3 h. Upon completion, the DMF in the reaction mass was distilled out. The crude was diluted with 5% MeOH—$CH_2Cl_2$ and washed with water and concentrated under reduced pressure. The obtained crude was purified by preparative TLC to afford the required compound as an pale brown solid (0.006 g). Mass spectra [M+H]+m/z 436.3

(49) Synthesis of VT-03-00079

(50) Synthesis of VT-03-00080

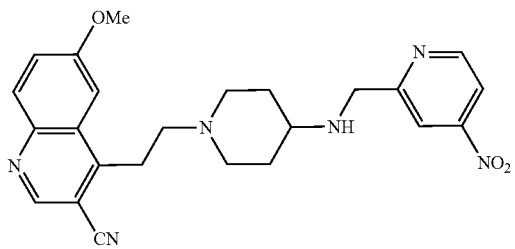 [SMILES: COc1ccc2ncc(C#N)c(CCN3CCC(NCc4cc([N+](=O)[O-])ccn4)CC3)c2c1]

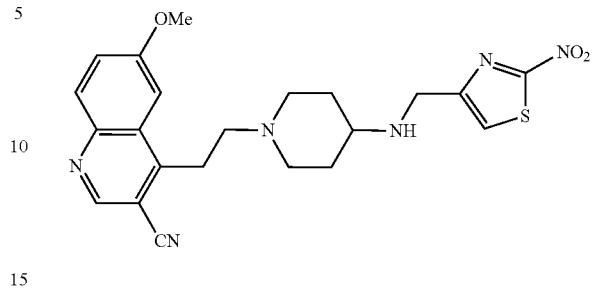

(49a) 4-[(4-Nitro-pyridin-2-ylmethyl)-amino]-piperidine-1-carboxylic acid tert-butyl ester To a stirred solution of 4-amino-piperidine-1-carboxylic acid tert-butyl ester (0.25 g, 1.25 mmol) and 4-nitro-pyridine-2-carbaldehyde (0.19 g, 1.25 mmol) in ethanol (6 ml) was added titanium isopropoxide (0.25 ml) at 0° C. and stirred. The reaction was gradually brought to RT and stirred for 16 h. Then sodium borohydride (0.047 g, 1.25 mmol) was added followed by catalytic amount of acetic acid and stirred for 3 h at ambient temperature. Upon completion, the solvents in the reaction were distilled out. The crude was diluted with 10% MeOH—$CH_2Cl_2$ solution and washed with water. The organic layer was then dried over sodium sulfate and concentrated under reduced pressure. The obtained crude was taken was purified by (100-200 mesh) silicagel column chromatography eluting the required compound with 70% EtOAc-petether as a yellow solid (0.1 g).

(49b) (4-Nitro-pyridin-2-ylmethyl)-piperidin-4-yl-amine

To a stirred solution of compound 49a (0.25 g) in $CH_2Cl_2$ (2 ml) was added a solution of 4M HCl in dioxan (1 ml) at 0° C. The reaction was stirred at RT for 3 h. The solvent in the reaction was distilled out to afford the required compound as an hydrochloric salt (0.35 g).

(49c) VT-03-00079

To a stirred solution of compound 6-methoxy-4-vinyl-quinoline-3-carbonitrile (0.25 g, 1.19 mmol) and Compound 49b (0.337 g, 1.42 mmol) in DMF (5 ml) was added tetramethyl guanidine (0.1 ml). The reaction was stirred at RT for 3 h. Upon completion, the DMF in the reaction mass was distilled out. The crude was diluted with 5% MeOH—$CH_2Cl_2$ and washed with water and concentrated under reduced pressure. The obtained crude was purified by preparative TLC to afford the required compound as an pale brown solid (0.02 g).

$^1$HNMR (400 MHz, $CDCl_3$) δ 8.89 (d, 1H), 8.81 (s, 1H), 8.14 (s, 1H), 8.05 (d, 1H), 7.80-7.84 (m, 1H), 7.51 (d, 1H), 7.35 (s, 1H), 4.12 (s, 2H), 3.96 (s, 3H), 3.49-3.52 (m, 2H), 3.06-3.10 (m, 2H), 2.76 (t, 2H) 2.56-2.61 (m, 1H), 2.24 (t, 2H), 1.94 (d, 2H), 1.52 (d, 2H). Mass spectra [M+H]+m/z 447.4

(50a) 4-[(2-Nitro-thiazol-4-ylmethyl)-amino]-piperidine-1-carboxylic acid tert-butyl ester To a stirred solution of 4-amino-piperidine-1-carboxylic acid tert-butyl ester (0.2 g, 1.0 mmol) and 2-nitro-thiazole-4-carbaldehyde (0.14 g, 1.0 mmol) in ethanol (6 ml) was added titanium isopropoxide (0.2 ml) at 0° C. and stirred. The reaction was gradually brought to RT and stirred for 16 h. Then sodium borohydride (0.038 g, 1.0 mmol) was added followed by catalytic amount of acetic acid and stirred for 3 h at ambient temperature. Upon completion, the solvents in the reaction were distilled out. The crude was diluted with 10% MeOH—$CH_2Cl_2$ solution and washed with water. The organic layer was then dried over sodium sulfate and concentrated under reduced pressure. The obtained crude was taken was purified by (100-200 mesh) silicagel column chromatography eluting the required compound with 80% EtOAc-petether as an yellow solid (0.2 g).

(50b) (2-Nitro-thiazol-4-ylmethyl)-piperidin-4-yl-amine

To a stirred solution of compound 50a (0.2 g) in $CH_2Cl_2$ (1 ml) was added a solution of 4M HCl in dioxan (1.5 ml) at 0° C. The reaction was stirred at RT for 3 h. The solvent in the reaction was distilled out to afford the required compound as an hydrochloric salt (0.1 g).

(50c) VT-03-00080

To a stirred solution of Compound 6-methoxy-4-vinyl-quinoline-3-carbonitrile (0.1 g, 0.48 mmol) and Compound 50b (0.110 g, 0.476 mmol) in DMF (5 ml) was added tetramethyl guanidine (0.1 ml). The reaction was stirred at RT for 3 h. Upon completion, the DMF in the reaction mass was distilled out. The crude was diluted with 2.5% MeOH—$CH_2Cl_2$ and washed with water and concentrated under reduced pressure. The obtained crude was purified by preparative TLC to afford the required compound as an pale brown solid (0.02 g).

$^1$HNMR (400 MHz, $CDCl_3$) δ 8.81 (s, 1H), 8.02 (d, 1H), 7.52 (d, 1H), 7.41 (m, 1H), 7.02 (d, 1H), 4.01 (s, 3H), 3.91 (d, 2H), 3.50-3.53 (m, 2H), 3.14-3.18 (m, 2H), 2.75 (t, 2H), 2.54-2.58 (m, 1H), 2.10-2.42 (m, 2H), 1.93-1.97 (t, 2H), 1.48-1.51 (m, 2H). Mass spectra [M+H]+m/z 452.6

(51) Synthesis of VT-03-00081

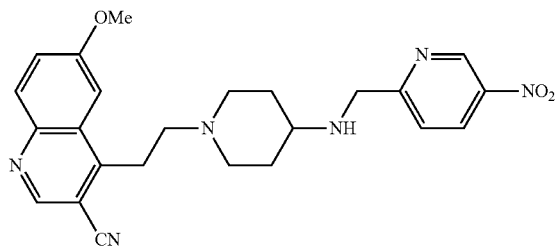

(51a) 4-[(5-Nitro-pyridin-2-ylmethyl)-amino]-piperidine-1-carboxylic acid tert-butyl ester To a stirred solution of 4-amino-piperidine-1-carboxylic acid tert-butyl ester (0.35 g, 1.75 mmol) and 5-nitro-pyridine-2-carbaldehyde (0.27 g, 1.75 mmol) in ethanol (6 ml) was added titanium isopropoxide (0.35 ml) at 0° C. and stirred. The reaction was gradually brought to RT and stirred for 16 h. Then sodium borohydride (0.066 g, 1.75 mmol) was added followed by catalytic amount of acetic acid and stirred for 3 h at ambient temperature. Upon completion, the solvents in the reaction were distilled out. The crude was diluted with 10% MeOH—$CH_2Cl_2$ solution and washed with water. The organic layer was then dried over sodium sulfate and concentrated under reduced pressure. The obtained crude was taken was purified by (100-200 mesh) silicagel column chromatography eluting the required compound with 7% MeOH—$CH_2Cl_2$ as a brown solid (0.35 g).

(51b) (5-Nitro-pyridin-2-ylmethyl)-piperidin-4-yl-amine

To a stirred solution of compound 51a (0.2 g) in $CH_2Cl_2$ (1 ml) was added a solution of 4M HCl in dioxan (1.5 ml) at 0° C. The reaction was stirred at RT for 3 h. The solvent in the reaction was distilled out to afford the required compound as an hydrochloric salt (0.1 g).

(51c) VT-03-00081

To a stirred solution of Compound 6-methoxy-4-vinyl-quinoline-3-carbonitrile (0.1 g, 0.48 mmol) and Compound 51b (0.110 g, 0.476 mmol) in DMF (5 ml) was added tetramethyl guanidine (0.1 ml). The reaction was stirred at RT for 3 h. Upon completion, the DMF in the reaction mass was distilled out. The crude was diluted with 2.5% MeOH—$CH_2Cl_2$ and washed with water and concentrated under reduced pressure. The obtained crude was purified by preparative TLC to afford the required compound as a pale brown solid (0.02 g).

$^1$HNMR (400 MHz, $CDCl_3$) δ 9.1 (s, 1H), 8.75 (d, 1H), 8.52 (s, 1H), 7.83 (s, 1H), 7.43 (d, 1H), 7.23 (d, 2H), 4.26 (s, 2H), 4.06 (s, 3H), 3.75 (s, 4H), 3.24 (m, 2H), 3.02-3.04 (m, 1H), 2.75 (t, 2H), 2.46- 2.51 (m, 2H), 2.23-2.26 (m, 2H), 1.95 (t, 2H), 1.46-1.50 (m, 2H). Mass spectra [M+H]+m/z 447.3

(52) Synthesis of VT-03-00083

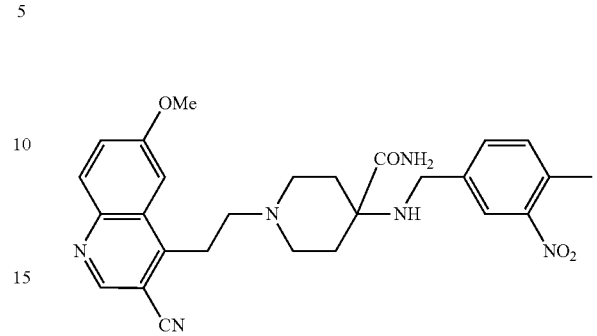

(52a) 4-Carbamoyl-4-(4-methyl-3-nitro-benzylamino)piperidine-1-carboxylicacid tert-butyl ester To a stirred solution of 4-amino-piperidine-4-carboxylic acid amide (0.35 g, 1.75 mmol) and 4-methyl-3-nitro-benzaldehyde (0.27 g, 1.75 mmol) in ethanol (6 ml) was added titanium isopropoxide (0.35 ml) at 0° C. and stirred. The reaction was gradually brought to RT and stirred for 16 h. Then sodium borohydride (0.066 g, 1.75 mmol) was added followed by catalytic amount of acetic acid and stirred for 3 h at ambient temperature. Upon completion, the solvents in the reaction were distilled out. The crude was diluted with 10% MeOH—$CH_2Cl_2$ solution and washed with water. The organic layer was then dried over Sodium sulfate and concentrated under reduced pressure. The obtained crude was taken was purified by (100-200 mesh) silicagel column chromatography eluting the required compound with 7% MeOH—$CH_2Cl_2$ as a brown solid (0.35 g).

(52b) 4-(4-Methyl-3-nitro-benzylamino)-piperidine-4-carboxylic acid amide

To a stirred solution of compound 52a (0.2 g) in $CH_2Cl_2$ (1 ml) was added a solution of 4M HCl in dioxan (1.5 ml) at 0° C. The reaction was stirred at RT for 3 h. The solvent in the reaction was distilled out to afford the required compound as an hydrochloric salt (0.1 g).

(52c) VT-03-00083

To a stirred solution of Compound 6-methoxy-4-vinyl-quinoline-3-carbonitrile (0.1 g, 0.48 mmol) and Compound 52b (0.110 g, 0.476 mmol) in DMF (5 ml) was added tetramethyl guanidine (0.1 ml). The reaction was stirred at RT for 3 h. Upon completion, the DMF in the reaction mass was distilled out. The crude was diluted with 2.5% MeOH—$CH_2Cl_2$ and washed with water and concentrated under reduced pressure. The obtained crude was purified by preparative TLC to afford the required compound as an pale brown solid (0.01 g). Mass spectra [M+H]+m/z 503.2

(53) Synthesis of VT-03-00084

(54) Synthesis of VT-03-00085

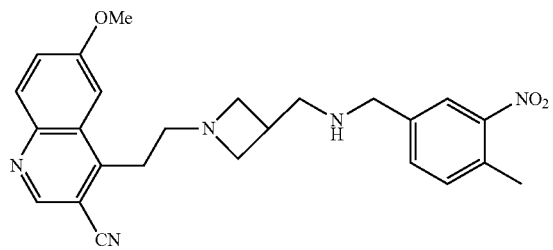 [SMILES: COc1ccc2ncc(C#N)c(CCN3CC(CNCc4ccc(C)c([N+](=O)[O-])c4)C3)c2c1]

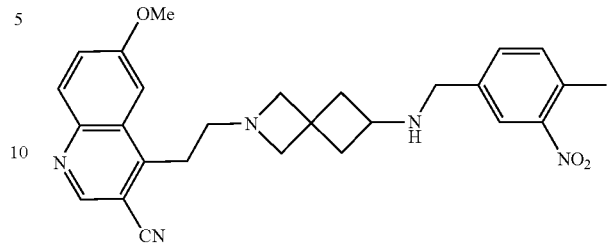

(53a) 3-(4-Methyl-3-nitro-benzylamino)-azetidine-1-carboxylic acid tert-butyl ester:

To a stirred solution of 3-amino-azetidine-1-carboxylic acid tert-butyl ester (0.35 g, 1.97 mmol) and 4-methyl-3-nitro-benzaldehyde (0.327 g, 1.97 mmol) in ethanol (6 ml) was added titanium isopropoxide (0.35 ml) at 0° C. and stirred. The reaction was gradually brought to RT and stirred for 16 h. Then sodium borohydride (0.078 g, 1.97 mmol) was added followed by catalytic amount of acetic acid and stirred for 3 h at ambient temperature. Upon completion, the solvents in the reaction were distilled out. The crude was diluted with 10% MeOH—$CH_2Cl_2$ solution and washed with water. The organic layer was then dried over sodium sulfate and concentrated under reduced pressure. The obtained crude was taken was purified by (100-200 mesh) silicagel column chromatography eluting the required compound with 3% MeOH—$CH_2Cl_2$ as a brown solid (0.32 g).

(53b) Azetidin-3-yl-(4-methyl-3-nitro-benzyl)-amine

To a stirred solution of compound 53a (0.32 g) in $CH_2Cl_2$ (2 ml) was added a solution of 4M HCl in dioxan (3 ml) at 0° C. The reaction was stirred at RT for 3 h. The solvent in the reaction was distilled out to afford the required compound as an hydrochloric salt (0.19 g).

(53c) VT-03-00084

To a stirred solution of compound 6-methoxy-4-vinyl-quinoline-3-carbonitrile (15 g, 0.72 mmol) and Compound 53b (0.15 g, 0.476 mmol) in DMF (5 ml) was added tetramethyl guanidine (0.1 ml). The reaction was stirred at RT for 3 h. Upon completion, the DMF in the reaction mass was distilled out. The crude was diluted with 10% MeOH—$CH_2Cl_2$ and washed with water and concentrated under reduced pressure. The obtained crude was purified by preparative TLC to afford the required compound as a yellow solid (0.01 g).

$^1$HNMR (400 MHz, $CDCl_3$) δ 8.91 (s, 1H), 8.05 (d, 1H), 7.95 (s, 1H), 7.50-7.65 (m, 2H), 7.42 (d, 1H), 7.31 (s, 1H), 4.03 (s, 3H), 3.82 (s, 2H), 3.65-3.39 (m, 6H), 2.72 (t, 2H), 2.65 (t, 2H), 2.42-2.36 (m, 2H), 2.23 (s, 3H), 1.51 (s, 1H). Mass spectra [M+H]+m/z 446.6

(54a) 6-(4-Methyl-3-nitro-benzylamino)-2-aza-spiro[3.3]heptane-2-carboxylic acid tert-butyl ester To a stirred solution of 3-amino-azetidine-1-carboxylic acid tert-butyl ester (0.35 g, 1.97 mmol) and 4-methyl-3-nitro-benzaldehyde (0.327 g, 1.97 mmol) in ethanol (6 ml) was added titanium isopropoxide (0.35 ml) at 0° C. and stirred. The reaction was gradually brought to RT and stirred for 16 h. Then Sodiumborohydride (0.078 g, 1.97 mmol) was added followed by catalytic amount of acetic acid and stirred for 3 h at ambient temperature. Upon completion, the solvents in the reaction were distilled out. The crude was diluted with 10% MeOH—$CH_2Cl_2$ solution and washed with water. The organic layer was then dried over Sodium sulfate and concentrated under reduced pressure. The obtained crude was taken was purified by (100-200 mesh) silica gel column chromatography eluting the required compound with 3% MeOH—$CH_2Cl_2$ as a brown solid (0.32 g).

(54b) (2-Aza-spiro[3.3]hept-6-yl)-(4-methyl-3-nitro-benzyl)-amine

To a stirred solution of compound 54a (0.32 g) in $CH_2Cl_2$ (2 ml) was added a solution of 4M HCl in dioxan (3 ml) at 0° C. The reaction was stirred at RT for 3 h. The solvent in the reaction was distilled out to afford the required compound as an hydrochloric salt (0.19 g).

(54c) VT-03-00085

To a stirred solution of compound 6-methoxy-4-vinyl-quinoline-3-carbonitrile (0.13 g, 0.62 mmol) and Compound 54b (0.16 g, 0.62 mmol) in DMF (3 ml) was added tetramethyl guanidine (0.1 ml). The reaction was stirred at RT for 3 h. Upon completion, the DMF in the reaction mass was distilled out. The crude was diluted with 10% MeOH—$CH_2Cl_2$ and washed with water and concentrated under reduced pressure. The obtained crude was purified by preparative TLC to afford the required compound as a yellow solid (0.01 g). Mass spectra [M+H]+m/z 472.6

(55) Synthesis of VT-03-00086

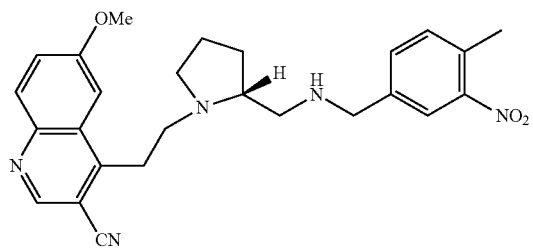 [SMILES: COc1ccc2ncc(C#N)c(CCN3CCC[C@@H]3CNCc3ccc(C)c([N+](=O)[O-])c3)c2c1]

(55a) 3-[(4-Methyl-3-nitro-benzylamino)-methyl]-pyrrolidine-1-carboxylic acid tert-butyl ester To a stirred solution of 3-aminomethyl-pyrrolidine-1-carboxylic acid tert-butyl ester (0.35 g, 1.97 mmol) and 4-methyl-3-nitro-benzaldehyde (0.327 g, 1.97 mmol) in ethanol (6 ml) was added titanium isopropoxide (0.35 ml) at 0° C. and stirred. The reaction was gradually brought to RT and stirred for 16 h. Then sodiumborohydride (0.078 g, 1.97 mmol) was added followed by catalytic amount of acetic acid and stirred for 3 h at ambient temperature. Upon completion, the solvents in the reaction were distilled out. The crude was diluted with 10% MeOH—CH$_2$Cl$_2$ solution and washed with water. The organic layer was then dried over sodium sulfate and concentrated under reduced pressure. The obtained crude was taken was purified by (100-200 mesh) silicagel column chromatography eluting the required compound with 3% MeOH—CH$_2$Cl$_2$ as a yellow solid (0.36 g).

(55b) (4-Methyl-3-nitro-benzyl)-pyrrolidin-3-ylmethyl-amine

To a stirred solution of compound 55a (0.32 g) in CH$_2$Cl$_2$ (2 ml) was added a solution of 4M HCl in dioxan (3 ml) at 0° C. The reaction was stirred at RT for 3 h. The solvent in the reaction was distilled out to afford the required compound as an hydrochloric salt (0.16 g).

(55c) VT-03-00086

To a stirred solution of Compound 6-methoxy-4-vinyl-quinoline-3-carbonitrile (0.13 g, 0.62 mmol) and Compound 55b (0.16 g, 0.62 mmol) in DMF (3 ml) was added tetramethyl guanidine (0.1 ml). The reaction was stirred at RT for 3 h. Upon completion, the DMF in the reaction mass was distilled out. The crude was diluted with 10% MeOH—CH$_2$Cl$_2$ and washed with water and concentrated under reduced pressure. The obtained crude was purified by preparative TLC to afford the required compound as a yellow solid (0.016 g).

(56) Synthesis of VT-03-00087

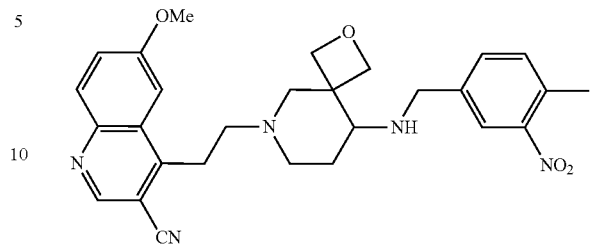

(56a) 9-(4-Methyl-3-nitro-benzylamino)-2-oxa-6-aza-spiro[3.5]nonane-6-carboxylic acid tert-butyl ester To a stirred solution of 9-amino-2-oxa-6-aza-spiro[3.5]nonane-6-carboxylic acid tert-butyl ester (0.35 g, 1.75 mmol) and 6-methyl-pyridine-3-carbaldehyde (0.327 g, 1.97 mmol) in ethanol (6 ml) was added titanium isopropoxide (0.35 ml) at 0° C. and stirred. The reaction was gradually brought to RT and stirred for 16 h. Then sodium borohydride (0.078 g, 1.97 mmol) was added followed by catalytic amount of acetic acid and stirred for 3 h at ambient temperature. Upon completion, the solvents in the reaction were distilled out. The crude is diluted with 10% MeOH—CH$_2$Cl$_2$ solution and washed with water. The organic layer was then dried over sodium sulfate and concentrated under reduced pressure. The obtained crude was purified by (100-200 mesh) silicagel column chromatography to afford the required compound.

(56b) (4-Methyl-3-nitro-benzyl)-(2-oxa-6-aza-spiro[3.5]non-9-yl)-amine

To a stirred solution of compound 56a (0.32 g) in CH$_2$Cl$_2$ (2 ml) was added a solution of 4M HCl in dioxan (3 ml) at 0° C. The reaction was stirred at RT for 3 h. The solvent in the reaction was distilled out to afford the required compound as an hydrochloric salt (0.16 g).

(56c) VT-03-00087

To a stirred solution of Compound 6-methoxy-4-vinyl-quinoline-3-carbonitrile (0.13 g, 0.62 mmol) and Compound 56b (0.16 g, 0.62 mmol) in DMF (3 ml) was added tetramethyl guanidine (0.1 ml). The reaction is stirred at RT for 3 h. Upon completion, the DMF in the reaction mass was distilled out. The crude was diluted with 10% MeOH—CH$_2$Cl$_2$ and washed with water and concentrated under reduced pressure. The obtained crude was purified by preparative TLC to afford the required compound.

(57) Synthesis of VT-03-00088

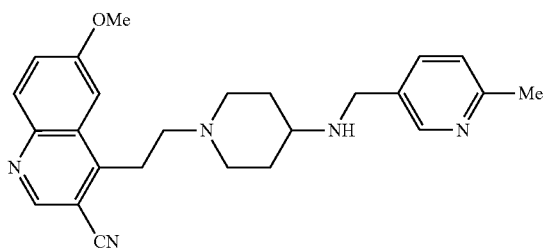 [SMILES: COc1ccc2ncc(C#N)c(CCN3CCC(NCc4ccc(C)nc4)CC3)c2c1]

(57a) 4-[(6-Methyl-pyridin-3-ylmethyl)-amino]-piperidine-1-carboxylic acid tert-butyl ester To a stirred solution of 4-amino-piperidine-1-carboxylic acid tert-butyl ester (0.35 g, 1.75 mmol) and 6-methyl-pyridine-3-carbaldehyde (0.327 g, 1.97 mmol) in ethanol (6 ml) was added titanium isopropoxide (0.35 ml) at 0° C. and stirred. The reaction was gradually brought to RT and stirred for 16 h. Then sodium borohydride (0.078 g, 1.97 mmol) was added followed by catalytic amount of acetic acid and stirred for 3 h at ambient temperature. Upon completion, the solvents in the reaction were distilled out. The crude was diluted with 10% MeOH—$CH_2Cl_2$ solution and washed with water. The organic layer was then dried over sodium sulfate and concentrated under reduced pressure. The obtained crude was purified by (100-200 mesh) silicagel column chromatography to afford the required compound.

(57b) (6-Methyl-pyridin-3-ylmethyl)-piperidin-4-yl-amine

To a stirred solution of compound 57a (0.32 g) in $CH_2Cl_2$ (2 ml) is added a solution of 4M HCl in dioxan (3 ml) at 0° C. The reaction was stirred at RT for 3 h. The solvent in the reaction is distilled out to afford the required compound as an hydrochloric salt.

(57c) VT-03-00088

To a stirred solution of Compound 6-methoxy-4-vinyl-quinoline-3-carbonitrile (0.13 g, 0.62 mmol) and Compound 57b (0.16 g, 0.62 mmol) in DMF (3 ml) was added tetramethyl guanidine (0.1 ml). The reaction was stirred at RT for 3 h. Upon completion, the DMF in the reaction mass was distilled out. The crude is diluted with 10% MeOH—$CH_2Cl_2$ and washed with water and concentrated under reduced pressure. The obtained crude is purified by preparative TLC to afford the required compound.

(58) Synthesis of VT-03-00089

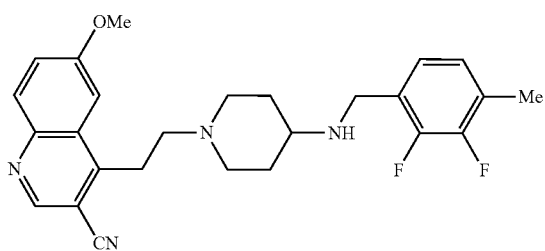 [SMILES: COc1ccc2ncc(C#N)c(CCN3CCC(NCc4ccc(C)c(F)c4F)CC3)c2c1]

(587a) 4-(2,3-Difluoro-4-methyl-benzylamino)-piperidine-1-carboxylic acid tert-butyl ester To a stirred solution of 4-amino-piperidine-1-carboxylic acid tert-butyl ester (0.35 g, 1.75 mmol) and 2,3-difluoro-4-methyl-benzaldehyde (0.327 g, 1.97 mmol) in ethanol (6 ml) was added titanium isopropoxide (0.35 ml) at 0° C. and stirred. The reaction was gradually brought to RT and stirred for 16 h. Then sodium borohydride (0.078 g, 1.97 mmol) was added followed by catalytic amount of acetic acid and stirred for 3 h at ambient temperature. Upon completion, the solvents in the reaction were distilled out. The crude is diluted with 10% MeOH—$CH_2Cl_2$ solution and washed with water. The organic layer was then dried over sodium sulfate and concentrated under reduced pressure. The obtained crude was purified by (100-200 mesh) silicagel column chromatography to afford the required compound.

(58b) (2,3-Difluoro-4-methyl-benzyl)-piperidin-4-yl-amine

To a stirred solution of compound 58a (0.32 g) in $CH_2Cl_2$ (2 ml) was added a solution of 4M HCl in dioxan (3 ml) at 0° C. The reaction is stirred at RT for 3 h. The solvent in the reaction was distilled out to afford the required compound as an hydrochloric salt.

(58c) VT-03-00089

To a stirred solution of compound 6-methoxy-4-vinyl-quinoline-3-carbonitrile (0.13 g, 0.62 mmol) and Compound 58b (0.16 g, 0.62 mmol) in DMF (3 ml) was added tetramethyl guanidine (0.1 ml). The reaction was stirred at RT for 3 h. Upon completion, the DMF in the reaction mass was distilled out. The crude is diluted with 10% MeOH—$CH_2Cl_2$ and washed with water and concentrated under reduced pressure. The obtained crude was purified by preparative TLC to afford the required compound.

(59) Synthesis of VT-03-00090

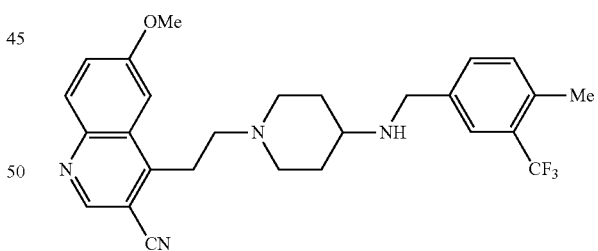

(59a) 4-(4-Methyl-3-trifluoromethyl-benzylamino-piperidine-1-carboxylic acid tert-butyl ester To a stirred solution of 4-amino-piperidine-1-carboxylic acid tert-butyl ester (0.35 g, 1.75 mmol) and 4-methyl-3-trifluoromethyl-benzaldehyde (0.327 g, 1.97 mmol) in ethanol (6 ml) was added titanium isopropoxide (0.35 ml) at 0° C. and stirred. The reaction was gradually brought to RT and stirred for 16 h. Then sodium borohydride (0.078 g, 1.97 mmol) was added followed by catalytic amount of acetic acid and stirred for 3 h at ambient temperature. Upon completion, the solvents in the reaction were distilled out.

The crude was diluted with 10% MeOH—CH$_2$Cl$_2$ solution and washed with water. The organic layer was then dried over sodium sulfate and concentrated under reduced pressure. The obtained crude was purified by (100-200 mesh) silicagel column chromatography to afford the required compound.

(59b) (4-Methyl-3-trifluoromethyl-benzyl)-piperidin-4-yl-amine

To a stirred solution of compound 59a (0.32 g) in CH$_2$Cl$_2$ (2 ml) was added a solution of 4M HCl in dioxan (3 ml) at 0° C. The reaction is stirred at RT for 3 h. The solvent in the reaction was distilled out to afford the required compound as an hydrochloric salt.

(59c) VT-03-00090

To a stirred solution of Compound 6-methoxy-4-vinyl-quinoline-3-carbonitrile (0.13 g, 0.62 mmol) and Compound 59b (0.16 g, 0.62 mmol) in DMF (3 ml) was added tetramethyl guanidine (0.1 ml). The reaction was stirred at RT for 3 h. Upon completion, the DMF in the reaction mass was distilled out. The crude was diluted with 10% MeOH—CH$_2$Cl$_2$ and washed with water and concentrated under reduced pressure. The obtained crude was purified by preparative TLC to afford the required compound.

(60) Synthesis of VT-03-00091

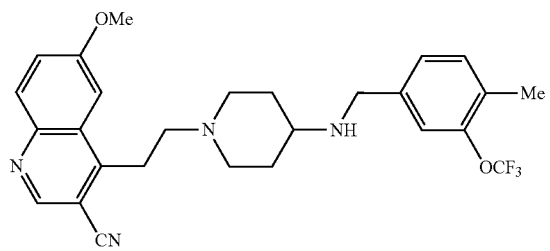 [SMILES: COc1ccc2ncc(C#N)c(CCN3CCC(NCc4ccc(C)c(OC(F)(F)F)c4)CC3)c2c1]

(60a) 4-(4-Methyl-3-trifluoromethoxy-benzylamino)-piperidine-1-carboxylic acid tert-butyl ester To a stirred solution of 4-amino-piperidine-1-carboxylic acid tert-butyl ester (0.35 g, 1.75 mmol) and 4-methyl-3-trifluoromethoxy-benzaldehyde (0.327 g, 1.97 mmol) in ethanol (6 ml) was added titanium isopropoxide (0.35 ml) at 0° C. and stirred. The reaction was gradually brought to RT and stirred for 16 h. Then sodium borohydride (0.078 g, 1.97 mmol) was added followed by catalytic amount of acetic acid and stirred for 3 h at ambient temperature. Upon completion, the solvents in the reaction were distilled out. The crude was diluted with 10% MeOH—CH$_2$Cl$_2$ solution and washed with water. The organic layer was then dried over sodium sulfate and concentrated under reduced pressure. The obtained crude was taken was purified by (100-200 mesh) silicagel column chromatography to afford the required compound.

(60b) (4-Methyl-3-trifluoromethoxy-benzyl)-piperidin-4-yl-amine

To a stirred solution of compound 60a (0.32 g) in CH$_2$Cl$_2$ (2 ml) is added a solution of 4M HCl in dioxan (3 ml) at 0° C. The reaction was stirred at RT for 3 h. The solvent in the reaction was distilled out to afford the required compound as a hydrochloric salt.

(60c) VT-03-00091

To a stirred solution of compound 6-methoxy-4-vinyl-quinoline-3-carbonitrile (0.13 g, 0.62 mmol) and compound 60b (0.16 g, 0.62 mmol) in DMF (3 ml) was added tetramethyl guanidine (0.1 ml). The reaction was stirred at RT for 3 h. Upon completion, the DMF in the reaction mass was distilled out. The crude was diluted with 10% MeOH—CH$_2$Cl$_2$ and washed with water and concentrated under reduced pressure. The obtained crude was purified by preparative TLC to afford the required compound.

(61) Synthesis of VT-03-00092

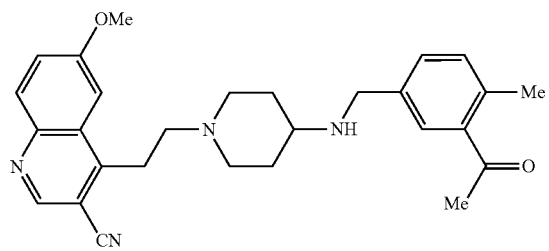 [SMILES: COc1ccc2ncc(C#N)c(CCN3CCC(NCc4ccc(C)c(C(C)=O)c4)CC3)c2c1]

(61a) 4-(3-Acetyl-4-methyl-benzylamino)-piperidine-1-carboxylic acid tert-butyl ester To a stirred solution of 4-amino-piperidine-1-carboxylic acid tert-butyl ester (0.35 g, 1.75 mmol) and 3-acetyl-4-methyl-benzaldehyde (0.327 g, 1.97 mmol) in ethanol (6 ml) was added titanium isopropoxide (0.35 ml) at 0° C. and stirred. The reaction was gradually brought to RT and stirred for 16 h. Then sodium borohydride (0.078 g, 1.97 mmol) was added followed by catalytic amount of acetic acid and stirred for 3 h at ambient temperature. Upon completion, the solvents in the reaction were distilled out. The crude was diluted with 10% MeOH—CH$_2$Cl$_2$ solution and washed with water. The organic layer was then dried over sodium sulfate and concentrated under reduced pressure. The obtained crude was purified by (100-200 mesh) silicagel column chromatography to afford the required compound.

(61b) 1-[2-Methyl-5-(piperidin-4-ylaminomethyl)-phenyl]-ethanone

To a stirred solution of compound 61a (0.32 g) in CH$_2$Cl$_2$ (2 ml) was added a solution of 4M HCl in dioxan (3 ml) at 0° C. The reaction was stirred at RT for 3 h. The solvent in the reaction was distilled out to afford the required compound as an hydrochloric salt.

(61c) VT-03-00092

To a stirred solution of Compound 6-methoxy-4-vinyl-quinoline-3-carbonitrile (0.13 g, 0.62 mmol) and Compound 61b (0.16 g, 0.62 mmol) in DMF (3 ml) was added tetramethyl guanidine (0.1 ml). The reaction is stirred at RT for 3 h. Upon completion, the DMF in the reaction mass was distilled out. The crude was diluted with 10% MeOH—CH$_2$Cl$_2$ and washed with water and concentrated under

(62) Synthesis of VT-03-00093

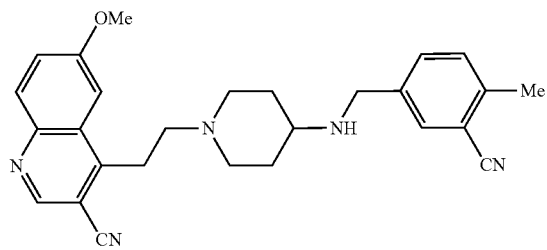 [SMILES: COc1ccc2ncc(C#N)c(CCN3CCC(NCc4ccc(C)c(C#N)c4)CC3)c2c1]

(62a) 4-(3-Cyano-4-methyl-benzylamino)-piperidine-1-carboxylic acid tert-butyl ester To a stirred solution of 4-amino-piperidine-1-carboxylic acid tert-butyl ester (0.35 g, 1.75 mmol) and 5-formyl-2-methyl-benzonitrile (0.327 g, 1.97 mmol) in ethanol (6 ml) was added titanium isopropoxide (0.35 ml) at 0° C. and stirred. The reaction is gradually brought to RT and stirred for 16 h. Then sodium borohydride (0.078 g, 1.97 mmol) was added followed by catalytic amount of acetic acid and stirred for 3 h at ambient temperature. Upon completion, the solvents in the reaction were distilled out. The crude was diluted with 10% MeOH—$CH_2Cl_2$ solution and washed with water. The organic layer was then dried over Sodium sulfate and concentrated under reduced pressure. The obtained crude was purified by (100-200 mesh) silicagel column chromatography to afford the required compound.

(62b) 2-Methyl-5-(piperidin-4-ylaminomethyl)-benzonitrile

To a stirred solution of compound 62a (0.32 g) in $CH_2Cl_2$ (2 ml) was added a solution of 4M HCl in dioxan (3 ml) at 0° C. The reaction is stirred at RT for 3 h. The solvent in the reaction was distilled out to afford the required compound as an hydrochloric salt.

(62c) VT-03-00093

To a stirred solution of Compound 6-methoxy-4-vinyl-quinoline-3-carbonitrile (0.13 g, 0.62 mmol) and Compound 62b (0.16 g, 0.62 mmol) in DMF (3 ml) was added tetramethyl guanidine (0.1 ml). The reaction is stirred at RT for 3 h. Upon completion, the DMF in the reaction mass is distilled out. The crude was diluted with 10% MeOH—$CH_2Cl_2$ and washed with water and concentrated under reduced pressure. The obtained crude was purified by preparative TLC to afford the required compound.

(63) Synthesis of VT-03-00094

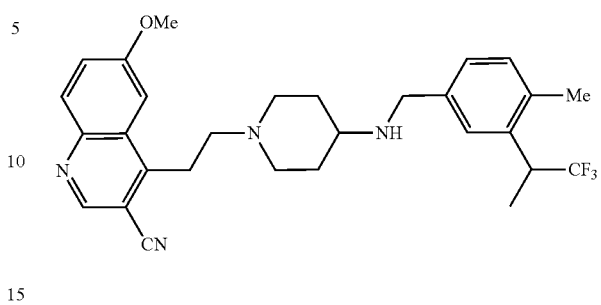

(63a) 4-[4-Methyl-3-(2,2,2-trifluoro-1-methyl-ethyl)-benzylamino]-piperidine-1-carboxylic acid tert-butyl ester To a stirred solution of 4-amino-piperidine-1-carboxylic acid tert-butyl ester (0.35 g, 1.75 mmol) and 4-methyl-3-(2,2,2-trifluoro-1-methyl-ethyl)-benzaldehyde (0.327 g, 1.97 mmol) in ethanol (6 ml) was added titanium isopropoxide (0.35 ml) at 0° C. and stirred. The reaction is gradually brought to RT and stirred for 16 h. Then sodium borohydride (0.078 g, 1.97 mmol) was added followed by catalytic amount of acetic acid and stirred for 3 h at ambient temperature. Upon completion, the solvents in the reaction were distilled out. The crude was diluted with 10% MeOH—$CH_2Cl_2$ solution and washed with water. The organic layer was then dried over sodium sulfate and concentrated under reduced pressure. The obtained crude is taken was purified by (100-200 mesh) silicagel column chromatography to afford the required compound.

(63b) [4-Methyl-3-(2,2,2-trifluoro-1-methyl-ethyl)-benzyl]-piperidin-4-yl-amine To a stirred solution of compound 63a (0.32 g) in $CH_2Cl_2$ (2 ml) was added a solution of 4M HCl in dioxan (3 ml) at 0° C. The reaction is stirred at RT for 3 h. The solvent in the reaction was distilled out to afford the required compound as an hydrochloric salt.

(63c) VT-03-00094

To a stirred solution of compound 6-methoxy-4-vinyl-quinoline-3-carbonitrile (0.13 g, 0.62 mmol) and compound 63b (0.16 g, 0.62 mmol) in DMF (3 ml) was added tetramethyl guanidine (0.1 ml). The reaction is stirred at RT for 3 h. Upon completion, the DMF in the reaction mass was distilled out. The crude is diluted with 10% MeOH—$CH_2Cl_2$ and washed with water and concentrated under reduced pressure. The obtained crude was purified by preparative TLC to afford the required compound.

(64) Synthesis of VT-03-00095

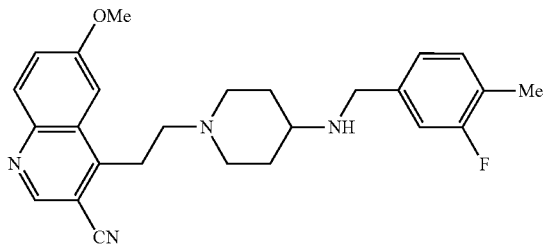

(64a) 4-(3-Fluoro-4-methyl-benzylamino)-piperidine-1-carboxylic acid tert-butyl ester To a stirred solution of 4-amino-piperidine-1-carboxylic acid tert-butyl ester (0.35 g, 1.75 mmol) and 4-methyl-3-(2,2,2-trifluoro-1-methyl-ethyl)-benzaldehyde (0.327 g, 1.97 mmol) in ethanol (6 ml) was added titanium isopropoxide (0.35 ml) at 0° C. and stirred. The reaction was gradually brought to RT and stirred for 16 h. Then sodium borohydride (0.078 g, 1.97 mmol) was added followed by catalytic amount of acetic acid and stirred for 3 h at ambient temperature. Upon completion, the solvents in the reaction were distilled out. The crude was diluted with 10% MeOH—$CH_2Cl_2$ solution and washed with water. The organic layer was then dried over sodium sulfate and concentrated under reduced pressure. The obtained crude is taken was purified by (100-200 mesh) silicagel column chromatography to afford the required compound.

(63b) (3-Fluoro-4-methyl-benzyl)-piperidin-4-yl-amine

To a stirred solution of compound 64a (0.32 g) in $CH_2Cl_2$ (2 ml) was added a solution of 4M HCl in dioxan (3 ml) at 0° C. The reaction was stirred at RT for 3 h. The solvent in the reaction was distilled out to afford the required compound as an hydrochloric salt.

(64c) VT-03-00095

To a stirred solution of Compound 6-methoxy-4-vinyl-quinoline-3-carbonitrile (0.13 g, 0.62 mmol) and Compound 64b (0.16 g, 0.62 mmol) in DMF (3 ml) was added tetramethyl guanidine (0.1 ml). The reaction was stirred at RT for 3 h. Upon completion, the DMF in the reaction mass was distilled out. The crude is diluted with 10% MeOH—$CH_2Cl_2$ and washed with water and concentrated under reduced pressure. The obtained crude was purified by preparative TLC to afford the required compound.

[4] USES

The compounds of the invention are useful for the treatment of infections in subjects, mammals in particular, including humans. In one embodiment, the compounds may be used for the treatment of infections of soft tissues, blood, skin, mouth, lungs, respiratory tract, urinary tract and reproductive tract.

In another embodiment, the compounds of the invention are useful for the treatment of infections caused by microorganisms, such as but not limited to *Staphylococcus* species such as *Staphylococcus aureus*, *Staphylococcus epidermidis*, *Staphylococcus haemolyticus*, *Enterococcus* species such as *Enterococcus faecalis*, *Enterococcus faecium*, *Streptococcus* species like *Streptococcus pneumoniae*, *Streptococcus pyogenes*, *Streptococcus agalactiae*, *Moraxella* species, for example *Moraxella catarrhalis*, *E. coli*, *Klebsiella* species such as *Klebsiella pneumoniae*, *Klebsiella oxytoca*, *Pseudomonas* species such as *Pseudomonas aeruginosa*, *Acinetobacter* species such as *Acinetobacter baumannii*.

[5] ROUTE OF ADMINISTRATION

The compounds of the present invention are delivered to the subjects by forms suitable for each administration route. For example, the compounds are administered as tablets, capsules, injection, drops, inhaler, ointment, foams suppository. In a preferred embodiment, the route of administration is oral, parenteral or topical. Topical or transdermal administration include powders, sprays, ointments, pastes creams, lotions, gels, solutions, patches and inhalants.

[6] DOSAGE FORMS

The composition of the present invention is presented in unit dosage form generally in an amount that produces a therapeutic effect in the subject.

The compounds of the present invention are administered at a daily dose that is the lowest dose effective to produce a therapeutic effect. Generally, the dosage will effect from about 0.0001 to about 100 mg per kg body weight per day. Preferably, the dosage will range from about 0.001 to 75 mg per kg body weight per day and more preferably, the dosage will range from about 0.1 to about 50 mg per kg body weight per day. Each unit dose may be, for example, 5, 10, 25, 50, 100, 125, 150, 200 or 250 mg of the compound of the invention. As per the requirement of the subject, the effective daily dose of the compound is administered as two, three, four or more sub-doses administered separately at appropriate intervals throughout the day, optionally in unit dosage forms.

[7] FORMULATION

The antibacterial compositions of the present invention may be administered by any method known in the art. Some examples of suitable modes of administration include oral, intravenous, intramuscular topical or any other parenteral mode of administration.

In certain embodiments, the present invention is directed to a method of formulating compounds of the present invention in a pharmaceutically acceptable carrier or excipient and may be administered in a wide variety of different dosage forms e.g. tablets, capsules, sprays, creams, lotions, ointments, aqueous suspensions syrups, and the like. Such carriers may include one or more of solid diluents or fillers, sterile aqueous media, and various nontoxic organic solvents, etc.

For oral administration, tablets may contain various excipients such as one or more of microcrystalline cellulose, sodium citrate, calcium carbonate and the like, along with various disintegrants such as starch and certain complex silicates, together with granulation binders like polyvinylpyrrolidone, sucrose and the like. Solid compositions of a similar type may also be employed as fillers in gelatin capsules.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluents or solvent e.g. as solution in 1, 3 butane diol. Among the acceptable vehicles and solvents that may be employed are water, Ringer's solution and isotonic sodium chloride solution. In addition, sterile fixed oils are conventionally employed including synthetic mono or diglycerides. In addition, fatty acids such as oleic acid find in the preparation of injectables. These aqueous solutions may be suitable for intravenous injection purposes. The oily solutions may be suitable for intra articular, intramuscular, and/or subcutaneous injection purposes.

In another embodiment, the compounds of the present invention may be administered topically that include transdermal, buccal, or sublingual application. For topical applications, therapeutic compounds may be suitably admixed in a pharmacologically inert topical carrier such as a gel, an ointment, a lotion, and/or a cream. Such topical carriers may include water, glycerol, alcohol, propylene glycol, fatty alcohols, triglycerides, fatty acid esters, and/or mineral oils.

The timing of the administration of the pharmaceutical composition may also be regulated. For example the compounds may be administered intermittently or by controlled release.

[8] DEFINITIONS

As used herein, an "independently" selected substituent refers to a group of substituents, wherein the substituents may be different.

The term "optionally substituted" indicates that the said substituent can be unsubstituted or substituted.

The term "absent" is used to designate the lacking of a group or describe the structural value of a variable. For example in some embodiments, $A_2$ and $A_3$ may be null or does not exist. In some other embodiments variable "$A_2$" for a formula (I) compound, indicates that in the absence of the said variable, the adjacent variables on both sides of the absent variable are connected directly together and is synonymous to a single covalent bond. For example, in the chain -G-$A_2$-NH-$A_3$-$R_6$, if $A_2$ is "absent", then the chain becomes -G-NH-$A_3$-$R_6$.

The term "alkyl" refers to the radical of saturated aliphatic groups, including straight-chain alkyl groups, branched-chain alkyl groups, cycloalkyl (alicyclic) groups, alkyl substituted cycloalkyl groups and cycloalkyl substituted alkyl groups; wherein the term "cycloalkyl" refers to a saturated or unsaturated monocyclic alkyl ring consisting of 3-8 carbon atoms or a saturated or partially unsaturated bicyclic ring consisting of 9 or 10 carbon atoms.

The term "aryl" refers to a mono- or bicyclic aromatic ring containing optionally substituted carbon atoms. The said term "aryl" can be fused to saturated or unsaturated cyclic ring containing minimum one heteroatom selected from oxygen, nitrogen and sulphur which is optionally substituted. The preferred substituents are alkyl, alkoxy, alkyl optionally substituted with alkoxy, alkoxy optionally substituted with alkyl, carboxy, hydroxyalkyl, hydroxyl, halogen, haloalkyl, alkylthio, alkylsulfonyl, cyano, nitro, alkynyl, amino, aminoalkyl, alkylcarbonyl, aminosulfonyl, oxo, carbomyl, carbonyl, haloalkoxy.

The term "heteroaryl" refers to an optionally substituted 5- or 6-membered monocyclic hetero aromatic ring or a 9- or 10-membered bicyclic hetero aromatic ring containing minimum one heteroatom which are independently selected from nitrogen, sulphur or oxygen. The said term "heteroaryl" can be fused to saturated or unsaturated cyclic ring containing minimum one of the said heteroatom which is optionally substituted. The preferred substituents are alkyl, alkoxy, alkyl optionally substituted with alkoxy, alkoxy optionally substituted with alkyl, carboxy, hydroxyalkyl, hydroxyl, halogen, haloalkyl, alkylthio, alkylsulfonyl, cyano, nitro, alkynyl, amino, aminoalkyl, alkylcarbonyl, aminosulfonyl, oxo, carbomyl, carbonyl, haloalkoxy.

The term "alkoxy" refers to alkyl ether radical, wherein the term "alkyl" is as defined above.

The term "amino" refers to —$NH_2$ group.

The term "aminoalkyl" refers to —NH (alkyl) or —N(alkyl)(alkyl) group wherein the term "alkyl" is as defined above.

The term "aminosulfonyl" refers to —$S(=O)_2$—$NR'_2$ radical, wherein each R' independently represent "alkyl" as defined above or hydrogen.

The term "halogen" refers to F, Cl, Br or I.

The term "haloalkyl" refers to an "alkyl" group substituted with one or more halogen wherein the terms "alkyl" and "halogen" are as defined above.

The term "haloalkoxy" refers to an "alkoxy" group substituted with at least one "halogen" wherein the terms "alkoxy" and "halogen" are as defined above.

The term "hydroxyl" refers to —OH group.

The term "hydroxyalkyl" refers to an alkyl group which is substituted with one or more, preferably one "hydroxyl" group and, wherein the terms "hydroxyl" and "alkyl" are as defined above.

The term "carbomyl" refers to —$C(O)NH_2$ group.

The term "carbonyl" refers to —C=O group.

The term "oxo" refers to double bonded oxygen atom (=O).

The term "nitro" refers to —$NO_2$ group.

The term "cyano" refers to —CN group.

The term "carboxy" refers to —C(=O)OH group.

The term "thiol" or "thio" refers to —SH group.

The term "sulfonyl" refers to —$S(=O)_2$ group.

The term "alkylsulfonyl" refers to —$S(=O)_2$-alkyl group wherein the term "alkyl" is as defined above.

The term "arylsulfonyl" refers to —$S(=O)_2$-aryl group wherein the term "aryl" is as defined above.

The term "alkyl sulfonyloxy" refers to —$OSO_2$-alkyl group wherein the term "alkyl" is as defined above.

The term "aryloxy" refers to aryl ether radical, wherein the term "aryl" is as defined above.

The term "acyloxy" refers to alkyl-C(=O)—O-alkyl where alkyl-C(=O) is the "acyl" group and the term "alkyl" is as defined above.

The term "alkylcarbonyl" refers to —C(=O)(alkyl)- group wherein the term "alkyl" is as defined above.

The term "alkenylcarbonyl" refers to —C(=O)(alkenyl)- group wherein the term "alkenyl" is as defined above.

The term "alkoxycarbonyl" refers to —C(=O)(alkoxy)- group wherein the term "alkoxy" is as defined above.

The term "thioalkyl" or "alkylthio" refers to —S-alkyl radical wherein the term "alkyl" is as defined above.

The term "arylthio" refers to —S-aryl radical wherein the term "aryl" is as defined above.

The term "acylthio" refers to —S-acyl radical wherein the term "acyl" is as defined above.

The term "heterocyclylthio" refers to —S-heterocyclyl radical wherein the term "heterocyclyl" is as defined herein.

The term "heterocyclyloxy" refers to —O-heterocyclyl radical wherein the term "heterocyclyl" is as defined herein.

Unless otherwise defined, the term "heterocyclic" or "heterocyclyl" as used above includes optionally substituted aromatic and non-aromatic, single and fused, mono- or bicyclic rings suitably containing minimum one heteroatom selected from oxygen, nitrogen and sulphur, which rings may be optionally C-substituted. The preferred substituents are alkyl, alkoxy, alkyl optionally substituted with alkoxy, alkoxy optionally substituted with alkyl, carboxy, hydroxyalkyl, hydroxyl, halogen, haloalkyl, alkylthio, alkylsulfonyl, cyano, nitro, alkynyl, amino, aminoalkyl, alkylcarbonyl, aminosulfonyl, oxo, carbomyl, carbonyl, haloalkoxy.

The term "containing at least one heteroatom" refers to at least one carbon atom of the ring being replaced by a heteroatom selected from oxygen, nitrogen and sulphur.

The compounds of present invention may exist in specific geometric or stereoisomeric forms.

The present invention is inclusive of all possible enantiomers and diastereomers in pure or substantially pure form and mixtures of two or more stereoisomers in ratios that are effective. This means that the compounds of present invention may exist both as levorotatory and as dextrorotatory, in the form of racemates and in the form of two enantiomers.

The compounds of present invention are capable of forming both pharmaceutically acceptable salts.

Examples of salts include but not restricted to metals or amines such as alkali and alkaline earth metals or organic amines. Examples of suitable acids for salt formation include but is not limited to hydrochloric, sulphuric, phosphoric, acetic, citric, oxalic, malonic, salicyclic, malic, fumaric, succinic, ascorbic and the likes thereof.

The compound of the present invention can exist as unsolvated or solvated forms including hydrated forms.

The compounds detailed in the present disclosure are capable of forming pharmaceutically acceptable prodrugs. Prodrugs are covalently bonded carriers that release the active compound internally after administration to the subject.

The present invention provides pharmaceutical compositions comprising an effective amount of compound of Formula (I), prodrugs, tautomeric forms, stereoisomers, optical isomers, pharmaceutically acceptable salts, solvates, polymorphs, analogs or derivatives thereof with pharmaceutically acceptable carriers.

The invention has been described with reference to various specific and preferred embodiments and techniques. However, it should be noted that many variations and modifications may be made while remaining within the scope of the invention.

Example 1

Analysis of Microbiological Activity of Compounds

Shown below are the microbiological activities of representative compounds of the invention. The compounds were tested by the microbroth dilution method (National committee for Clinical Laboratory Standards, 2011, M07-08) and the Minimum Inhibitory Concentration (MIC) was determined.

| | MIC (ug/ml) | | | | | | |
|---|---|---|---|---|---|---|---|
| Compound | Staphylococcus aureus (ATCC 29213) | Methicillin resistant Staphylococcus aureus (ATCC 33591) | Streptococcus pneumoniae (ATCC 6301) | Enterococcus faecalis (ATCC 29212) | Moraxella catarrhalis (ATCC 8176) | E. coli (ATCC 25922) | K. pneumoniae (ATCC 700603) |
| VT-03-00014 | 2 | 4 | 2 | 4 | 4 | 32 | >128 |
| VT-03-00017 | >32 | >32 | >16 | >64 | >16 | >32 | ND |
| VT-03-00021 | 0.25 | 0.12 | 1 | 2 | 2 | 16 | >32 |
| VT-03-00021a | ≤0.03 | 0.06 | 0.12 | 2 | 2 | 16 | ND |
| VT-03-00022 | 1 | 2 | 2 | 4 | 4 | >64 | ND |
| VT-03-00024 | 1 | 2 | 2 | 8 | 8 | >32 | ND |
| VT-03-00026 | 2 | 4 | 1 | 8 | 2 | 32 | 64 |
| VT-03-00026a | 1 | 2 | 2 | 8 | 4 | 16 | ND |
| VT-03-00027 | 2 | 4 | 2 | 4 | 8 | >32 | ND |
| VT-03-00028 | 0.25 | 0.5 | 0.25 | 1 | 4 | >32 | >32 |
| VT-03-00030 | 2 | 4 | 4 | 4 | 1 | 8 | >32 |
| VT-03-00031 | 1 | 2 | 1 | 2 | 4 | 16 | >32 |
| VT-03-00032 | 2 | 4 | 4 | 8 | 8 | >32 | >32 |
| VT-03-00042 | >16 | >16 | ND | ND | ND | >32 | ND |
| VT-03-00043 | 16 | >16 | ND | ND | ND | >32 | ND |
| VT-03-00045 | 0.06 | 0.12 | 0.5 | 4 | 2 | 32 | ND |
| VT-03-00046 | 16 | >16 | ND | ND | ND | >32 | ND |
| VT-03-00048 | 0.12 | 0.5 | 0.5 | 4 | 1 | 8 | >32 |

|  | MIC (ug/ml) | | | | | | |
| --- | --- | --- | --- | --- | --- | --- | --- |
| Compound | Staphylococcus aureus (ATCC 29213) | Methicillin resistant Staphylococcus aureus (ATCC 33591) | Streptococcus pneumoniae (ATCC 6301) | Enterococcus faecalis (ATCC 29212) | Moraxella catarrhalis (ATCC 8176) | E. coli (ATCC 25922) | K. pneumoniae (ATCC 700603) |
| VT-03-00049 | 0.12 | 0.5 | 0.5 | 2 | 8 | 32 | >32 |
| VT-03-00050 | 0.25 | 0.5 | 4 | 4 | 4 | 16 | >16 |
| VT-03-00051 | 2 | 4 | >4 | 4 | 2 | >32 | >16 |
| VT-03-00052 | 0.125 | 0.25 | 1 | 4 |  | 16 |  |
| VT-03-00053 | 0.25 | 0.25 | 1 | 2 | 0.5 | 4 | >32 |
| VT-03-00054 | 0.03 | 0.12 | 0.5 | 2 | 1 | 8 | 32 |
| VT-03-00055 | 1 | 4 | 0.03 | 0.25 | >32 | >32 | >32 |
| VT-03-00056 | 0.25 | 0.5 | 0.25 | 8 | 1 | 4 | >32 |
| VT-03-00057 | 0.12 | 0.25 | 0.5 | 2 | 0.5 | 2 | >32 |
| VT-03-00058 | 0.015 | 0.06 | 0.03 | 0.25 | 0.5 | 1 | 16 |
| VT-03-00059 | 0.25 | 1 | 2 | 8 | 8 | >32 | >32 |
| VT-03-00060 | >4 | >4 | ND | ND | >32 | >32 | ND |
| VT-03-00061 | 0.015 | 0.015 | 0.015 | 0.25 | 0.12 | 1 | 8 |
| VT-03-00062 | ≤0.0075 | 0.015 | 0.015 | 0.12 | ≤0.06 | 0.5 | 8 |
| VT-03-00062a | 0.5 | 1 | 0.5 | 4 | 2 | 4 | >32 |
| VT-03-00063 | 0.25 | 0.5 | 0.25 | 2 | 0.25 | 4 | >32 |
| VT-03-00064 | 0.12 | 0.25 | 0.12 | 2 | 0.25 | 4 | >32 |
| VT-03-00065 | 0.25 | 1 | 4 | >32 | >32 | >32 | >32 |
| VT-03-00066 | 0.5 | 1 | 1 | 4 | 4 | 16 | >32 |
| VT-03-00067 | 0.12 | 0.5 | 0.25 | ND | 2 | 16 | 32 |
| VT-03-00069 | >4 | >4 | ND | ND | ND | >4 | ND |
| VT-03-00070 | >4 | >4 | ND | ND | ND | >4 | ND |
| VT-03-00071 | ND | ND | ND | ND | ND | ND | ND |
| VT-03-00072 | >4 | >4 | ND | ND | ND | >4 | ND |
| VT-03-00074 | 1 | 2 | 2 | 8 | 2 | 32 | ND |
| VT-03-00075 | 0.12 | 0.12 | 0.06 | 0.5 | 0.5 | 4 | >16 |
| VT-03-00076 | 0.015 | 0.03 | 0.03 | 0.25 | 0.25 | 2 | >16 |
| VT-03-00077 | 0.06 | 0.12 | 0.12 | 1 | 0.25 | 2 | >16 |
| VT-03-00078 | >4 | ND | ND | ND | ND | >32 | ND |
| VT-03-00079 | 2 | 2 | 2 | 32 | 4 | 32 | ND |
| VT-03-00080 | 0.25 | 1 | 2 | 4 | >4 | 32 | ND |
| VT-03-00081 | ND | 1 | ND | ND | ND | >32 | ND |
| VT-03-00083 | 0.06 | 0.12 | ND | ND | ND | 4 | ND |
| VT-03-00084 | 0.5 | 0.5 | 0.25 | 2 | 2 | 8 | ND |

ND = not done

Example 2

MICs Against Fluoroquinolone Resistant Strains

To test if compounds are able to overcome fluoroquinolone resistance, we have determined the MICS against Fluoroquinolone (FQ) resistant clinical strains of MRSA and E. coli.

| Compound name | MIC in μg/ml against FQ resistant strains | |
|---|---|---|
| | MRSA E9823 | MRSA E9749 |
| VT-03-00052 | 0.25 | 0.25 |
| VT-03-00057 | 0.25 | 0.25 |
| VT-03-00061 | ≤0.0075 | 0.015 |
| VT-03-00062 | ≤0.0075 | 0.015 |

| | E. coli E1851 | E. coli U1306 | E. coli U5690 | E. coli 86 |
|---|---|---|---|---|
| VT-03-00057 | 2 | 16 | 8 | 16 |
| VT-03-00061 | 0.5 | 2 | 2 | 2 |
| Ciprofloxacin | >4 | >4 | >4 | >4 |

Example 3

Analysis of Target Specificity of Compounds

To test for target specificity, the activity of compounds was evaluated in an in vitro Gyrase assay using recombinant Gyrase protein as per the instructions of the assay kit (Inspiralis). The assay measures the ability of E. coli Gyrase to convert relaxed plasmid DNA into the supercoiled form. The enzyme is incubated with the substrate (relaxed DNA) in the presence and absence of compounds for 1 hour at 37° C. and the DNA is run on a gel at low voltage for several hours. The gel is then stained with Ethidium bromide and DNA in the different forms is quantified using DNA imaging and quantification software (Image Lab). The activity of the enzyme is proportional to the amount of supercoiled form detected.

| | % inhibition of DNA supercoiling activity | |
|---|---|---|
| Compound | 1 μM | 0.1 μM |
| VT-03-00045 | 96.5 | 96.5 |
| VT-03-00048 | 97.3 | 97.5 |
| VT-03-00055 | 71 | 52.7 |
| VT-03-00057 | 90.6 | 61.4 |
| VT-03-00061 | 99.7 | 99.8 |
| VT-03-00062 | 98.7 | 91.5 |
| VT-03-00064 | 98.1 | 89.3 |
| VT-03-00066 | 89.9 | 55.9 |
| VT-03-00077 | 88.5 | 38.8 |
| VT-03-00079 | 87.6 | 16.7 |

Example 4

Mutation Prevention Concentration Studies

The mutation prevention concentration or the concentration above which mutants are unlikely to be selected, was determined based on published protocols (Antimicrobial Agents and Chemotherapy, 45, 433-438, 2001).

TABLE 2

Mutation prevention concentration for VT-03-00061 against MRSA 33591

| Compounds | Mutation prevention concentration (μg/ml) |
|---|---|
| VT-03-00061 | 0.12 |

Example 5

Time Kill Kinetics

Figure 2:
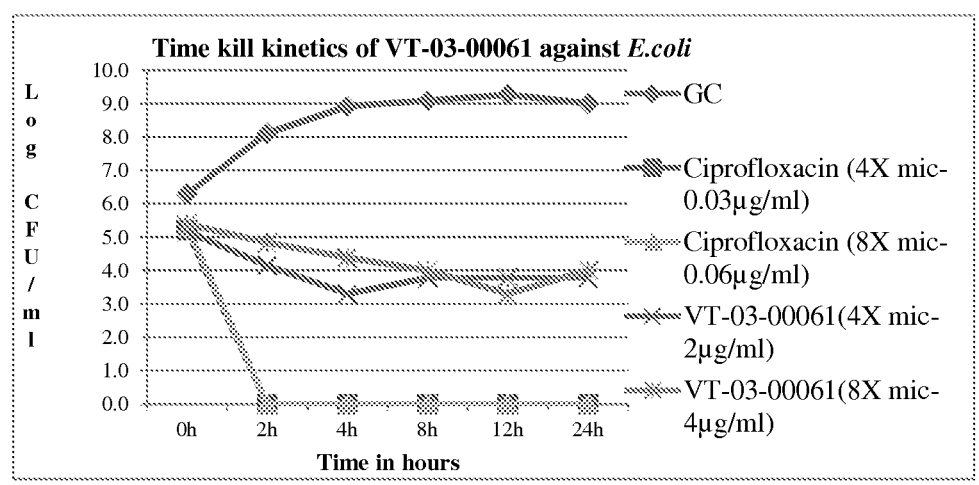
FIG. 2 discloses time kill kinetics of VT-03-00061 against *E. coli* 25922.

To understand the kinetics of growth in the presence of the VT-03 compounds, we undertook time kill assays (National committee for Clinical Laboratory Standards, M07-A8, Volume 29, 2009). Data for VT-03-00061 against MRSA 33591 (FIG. 1: time kill kinetics of VT-03-00061 against MRSA) and E. coli 25922 (FIG. 2: time kill kinetics of VT-03-00061 against E. coli); GC=Growth control.

Example 6 hERG Binding Studies

Inhibition of the inward rectifying voltage gated potassium channel encoded by the human ether-a-go-go related gene (hERG) current causes QT interval prolongation which may lead to cardiac arrhythmia (Current Topics in Ion Channels, 2008, 2, 87-93). To test the ability of the VT-03 compounds to bind the hERG channel, membranes expressing the hERG channel were incubated with radiolabeled Astemizole and displacement of the labeled ligand in the presence of compounds was measured. These data were used to derive the concentration at which 50% of the radioligand is displaced ($IC_{50}$). The compounds show no significant hERG binding activity up to the highest concentration tested indicating the advantage of VT-03 compounds over the known prior art antibacterial compounds (ref. BMCL, 21, 7489-7495, 2011).

| Compound Name | $IC_{50}$ value | Highest test concentration (μM) |
|---|---|---|
| VT-03-00063 | >30.00 μM | 30 |
| VT-03-00058 | >30.00 μM | 30 |
| VT-03-00061 | >30.00 μM | 30 |
| VT-03-00053 | >30.00 μM | 30 |

Example 7

Pharmacokinetic Profiles

Compounds were dosed to male Swiss albino mice to determine the pharmacokinetic profiles. Data for VT-03-00061 are shown below. The compound is orally bioavailable.

TABLE 5

Pharmacokinetic profiles of select compounds
Single Dose Pharmacokinetics Study of
VT-03-00061 in Male Swiss Albino Mice

| PK Parameters | Oral PK Study (10 mg/kg b.w.) | Intravenous PK Study (5 mg/kg b.w.) |
|---|---|---|
| $C_{max}$ (ng/mL) | 51.47 | 400.18 |
| $AUC_{inf}$ (h*ng/mL) | 103.82 | 368.41 |

TABLE 5-continued

Pharmacokinetic profiles of select compounds
Single Dose Pharmacokinetics Study of
VT-03-00061 in Male Swiss Albino Mice

| PK Parameters | Oral PK Study (10 mg/kg b.w.) | Intravenous PK Study (5 mg/kg b.w.) |
|---|---|---|
| $T_{1/2}$ (h) | 1.74 | 1.64 |
| F % (Oral bioavailability) | 11.51 | |

Example 8

In Vivo Activity in the Systemic Infection Model Against *S. Aureus* (MRSA ATCC 33591)

In order to evaluate the in vivo efficacy of the scaffold, we tested representative compounds for activity in the systemic infection model in mice (Antimicrobial Agents and Chemotherapy, 47, 2507-2512, 2003). In this model, a 15× medial lethal dose of the bacteria (MRSA ATCC33591) is administered to mice intraperitoneally. An hour later, the compound is administered i.v. and again 4 hours later. VT-03-00061, was efficacious with a 50% survival at a dose of 10 mg/kg in this model.

We claim:
1. A compound selected from the group consisting of:

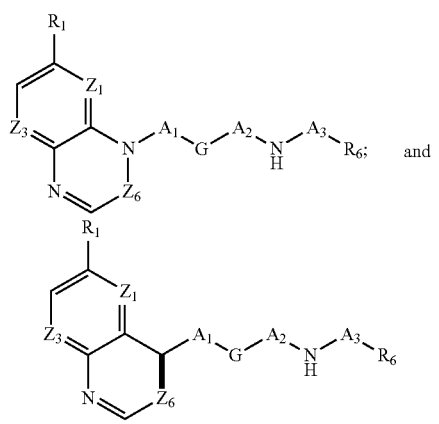

or a pharmaceutically acceptable salt thereof, wherein,
$Z_1$ and $Z_3$ are each independently selected from a group consisting of CH or N;
$Z_6$ is independently selected from group consisting of CH, C—CN, C=O,
wherein the bold line is an optional double bond;
$R_1$ is independently selected from the group consisting of hydrogen, methoxy, cyano, halogen, hydroxyl, $C_{1-6}$ alkoxy and $C_{1-6}$ alkyl optionally substituted with one or two $C_{1-6}$ alkoxy;
$A_1$-G-$A_2$-NH-$A_3$-$R_6$ is selected from the group of formulae consisting of G1, G2, G3, G4, G5, G6, G7, G8, G9 and G10 as provided below

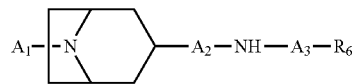

G1

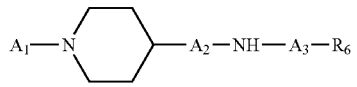

G2

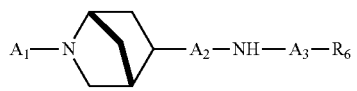

G3

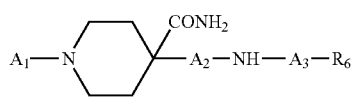

G4

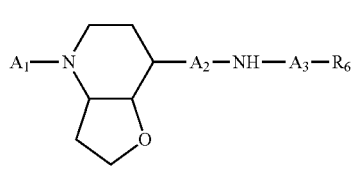

G5

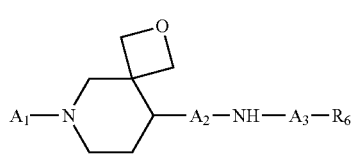

G6

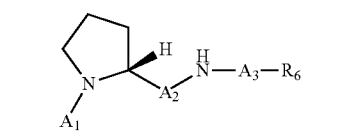

G7

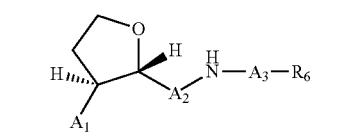

G8

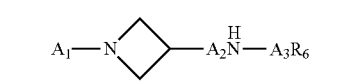

G9

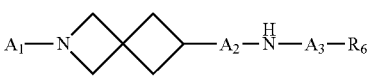

G10 wherein, $A_1$ is selected from the group consisting of
—$(CR_2R_3)_m$—$CH_2$—, —$CH_2$—$(CR_2R_3)_m$—, —NH—$(CR_2R_3)_m$—$CH_2$, —$(CR_2R_3)_m$—$CH_2$—O— and

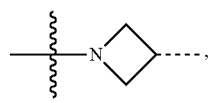

wherein when Z6 is C—CN and A1-G-A2-NH-A3-R6 is G2, A1 is

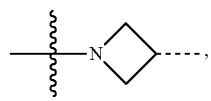

m is 1 or 2;

- - - - - is connectivity to G;

$R_2$ is selected from the group consisting of hydrogen, halogen, acyloxy, $C_{1-6}$ alkyl optionally substituted with one or two $C_{1-6}$ alkoxy and $C_{1-6}$ alkoxy optionally substituted with $C_{1-6}$ alkyl;

$R_3$ is hydrogen;

$A_2$ is $CR_4R_5$ or is absent; wherein $R_4$ and $R_5$ are each independently hydrogen or $C_{1-6}$ alkyl;

$A_3$ is —$CH_2$—, C(=O) or $SO_2$; and wherein, $R_6$ is selected from the group consisting of
(i) a substituted or unsubstituted monocyclic or substituted or unsubstituted bicyclic aryl; and
(ii) a substituted or unsubstituted monocyclic or substituted or unsubstituted bicyclic heteroaryl.

2. A compound selected from the group consisting of:

VT-03-00014: 4-(2-(3-([1,3]oxathiolo[5,4-c]pyridin-6-ylmethylamino)-8 azabicyclo[3.2.1]octan-8-yl)ethyl)-6-methoxyquinoline-3-carbonitrile;

VT-03-00017: N-(8-(2-(3-cyano-6-methoxyquinolin-4-yl)ethyl)-8-azabicyclo[3.2.1]octan-3-yl)-2-methylbenzenesulfonamide;

VT-03-00021: N-(8-(2-(3-cyano-6-methoxyquinolin-4-yl)ethyl)-8-azabicyclo[3.2.1]octan-3-yl)-2,3-dihydrobenzo[b][1,4]dioxine-6-sulfonamide;

VT-03-00021a: 4-(2-(3-((2,3-dihydrobenzo[b][1,4]dioxin-6-yl)methylamino)-8azabicyclo[3.2.1]octan-8-yl)ethyl)-6-methoxyquinoline-3-carbonitrile;

VT-03-00022: N-(8-(2-(3-cyano-6-methoxyquinolin-4-yl)ethyl)-8-azabicyclo[3.2.1]octan-3-yl)naphthalene-2-sulfonamide;

VT-03-00024: N-(8-(2-(3-cyano-6-methoxyquinolin-4-yl)ethyl)-8-azabicyclo[3.2.1]octan-3-yl)-2,3-dihydrobenzo[b][1,4]dioxine-6-carboxamide;

VT-03-00026: 6-methoxy-4-(2-(3-((3-oxo-3,4-dihydro-2H-benzo[b][1,4]thiazin-6-yl)methylamino)-8-azabicyclo[3.2.1]octan-8-yl)ethyl)quinoline-3-carbonitrile;

VT-03-00026a: 4-(2-(3-((3,4-dihydro-2H-benzo[b][1,4]thiazin-6-yl)methylamino)-8-azabicyclo[3.2.1]octan-8-yl)ethyl)-6-methoxyquinoline-3-carbonitrile;

VT-03-00027: 4-(2-(3-((2,3-dihydro-[1,4]dioxino[2,3-c]pyridin-7-yl)methylamino)-8-azabicyclo[3.2.1]octan-8-yl)ethyl)-6-methoxyquinoline-3-carbonitrile;

VT-03-00028: 4-(2-((1R,4R)-5-((2,3-dihydrobenzo[b][1,4]dioxin-6-ylamino)methyl)-2,5-diazabicyclo[2.2.1]heptan-2-yl)ethyl)-6-methoxyquinoline-3-carbonitrile;

VT-03-00030: 6-methoxy-4-(2-(3-((3-oxo-3,4-dihydro-2H-benzo[b][1,4]oxazin-6-yl)methylamino)-8-azabicyclo[3.2.1]octan-8-yl)ethyl)quinoline-3-carbonitrile;

VT-03-00031: 4-(2-(3-((7-fluoro-2,3-dihydrobenzo[b][1,4]dioxin-6-yl)methylamino)-8-azabicyclo[3.2.1]octan-8-yl)ethyl)-6-methoxyquinoline-3-carbonitrile;

VT-03-00032: 4-(3-(4-((2,3-dihydrobenzo[b][1,4]dioxin-6-yl)methylamino)piperidin-1-yl)azetidin-1-yl)-6-methoxyquinoline-3-carbonitrile;

VT-03-00042: 6-methoxy-1-methyl-2-oxo-4-(2-(4-((3-oxo-3,4-dihydro-2H-benzo[b][1,4]oxazin-6-yl)methylamino)piperidin-1-yl)ethyl)-1,2-dihydroquinoline-3-carbonitrile;

VT-03-00043: 4-(2-(4-((2,3-dihydrobenzo[b][1,4]dioxin-6-yl)methylamino)piperidin-1-yl)ethyl)-6-methoxy-1-methyl-2-oxo-1,2-dihydroquinoline-3-carbonitrile;

VT-03-00045: 6-methoxy-4-(2-(4-(4-nitrobenzylamino)piperidin-1-yl)ethyl)quinoline-3-carbonitrile;

VT-03-00046: 4-(2-(4-(4-hydroxy-3-methoxybenzylamino)piperidin-1-yl)ethyl)-6-methoxyquinoline-3-carbonitrile;

VT-03-00048: 4-(2-(4-(4-fluoro-3-nitrobenzylamino)piperidin-1-yl)ethyl)-6-methoxyquinoline-3-carbonitrile;

VT-03-00049: 6-methoxy-4-(2-(4-(3-nitrobenzylamino)piperidin-1-yl)ethyl)quinoline-3-carbonitrile;

VT-03-00050: 4-(2-(4-(2-fluoro-5-nitrobenzylamino)piperidin-1-yl)ethyl)-6-methoxyquinoline-3-carbonitrile;

VT-03-00051: 6-methoxy-4-(2-(4-((5-nitrofuran-2-yl)methylamino)piperidin-1-yl)ethyl)quinoline-3-carbonitrile;

VT-03-00052: 6-methoxy-4-(2-(4-((5-nitrothiophen-2-yl)methylamino)piperidin-1-yl)ethyl)quinoline-3-carbonitrile;

VT-03-00053: 6-methoxy-4-(2-(4-((5-nitrothiophen-3-yl)methylamino)piperidin-1-yl)ethyl)quinoline-3-carbonitrile;

VT-03-00054: 4-(2-(4-(3-fluoro-4-nitrobenzylamino)piperidin-1-yl)ethyl)-6-methoxyquinoline-3-carbonitrile;

VT-03-00055: N-(1-(2-(3-cyano-6-methoxyquinolin-4-yl)ethyl)piperidin-4-yl)-3-fluoro-4-nitrobenzamide;

VT-03-00056: 1-(2-(4-(4-fluoro-3-nitrobenzylamino)piperidin-1-yl)ethyl)-7-methoxyquinoxalin-2(1H)-one;

VT-03-00057: 7-methoxy-1-(2-(4-((5-nitrothiophen-3-yl)methylamino)piperidin-1-yl)ethyl)quinoxalin-2(1H)-one;

VT-03-00058: 4-(2-(4-(4-chloro-3-nitrobenzylamino)piperidin-1-yl)ethyl)-6-methoxyquinoline-3-carbonitrile;

VT-03-00059: 4-(2-(4-(2-hydroxy-5-nitrobenzylamino)piperidin-1-yl)ethyl)-6-methoxyquinoline-3-carbonitrile;

VT-03-00060: 4-(2-(4-(4-hydroxy-3-methoxy-5-nitrobenzylamino)piperidin-1-yl)ethyl)-6-methoxyquinoline-3-carbonitrile;

VT-03-00061: 6-methoxy-4-(2-(4-(4-methyl-3-nitrobenzylamino)piperidin-1-yl)ethyl)quinoline-3-carbonitrile;

VT-03-00062: 7-methoxy-1-(2-(4-(4-methyl-3-nitrobenzylamino)piperidin-1-yl)ethyl)quinoxalin-2(1H)-one;

VT-03-00062a: 1-(2-(7-methoxyquinoxalin-2-yloxy)ethyl)-N-(4-methyl-3-nitrobenzyl)piperidin-4-amine;

VT-03-00063: 6-methoxy-4-(2-(4-(4-methoxy-3-nitrobenzylamino)piperidin-1-yl)ethyl)quinoline-3-carbonitrile;

VT-03-00064: 4-(2-(4-(4-(dimethylamino)-3-nitrobenzylamino)piperidin-1-yl)ethyl)-6-methoxyquinoline-3-carbonitrile;

VT-03-00065: 1-(2-(4-(4-methyl-3-nitrobenzylamino)piperidin-1-yl)ethyl)-2-oxo-1,2-dihydroquinoline-7-carbonitrile;

VT-03-00066: 1-(2-(4-(4-bromo-3-nitrobenzylamino)piperidin-1-yl)ethyl)-7-methoxyquinoxalin-2(1H)-one;

VT-03-00067: 7-methoxy-1-(2-(4-(3-methyl-4-nitrobenzylamino)piperidin-1-yl)ethyl)quinoxalin-2(1H)-one;

VT-03-00069: 6-methoxy-4-(2-((1R,5S)-3-(4-methyl-3-nitrobenzylamino)-8-azabicyclo[3.2.1]octan-8-yl)ethyl)quinoline-3-carbonitrile;

VT-03-00070: 6-methoxy-4-(2-((1R,5S)-3-((7-nitrobenzo[d][1,3]dioxol-5-yl)methylamino)-8-azabicyclo[3.2.1]octan-8-yl)ethyl)quinoline-3-carbonitrile;

VT-03-00071: 4-(2-((1R,5S)-3-(2,5-dimethyl-3-nitrobenzylamino)-8-azabicyclo[3.2.1]octan-8-yl)ethyl)-6-methoxyquinoline-3-carbonitrile;

VT-03-00072: 6-methoxy-4-(2((1R,5S)-3-((5-nitrothiophen-2-yl)methylamino)-8-azabicyclo[3.2.1]octan-8-yl)ethyl)quinoline-3-carbonitrile;

VT-03-00074: 4-(2-(4-(2,5-dimethyl-3-nitrobenzylamino)piperidin-1-yl)ethyl)-6-methoxyquinoline-3-carbonitrile;
VT-03-00075: 4-(2-(4-(2,4-dimethyl-5-nitrobenzylamino)piperidin-1-yl)ethyl)-6-methoxyquinoline-3-carbonitrile;
VT-03-00076: 4-(2-(4-(4-ethyl-3-nitrobenzylamino)piperidin-1-yl)ethyl)-6-methoxyquinoline-3-carbonitrile;
VT-03-00077: 6-methoxy-4-(2-(4-((7-nitrobenzo[d][1,3]dioxol-5-yl)methylamino)piperidin-1-yl)ethyl)quinoline-3-carbonitrile;
VT-03-00078: 6-methoxy-4-(2-(4-((5-nitro-1H-imidazol-2-yl)methylamino)piperidin-1-yl)ethyl)quinoline-3-carbonitrile;
VT-03-00079: 6-methoxy-4-(2-(4-((4-nitropyridin-2-yl)methylamino)piperidin-1-yl)ethyl)quinoline-3-carbonitrile;
VT-03-00080: 6-methoxy-4-(2-(4-((2-nitrothiazol-4-yl)methylamino)piperidin-1-yl)ethyl)quinoline-3-carbonitrile;
VT-03-00081: 6-methoxy-4-(2-(4-((5-nitropyridin-2-yl)methylamino)piperidin-1-yl)ethyl)quinoline-3-carbonitrile;
VT-03-00083: 1-(2-(3-cyano-6-methoxyquinolin-4-yl)ethyl)-4-(4-methyl-3-nitrobenzylamino)piperidine-4-carboxamide;
VT-03-00084: 6-methoxy-4-(2-(3-((4-methyl-3-nitrobenzylamino)methyl)azetidin-1-yl)ethyl)quinoline-3-carbonitrile;
VT-03-00085: 6-methoxy-4-(2-(6-(4-methyl-3-nitrobenzylamino)-2-azaspiro[3.3]heptan-2-yl)ethyl)quinoline-3-carbonitrile;
VT-03-00086: (R)-6-methoxy-4-(2-(2-((4-methyl-3-nitrobenzylamino)methyl)pyrrolidin-1-yl)ethyl)quinoline-3-carbonitrile;
VT-03-00087: 6-methoxy-4-(2-(9-(4-methyl-3-nitrobenzylamino)-2-oxa-6-azaspiro[3.5]nonan-6-yl)ethyl)quinoline-3-carbonitrile;
VT-03-00088: 6-methoxy-4-(2-(4-((6-methylpyridin-3-yl)methylamino)piperidin-1-yl)ethyl)quinoline-3-carbonitrile;
VT-03-00089: 4-(2-(4-(2,3-difluoro-4-methylbenzylamino)piperidin-1-yl)ethyl)-6-methoxyquinoline-3-carbonitrile;
VT-03-00090: 6-methoxy-4-(2-(4-(4-methyl-3-(trifluoromethyl)benzylamino)piperidin-1-yl)ethyl)quinoline-3-carbonitrile;
VT-03-00091: 6-methoxy-4-(2-(4-(4-methyl-3-(trifluoromethoxy)benzylamino)piperidin-1-yl)ethyl)quinoline-3-carbonitrile;
VT-03-00092: 4-(2-(4-(3-acetyl-4-methylbenzylamino)piperidin-1-yl)ethyl)-6-methoxyquinoline-3-carbonitrile;
VT-03-00093: 4-(2-(4-(3-cyano-4-methylbenzylamino)piperidin-1-yl)ethyl)-6-methoxyquinoline-3-carbonitrile;
VT-03-00094: 6-methoxy-4-(2-(4-(4-methyl-3-(1,1,1-trifluoropropan-2-yl)benzylamino)piperidin-1-yl)ethyl)quinoline-3-carbonitrile; and
VT-03-00095: 4-(2-(4-(3-fluoro-4-methylbenzylamino)piperidin-1-yl)ethyl)-6-methoxyquinoline-3-carbonitrile.

3. A method of treating a patient suffering from an infection comprising administering an effective amount of a compound of claim 1, wherein the infection is caused by at least one of *Staphylococcus* species, *Enterococcus* species, *Streptococcus* species, *Moraxella* species, *E. coli*, *Klebsiella* species, *Pseudomonas* species, or *Acinetobacter* species.

4. A method of treating a patient suffering from an infection comprising administering an effective amount of a compound of claim 2, wherein the infection is caused by at least one of *Staphylococcus* species, *Enterococcus* species, *Streptococcus* species, *Moraxella* species, *E. coli*, *Klebsiella* species, *Pseudomonas* species, or *Acinetobacter* species.

5. The compound of claim 1, wherein the $R_6$ aryl or heteroaryl comprises a five or six membered ring.

6. The compound of claim 5, wherein the five or six membered ring bears one or two hetero atoms (N, O, S).

7. The compound of claim 1, wherein the $R_6$ aryl or heteroaryl includes a substitution independently selected from the group consisting of halogen (F, Cl, Br), $NO_2$, CN, OMe, Me, $CF_3$, $OCF_3$, Ethyl, Butyl, isobutyl, small alkyl chain substituted with halogen, amino, $NMe_2$ alkoxy, carbonyl and sulfonyl.

8. The compound of claim 1, wherein the $R_6$ aryl or heteroaryl is fused to saturated or unsaturated cyclic ring containing at least one heteroatom selected from the group consisting of oxygen, nitrogen and sulphur which is optionally substituted with halogen, $C_{1-6}$ alkyl, $C_{1-6}$ alkoxy, $C_{1-6}$ alkyl substituted with $C_{1-6}$ alkoxy, $C_{1-6}$ alkoxy optionally substituted with $C_{1-6}$ alkyl, $C_{1-4}$ haloalkoxy, $C_{1-4}$ haloalkyl, $C_{1-4}$ thioalkyl, nitro, cyano, carboxy, $C_{1-4}$ alkylsulfonyl, aminosulfonyl, hydroxyl, amino, aminoalkyl, oxo, hydroxyalkyl, alkynyl, alkylcarbonyl and carbonyl.

\* \* \* \* \*